US007510824B2

(12) United States Patent
Tymianski

(10) Patent No.: US 7,510,824 B2
(45) Date of Patent: Mar. 31, 2009

(54) METHOD OF SCREENING PEPTIDES USEFUL IN TREATING TRAUMATIC INJURY TO THE BRAIN OR SPINAL CORD

(75) Inventor: Michael Tymianski, Toronto (CA)

(73) Assignee: NoNO Inc., Toronto (CA)

( * ) Notice: Subject to any disclaimer, the term of this patent is extended or adjusted under 35 U.S.C. 154(b) by 507 days.

(21) Appl. No.: 10/930,192

(22) Filed: Aug. 31, 2004

(65) Prior Publication Data

US 2005/0059597 A1 Mar. 17, 2005

Related U.S. Application Data

(63) Continuation-in-part of application No. 10/208,374, filed on Jul. 30, 2002, which is a continuation-in-part of application No. 09/584,555, filed on May 31, 2000, now abandoned.

(51) Int. Cl.
*C12Q 1/00* (2006.01)
(52) U.S. Cl. ............................................. 435/4; 436/503
(58) Field of Classification Search ....................... None
See application file for complete search history.

(56) References Cited

U.S. PATENT DOCUMENTS

| 6,911,526 B2 | 6/2005 | Sato et al. |
| 6,942,981 B1 | 9/2005 | Lu et al. |
| 2002/0147306 A1 | 10/2002 | Lin |
| 2003/0050243 A1 | 3/2003 | Tymianski |
| 2005/0059597 A1 | 3/2005 | Tymianski |

FOREIGN PATENT DOCUMENTS

| CA | 2273622 A1 | | 2/2000 |
| WO | WO 97/33173 | * | 9/1997 |
| WO | WO 97/33173 A1 | | 9/1997 |

OTHER PUBLICATIONS

Arundine et al (2003). J Neurotrauma. 20, 1377-1396.*
Schwarze et al (1999). Science. 285, 1569-1572.*
Arundine et al. Soc. Neurosci. Abstracts, vol. 27, 2001, p. 569.*
Liu et al. Soc. Neurosci. Abstract Viewer and Itinerary Planner, vol. 2002, 2002, page Abstract No. 245.3.*
Kornau et al., Science 269: 1737-1740, 1995.
Niethammer et al., Neuron 20: 693-707, 1998.
Wang et al., PNAS 93: 1721-1725, 1996.
U.S. Appl. No. 11/894,818, filed Aug. 20, 2007, Tymianski.
Aarts et al., "Treatment of Ischemic Damage by Perturbing NMDA Receptor-PSD-95 Protein Interactions," *Science*, 298:846-850 (2002).
Arundine et al., "Enhanced Vulnerability to NMDA Toxicity in Sublethal Traumatic Neuronal Injury In Vitro," *Journal of Neurotrauma*, 20(12):1377-1396 (2003).
Bassand et al., "Differential interaction of the tSXV motifs of the NR1 and NR2A NMDA receptor subunits with PSD-95 and SAP97," *Eur. J. Neuroscience*, 11:2031-2043 (1999).

Beal, "Mechanisms of excitoxicity in neurologic diseases" *FASEB J.*, 6:3338-3344 (1992).
Bezprozvanny et al., "Classification of PDZ domains," *FEBS Letters*, 509:457-462 (2001).
Branswell, "New stroke drug shows promise in animal trials" *CTV.ca*, Canadian Press (ca. Oct. 25, 2002).
Brenman et al., "Cloning and Characterization of Postsynaptic Density 93, a Nitric Oxide Synthase Interacting Protein," *J. Neuroscience*, 16(23):7407-7415 (1996).
Buchan et al., "Failure to prevent selected CA1 neuronal death and reduce cortical infarction following cerebral ischemia with inhibition of nitric oxide synthase" *Neuroscience* 61(1):1-11 (1994).
Christopherson et al., "PSD-95 Assembles a Ternary Complex with N-Methyl-D-aspartic Acid Receptor and a Bivalent Neuronal NO Synthase PDZ Domain," *J. Biol. Chem.*, 274(39):27467-27473 (1999).
Cohen et al., "Binding of the inward rectifier K+ channel Kir 2.3 to PSD-95 is regulated by protein kinase A phosphorylation," *Neuron*, 17(4):759-767 (1996).
Cregan et al., "[(S)-Alpha-Phenyl-2-Pyridine-Ethanamine Dihydrochloride], A Low Affinity Uncompetitive N-Methyl-D-Aspartic Acid Antagonist, is Effective in Rodent Models of Global and Focal Ischemia," *J. Pharm. Exp. Therap.*, 283(3):1412-1424 (1997).
Davis et al., "Termination of acute stroke studies involving Selfotel treatment" *The Lancet*, 349:32 (1997).
Davis et al., "Selfotel in Acute Ischemic Stroke Possible Neurotoxic Effects of an NMDA Antagonist," *Stroke*, 31:347-354 (2000).
Dawson et al., "Inhibition of nitric oxide synthesis does not reduce infarct volume in a rat model of focal cerebral ischaemia" *Neurosci. Lett.*, 142:151-154 (1992).
Dotinga, "Synthetic protein protects rats from stroke" Healthcentral (Oct. 24, 2002).
Doyle et al., "Crystal structures of a complexed and peptide-free membrane protein-binding domain: molecular basis of peptide recognition by PDZ," *Cell*, 85(7):1067-1076 (1996).
Dyker et al., "Safety and tolerability study of Aptiganel Hydrochloride in patients with an acute ischemic stroke" *Stroke* 30:2038-2042 (1999).
El-Maghrabi et al., "Saturable binding of halothane to rat brain synaptosomes," *PNAS*, 89:4329-4332 (1992).
Excerpt entitled: "New stroke drug may limit brain damage," *Canadian Press* (Oct. 25, 2002).
Excerpt entitled: "New drug prevents brain damage from stroke" Discoveryhealth.com (Oct. 25, 2002).
Excerpt entitled: "Stroke solutions" *CBC Radio One* (Oct. 25, 2002).
Excerpt entitled "A gentler treatment for stroke" *Science*, 298:699-701 (Oct. 25, 2002).

(Continued)

*Primary Examiner*—Jeffrey Stucker
*Assistant Examiner*—Stephen Gucker
(74) *Attorney, Agent, or Firm*—Townsend and Townsend and Crew, LLP

(57) ABSTRACT

A method of screening peptides which bind to at least one PDZ domain and comprise a cell-membrane transduction domain for use in treating traumatic injury to the brain or spinal cord by deforming neurons on a flexible substrate with sublethal stretch, then inflicting a secondary injury, and determining survival of the stretched neurons in the absence or presence of the peptide which is being screened.

8 Claims, 62 Drawing Sheets

OTHER PUBLICATIONS

Excerpt entitled: "Researchers prevent cell death in rats with stroke" *HeartCenterOnline for Patients*™ (Oct. 25, 2002).

Fang et al., "Synaptic PDZ Domain-mediated Protein Interactions Are Disrupted by Inhalational Anesthetics," *J. Biol. Chem.*, 278(30):36669-36675 (2003).

Ferrer-Montiel et al., "Selected peptides targeted to the NMDA receptor channel protect neurons from excitotoxic death," *Nature Biotechnology*, 16(3):286-291 (1998).

Fix et al., "Neuronal Vacuolization and Necrosis Induced by the Noncompetitive N-methyl-D-asparate (NMDA) Antagonist MK(+)801 (Dizocilpine Maleate): A Light and Electron Microscope Evaluation of the Rat Retrospinal Cortex," *Experimental Neurology*, 123:204-215 (1993).

Fuh et al., "Analysis of PDZ Domain-Ligand Interactions Using Carboxyl-terminal Phage Display," *J. Biol. Chem.*, 275(28):21486-21491 (2000).

Gee et al., "Single-amino acid substitutions alter the specificity and affinity of PDZ domains for their ligands," *Biochemistry*, 39(47):14638-14646 (2000).

Grotta et al., "Safety and tolerability of the Glutamate antagonist CGS 19755 (Selfotel) in patients with acute ischemic stroke" *Stroke*, 26:602-605 (1995).

Harris et al., "Mechanism and role of PDZ domains in signaling complex assembly," *J. Cell Science*, 114:3219-3231 (2001).

Hirbec et al., "The PDZ Proteins PICK1, GRIP, and Syntenin Bind Multiple Glutamate Receptor Subtypes," *J. Biol. Chem.*, 277(18):15221-15224 (2002).

Horio et al., "Clustering and Enhanced Activity of an Inwardly Rectifying Potassium Channel, Kir4.1, by an Anchoring Protein, PSD-95/SAP90," *J. Biol. Chem.*, 272(20):12885-12888 (1997).

Hsueh et al., "Disulfide-Linked Head-to-Head Multimerization in the Mechanism of Ion Channel Clustering by PSD-95," *Neuron*, 18:803-814 (1997).

Hu et al., "$\beta_1$-Adrenergic Receptor Association with PSD-95," *J. Biol. Chem.*, 275(49):38659-38666 (2000).

Hudzik et al., "Effects of anticonvulsants in a novel operant learning paradigm in rats: Comparison of remacemide hydrochloride and FPL 15896AR to other anticonvulsant agents," *Epilepsy Research*, 21:183-193 (1995).

Im et al., "Crystal Structure of the Shank PDZ-Ligand Complex Reveals a Class I PDZ Interaction and a Novel PDZ-PDZ Dimerization," *J. Biol. Chem.*, 278(48):48099-48104 (2003).

Irie et al., "Binding of Neuroligins to PSD-95," *Science*, 277:1511-1515 (1997).

Jaffery et al., "Capon: A Protein Associated with Neuronal Nitric Oxide Synthase that Regulates Its Interactions With PSD95," *Neuron*, 20:115-124 (1998).

Jones, "Blocking the pathway to excitotoxicity" *Nature Reviews Neuroscience*, 3 (2002).

Kim et al., "Plasma Membrane $Ca^{2+}$ ATPase Isoform 4b Binds to Membrane-associated Guanylate Kinase (MAGUK) Proteins via Their PDZ (PSD-95/Dig/ZO-1) Domains," *J. Biol. Chem.*, 273(3):1591-1595 (1998).

Kim et al., "Clustering of Shaker-type K+ channels by interaction with a family of membrane-associated guanylate kinases," *Nature*, 378(6652):85-88 (1995).

Lees, "Cerestat and other NMDA antagonists in ischemic stroke" *Neurology*, 49(Supp. 4): S66-S69 (1997).

Lim et al., "Selectivity and Promiscuity of the First and Second PDZ Domains of PSD-95 and Synapse-assoicated Protein 102," *J. Biol. Chem.*, 277(24):21697-21711 (2002).

Matsumine et al., "Binding of APC to the human homolog of the Drosophila discs large tumor suppressor protein," *Science*, 272(5264):974-975 (1996).

McCook, "Researches prevent cell death in rats with stroke" Reuters.com, (Oct. 24, 2002).

Meldrum et al., "Excitotoxicity and epileptic brain damage" *Epilepsy Res.*, 10:55-61 (1991).

Morris et al., "Failure of the competitive N-methyl-D-aspartate antagonist Selfotel (CGS 19755) in the treatment of severe head injury: results of two Phase III clinical trials," *J. Neurosurg.*, 91:737-743 (1999).

Muir, "Pharmacological effects of the non-competitive NMDA antagonist CNS 1102 in normal volunteers" *Br. J. Clin. Pharmac.*, 38:33-38 (1994).

Muller et al., "Molecular Characterization and Spatial Distribution of SAP97, a Novel Presynaptic Protein Homologous to SAP90 and the Drosophilia Discs-Large Tumor Suppressor Protein," *J. Neuroscience*, 15(3):2354-2366 (1995).

Niethammer et al., "Interaction between the C Terminus of NMDA Receptor Subunits and Multiple Members of the PSD-95 Family of Membrane-Associated Guanylate Kinases," *J. Neuroscience*, 16(7):2157-2163 (1996).

O'Brien et al., "Molecular mechanisms of glutamate receptor clustering at excitatory synapses," *Curr. Opin. Neurobiol.*, 8(3):364-369 (1998).

Oransky, "NMDA receptors and stroke therapy" *The Lancet Neurology* 1:463 (2002).

Porter, "Drug could ease strokes" thestar.com (Oct. 25, 2002).

Porter, "Drug could ease strokes" *The Toronto Star* (Oct. 25, 2002).

Saito et al., "Reduction of Infarct Volume by Halothane: Effect on Cerebral Blood Flow or Perifocal Spreading Depression-like Depolarizations," *Journal of Cerebral Blood Flow & Metabolism*, 17:857-864 (1997).

Saro et al., "Thermodynamic analysis of a hydrophobic binding site: probing the PDZ domain with nonproteinogenic peptide ligands," *Org. Lett.*, 6(20):3429-3432 (2004).

Schwarze et al., "In Vivo Protein Transduction: Delivery of a Biologically Active Protein into the Mouse," *Science*, 285:1569-1572 (1999).

Shan et al., "Identification of a specific inhibitor of the disheveled PDZ domain," *Biochemistry*, 44(47):15495-15503 (2005).

Sheng et al., "PDZ domains and the organization of supramolecular complexes," *Annu. Rev. Neurosci.*, 24:1-29 (2001).

Smith, "Stroke drug could prevent brain damage" *United Press International* (Oct. 24, 2002).

Songyang et al., "Recognition of Unique Carboxyl-Terminal Motifs by Distinct PDZ Domains," *Science*, 275:73-77 (1997).

Tatlisumak et al., "A Glycine Site Antagonist ZD9379, Reduces Number of Spreading Depressions and Infarct Size in Rats with Permanent Middle Cerebral Artery Occlusion," *Stroke*, 29:190-195 (1998).

Thomas et al., "Synaptic clustering of the cell adhesion molecule fasciclin II by discs-large and its role in the regulation of presynaptic structure," *Neuron*, 19(4):787-799 (1997).

Tsai et al., "The glutamatergic basis of human alcoholism" *Am. J. Psychiatry*, 152(3):332-340 (1995).

Wang et al., "Formation of a native-like beta-haripin finger structure of a peptide from the extended PDZ domain of neuronal nitric oxide synthase in aqueous solution," *Eur. J. Biochem.*, 267(11):3116-3122 (2000).

Yamamoto et al., "Inhibition of nitric oxide synthesis increases focal ischemic infarction in rat" *J. Cereb. Blood Flow. Metab.*, 12:717-726 (1992).

Yanagisawa et al., "The Molecular Interaction of Fas and FAP-1, A Tripeptide Blocker of Human Fas Interaction with FAP-1 Promotes Fas-Induced Apoptosis," *J. Biol. Chem.*, 272(13):8539-8545 (1997).

* cited by examiner

FIG. 2A1
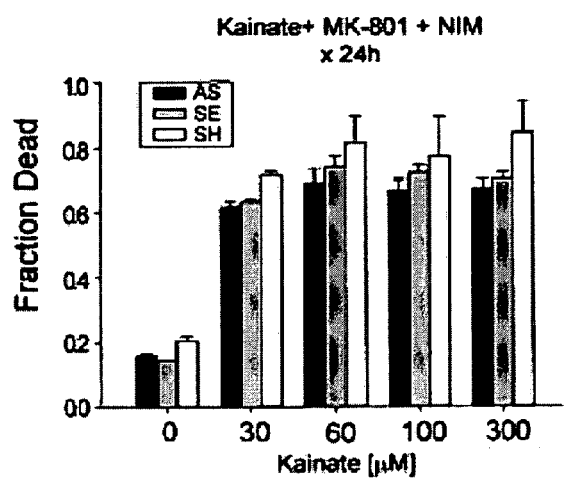
FIG. 2A2
FIG. 2B1
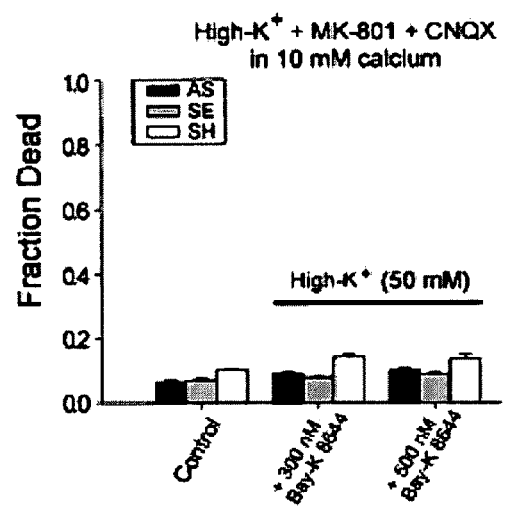
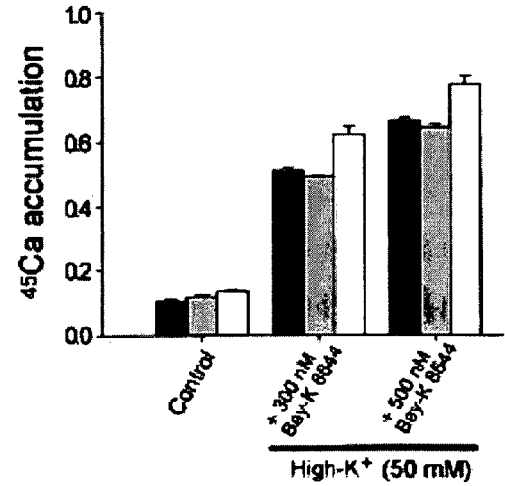
FIG. 2B2

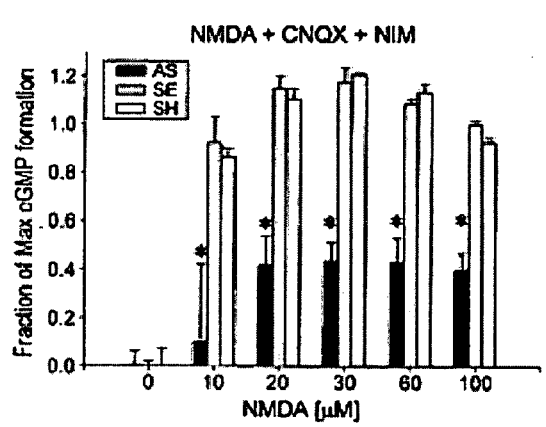
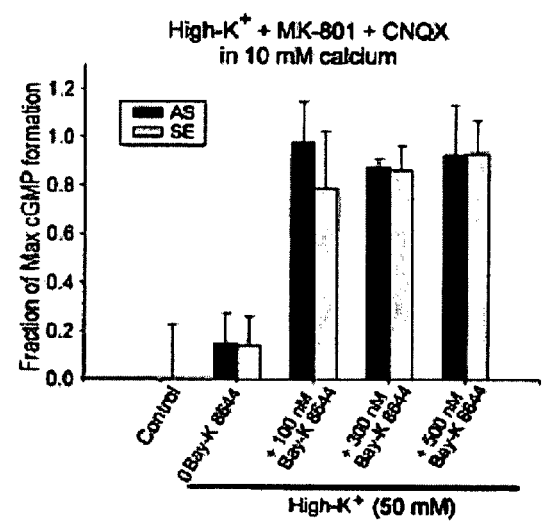
FIG. 4C
FIG. 4D

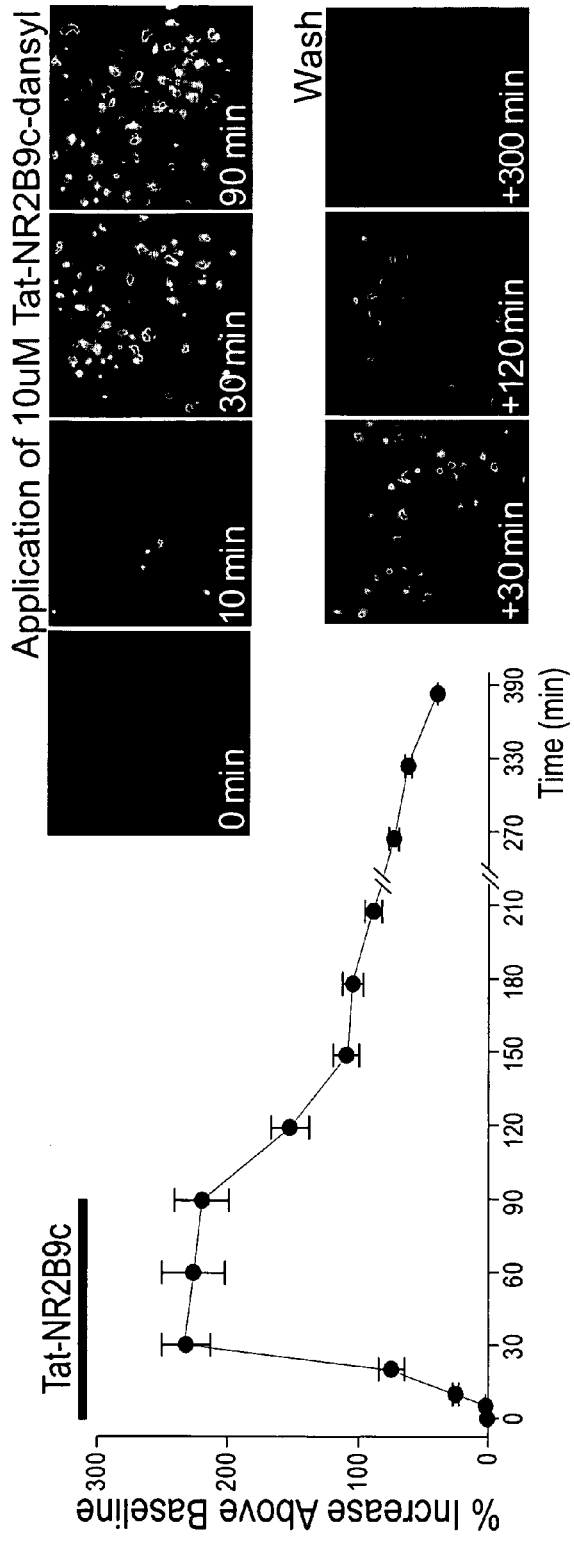
FIG. 5C
FIG. 5D

FIG. 16Bi
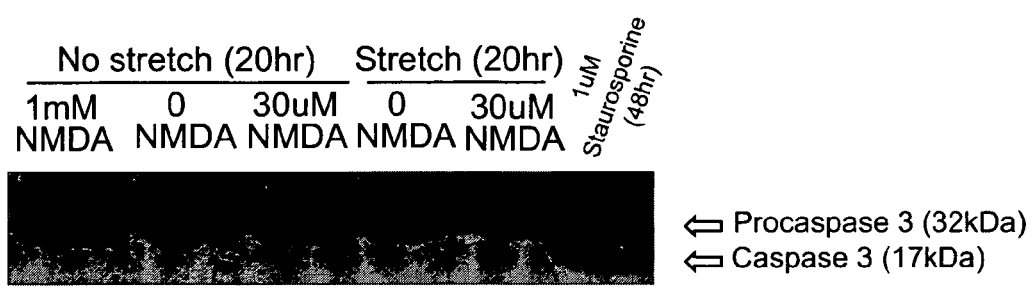
FIG. 16Bii
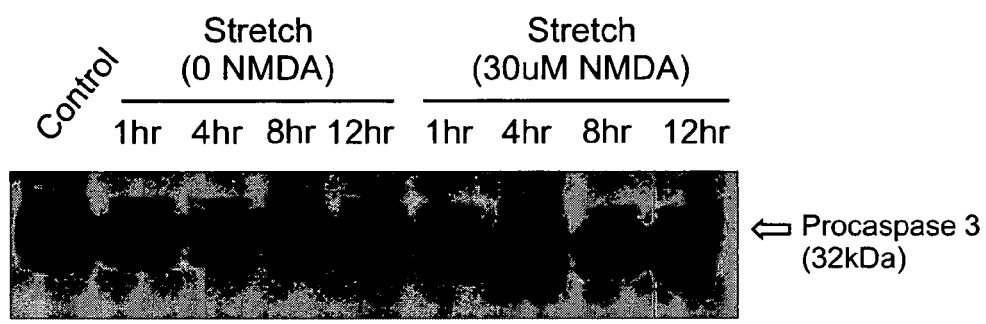

A: Control

B: Stretch

C: Stretch; 30uM NMDAI

D: Stretch; 30uM NMDA 200uM zvadFMK

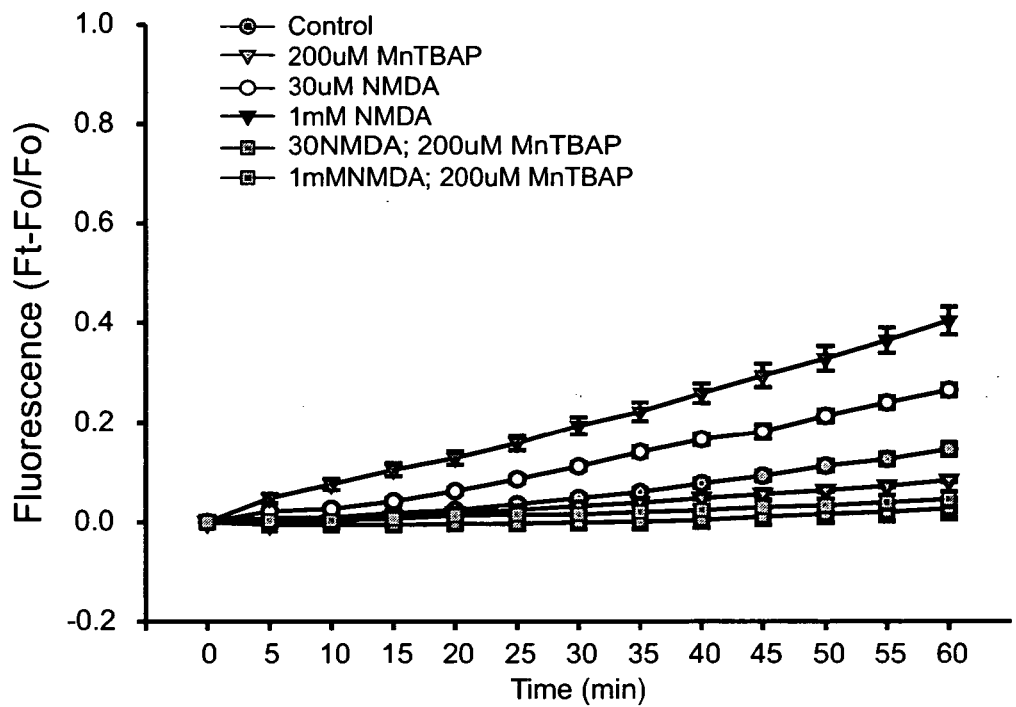
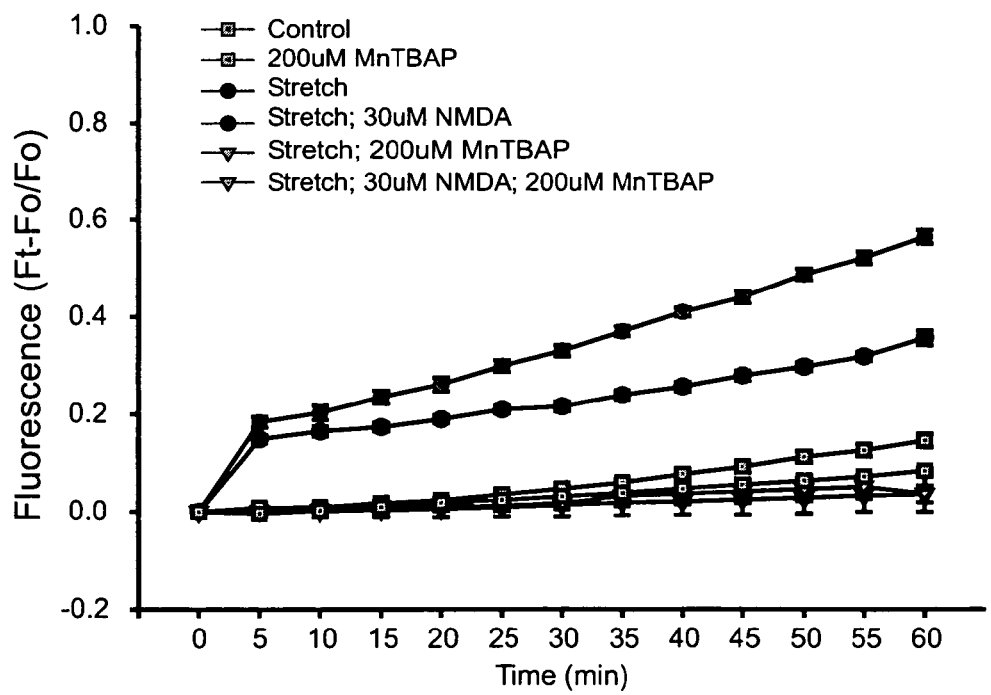
FIG. 20C

TAT 38-48 dansyl   TAT-NR2B9c-dansyl
 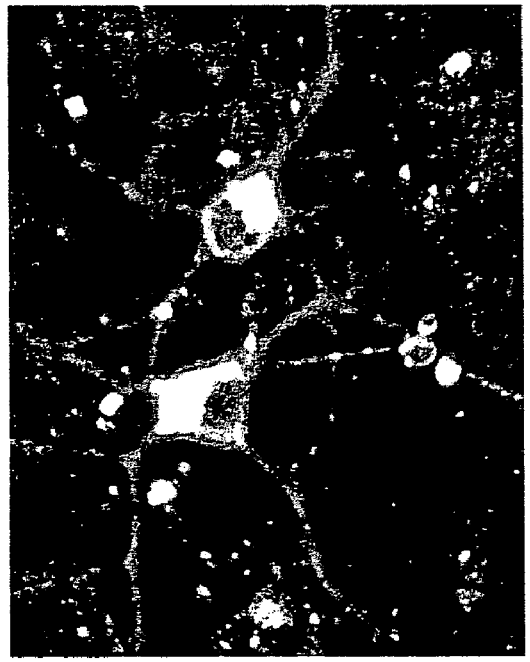
50μm
FIG. 23C

US 7,510,824 B2

METHOD OF SCREENING PEPTIDES USEFUL IN TREATING TRAUMATIC INJURY TO THE BRAIN OR SPINAL CORD

CROSS REFERENCE TO RELATED APPLICATIONS

This application is a continuation-in-part application of Ser. No. 10/208,374, filed Jul. 30, 2002, which is itself a continuation-in-part application of Ser. No. 09/584,555, filed May 31, 2000 now abandoned. The disclosures of those applications are hereby incorporated herein by reference.

BACKGROUND OF THE INVENTION

1. Field of the Invention

This invention generally relates to compositions and methods for reducing the damaging effect of an injury to mammalian cells by treatment with compounds which reduce the binding between N-methyl-D-aspartate receptors and neuronal proteins. More particularly, the invention relates to such compounds, pharmaceutical compositions comprising said compounds, and methods for the preparation and use of said pharmaceutical compositions.

2. Description of Related Art

Ischemic or traumatic injuries to the brain or spinal cord often produce irreversible damage to central nervous system (CNS) neurons and to their processes. These injuries are major problems to society as they occur frequently, the damage is often severe, and at present there are still no effective pharmacological treatments for acute CNS injuries. Clinically, ischemic cerebral stroke or spinal cord injuries manifest themselves as acute deteriorations in neurological capacity ranging from small focal defects, to catastrophic global dysfunction, to death. It is currently felt that the final magnitude of the deficit is dictated by the nature and extent of the primary physical insult, and by a time-dependent sequence of evolving secondary phenomena which cause further neuronal death. Thus, there exists a theoretical time-window, of uncertain duration, in which a timely intervention might interrupt the events causing delayed neurotoxicity. However, little is known about the cellular mechanisms triggering and maintaining the processes of ischemic or traumatic neuronal death, making it difficult to devise practical preventative strategies. Consequently, there are currently no clinically useful pharmacological treatments for cerebral stroke or spinal cord injury.

In vivo, a local reduction in CNS tissue perfusion mediates neuronal death in both hypoxic and traumatic CNS injuries. Local hypoperfusion is usually caused by a physical disruption of the local vasculature, vessel thrombosis, vasospasm, or luminal occlusion by an embolic mass. Regardless of its etiology, the resulting ischemia is believed to damage susceptible neurons by impacting adversely on a variety of cellular homeostatic mechanisms. Although the nature of the exact disturbances is poorly understood, a feature common to many experimental models of neuronal injury is a rise in free intracellular calcium concentration ($[Ca^{2+}]i$). Neurons possess multiple mechanisms to confine $[Ca^{2+}]_i$ to the low levels, about 100 nM, necessary for the physiological function. It is widely believed that a prolonged rise in $[Ca^{2+}]i$ deregulates tightly-controlled $Ca^{2+}$-dependent processes, causing them to yield excessive reaction products, to activate normally quiescent enzymatic pathways, or to inactivate regulatory cytoprotective mechanisms. This, in turn, results in the creation of experimentally observable measures of cell destruction, such as lipolysis, proteolysis, cytoskeletal breakdown, pH alterations and free radical formation.

The classical approach to preventing $Ca^{2+}$ neurotoxicity has been through pharmacological blockade of $Ca^{2+}$ entry through $Ca^{2+}$ channels and/or of excitatory amino acid (EAA)—gated channels. Variations on this strategy often lessen EAA—induced or anoxic cell death in vitro, lending credence to the $Ca^{2+}$-neurotoxicity hypothesis. However, a variety of $Ca^{2+}$ channel- and EAA—antagonists fail to protect against neuronal injury in vivo, particularly in experimental Spinal Cord Injury (SCI), head injury and global cerebral ischemia. It is unknown whether this is due to insufficient drug concentrations, inappropriate $Ca^{2+}$ influx blockade, or to a contribution from non-$Ca^{2+}$ dependent neurotoxic processes. It is likely that $Ca^{2+}$ neurotoxicity is triggered through different pathways in different CNS neuron types. Hence, successful $Ca^{2+}$-blockade would require a polypharmaceutical approach.

The present application contains related subject matter to applications 10/208,374 filed Jul. 30, 2002 and 09/584,555 filed May 31, 2000, the disclosures of which are hereby incorporated by reference.

SUMMARY OF THE INVENTION

I have found that postsynaptic density-95 protein (PSD-95) couples neuronal N-methyl-D-aspartate receptors (NMDARs) to pathways mediating excitotoxicity and ischemic brain damage. This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and dramatically reduced cerebral infarction volume in rats subjected to transient focal cerebral ischemia. The treatment was effective when applied either before, or one hour after, the onset of excitotoxicity in vitro and cerebral ischemia in vivo. This approach may prevent negative consequences associated with blocking NMDAR activity and constitute a practical therapy for stroke.

In accordance with certain embodiments of the present invention, a method of reducing the damaging effect of an injury to mammalian cells is provided.

In a preferred embodiment, pharmaceutical compositions are provided for use in treating mammals to reduce the damaging effect of an injury to mammalian tissue.

The present disclosure also describes the discovery of a neuroprotective effect against excitotoxic and ischemic injury by inhibiting the binding between N-methyl-D-aspartate (NMDA) receptors and neuronal proteins in a neuron.

Accordingly, certain embodiments of the invention provide a method of inhibiting the binding between N-methyl-D-aspartate receptors and neuronal proteins in a neuron, said method comprising administering to said neuron an effective inhibiting amount of a peptide replacement agent for the NMDA receptor interaction domain to effect said inhibition of the interaction with the neuronal protein.

In certain embodiments of the invention a method of inhibiting the binding between N-methyl-D-aspartate receptors and neuronal proteins in a neuron is provided. The method comprises administering to the neuron an effective inhibiting amount of a peptide replacement agent for the NMDA receptor or neuronal protein interaction domain that effect said inhibition of the NMDA receptor-neuronal protein interaction. The method is of value in reducing the damaging effect of injury to mammalian cells. Postsynaptic density-95 protein (PSD-95) couples neuronal N-methyl-D-aspartate receptors (NMDARs) to pathways mediating excitotoxicity, ischemic and traumatic brain damage. This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults, dramatically reduced cerebral infarction volume in rats subjected to transient focal cerebral ischemia, and traumatic brain injury (TBI) in rats. The treatment was effective when applied either before, or one hour after, the onset of excitotoxicity in vitro and when applied either before, one hour after or three hours after cerebral ischemia in vivo. The treatment was also effective when applied three hours after the onset of TBI in-vivo. This approach reduces negative consequences associated with blocking NMDAR activity and constitutes practical therapy for stroke or spinal cord injury.

In accordance with certain embodiments of the present invention, a method of reducing the damaging effect of ischemia or traumatic injury to the brain or spinal cord in a mammal is provided. This method comprising treating the mammal with a non-toxic, damage-reducing, effective amount of a peptide replacement agent for the NMDA receptor or neuronal protein interaction domains that inhibit the NMDA receptor neuronal protein interaction.

Damage to neurons in this specification means anoxia, ischemia, excitotoxicity, lack of neurotrophic support, disconnection, and mechanical injury.

The replacement agent for the NMDA receptor is, preferably, bindable with proteins containing PDZ domains, and most preferably, is selected from the C-terminus of NMDA receptor subunits, and, preferably, NR1, NR2A or NR2B.

The neuronal protein replacement agent for the neuronal protein interaction domains is, preferably, bindable with proteins containing the C-terminal amino acids of NMDA receptor subunits, preferably NR1, NR2A or NR2B, and is selected from PDZ domain-containing proteins and preferably the postsynaptic densityproteins PSD-95, PSD-93, SAP97, and SAP102.

I have found that the replacement agent for the NMDA receptor is a tSXV-containing peptide, preferably KLSSIESDV (SEQ. ID NO: 1).

The neuronal protein replacement agent is, preferably, bindable with excitatory amino acid receptors, and most preferably, is selected from NMDA receptor subunits NR1 and NR2.

I have found that the replacement agent is a PDZ2-domain containing polypeptide, preferably corresponding to residues 65-248 of PSD-95, encoding the first and second PDZ domains (PDZ1-2) of PSD-95.

In still other embodiments of the invention a pharmaceutical composition is provided which comprises a peptide replacement agent for the NMDA receptor or neuronal protein interaction domains that inhibit the NMDA receptor neuronal protein interaction in a mixture with a pharmaceutically acceptable carrier when used for reducing the damaging effect of an ischemic or traumatic injury to the brain or spinal cord of a mammal; preferably further comprising the cell-membrane transduction domain. A number of cell-membrane transduction domains have been described in the art as capable of facilitating the entry of a peptide linked to these cell-membrane transduction domains. Examples, of these peptides include, but are not limited to, the human immuno-deficiency virus type 1 (HIV-1) Tat protein (YGRKKRRQRRR (SEQ ID NO:3); Tat (Vives et al., 1997, *J. Biol. Chem.* 272:16010; Nagahara et al., 1998, *Nat. Med.* 4:1449)), the antennapedia internalisation peptide (Derossi et al., 1994, *J. Biol. Chem.* 261:10444), VP22 from herpes simplex virus (Elliot and D'Hara, 1997, Cell 88:223-233), complementary-determining regions $(CDR)_2$ and 3 of anti-DNA antibodies (Avrameas et al., 1998, *Proc. Natl. Acad. Sci.*, 95:5601-5606), 70 KDa heat shock protein (Fujihara, 1999, *EMBO J.* 18:411-419) transportan (Pooga et al., 1998, *FASEB J* 12:67-77), PEP-1, a 21-residue peptide carrier, Pep-1 (KETWWETWWTEWSQPKKKRKV (SEQ ID NO:8); Morris M C et al., 2001), and cationic peptides such as lysine or arginine multimers or others such as PPRLRKRRQLNM (SEQ ID NO:9), PIRRRKKLRRLK (SEQ ID NO:10), or RRQRRTSKLMKR (SEQ ID NO:11), derived from an M13 phage library (Mi et al., 2000).

In certain highly preferred embodiments of the present invention, a pharmaceutical composition comprising the peptide KLSSIESDV (SEQ ID NO:1), KLSSIETDV (SEQ ID NO:2) or residues 65-248 of PSD-95, encoding the first and second PDZ domains (PDZ1-2) of PSD-95 is provided.

In still other embodiments of the present invention, a method of inhibiting the binding between NMDA receptors and neuronal proteins in a neuron is provided. The method comprises administering to the neuron an effective inhibiting amount of an antisense DNA to prevent expression of said neuronal proteins to effect inhibition of said binding. Preferably, this embodiment provides a method wherein said antisense DNA reduces the expression of a protein containing PDZ domains bindable to said NMDA receptor. More preferably, the protein containing PDZ domains is selected from PSD-95, PSD-93, SAP-97 and SAP102.

In the mammalian nervous system, the efficiency by which N-methyl-D-aspartate receptor (NMDAR) activity triggers intracellular signaling pathways governs neuronal plasticity, development, senescence, and disease. I have studied excitotoxic NMDAR signaling by suppressing the expression of the NMDAR scaffolding protein PSD-95. In cultured cortical neurons, this selectively attenuated NMDAR excitotoxicity, but not excitotoxicity by other glutamate or $Ca^{2+}$ channels. NMDAR function was unaffected, as receptor expression, while NMDA-currents and $^{45}Ca$ loading via NMDARs were unchanged. Suppressing PSD-95 selectively blocked $Ca^{2+}$-activated nitric oxide production by NMDARs, but not by other pathways, without affecting neuronal nitric oxide synthase (nNOS) expression or function. Thus, PSD-95 is required for the efficient coupling of NMDAR activity to nitric oxide toxicity and imparts specificity to excitotoxic $Ca^{2+}$ signaling.

It is known that calcium influx through NMDARs plays key roles in mediating synaptic transmission, neuronal development, and plasticity (1). In excess, Ca influx triggers excitotoxicity (2), a process that damages neurons in neurological disorders that include stroke, epilepsy, and chronic neurodegenerative conditions (3). Rapid $Ca^{2+}$-dependent neurotoxicity is triggered most efficiently when $Ca^{2+}$ influx occurs through NMDARs, and cannot be reproduced by loading neurons with equivalent quantities of $Ca^{2+}$ through non-NMDARs or voltage-sensitive $Ca^{2+}$ channels (VSCCs) (4). This observation suggests that $Ca^{2+}$ influx through NMDAR channels is functionally coupled to neurotoxic signaling pathways.

Without being bound by theory, I believe that lethal $Ca^{2+}$ signaling by NMDARs is determined by the molecules with which they physically interact. The NR2 NMDAR subunits, through their intracellular C-terminal domains, bind to PSD-95/SAP90 (5), chapsyn-110/PSD-93, and other members of the membrane-associated guanylate kinase (MAGUK) family (6). NMDAR-bound MAGUKs are generally distinct from those associated with non-NMDARs (7). I have found that the preferential activation of neurotoxic $Ca^{2+}$ signals by NMDARs is determined by the distinctiveness of NMDAR-bound MAGUKs, or of the intracellular proteins that they bind. PSD-95 is a submembrane scaffolding molecule that binds and clusters NMDARs preferentially and, through additional protein-protein interactions, may link them to intracellular signali-ng molecules (8). Perturbing PSD-95 would impact on neurotoxic $Ca^{2+}$ signaling through NMDARs.

Thus, protein-protein interactions govern the signals involved in cell growth, differentiation, and intercellular communication through dynamic associations between modular protein domains and their cognate binding partners (20). At excitatory synapses of central neurons, ionotropic glutamate receptors are organized into multi-protein signaling complexes within the post-synaptic density (PSD) (21). A prominent organizing protein within the PSD is PSD-95, a member of the membrane-associated guanylate kinase (MAGUK) family. PSD-95 contains multiple domains that couple transmembrane proteins such as the N-methyl-D-aspartate subtype of glutamate receptors (NMDAR) to a variety of intracellular signaling enzymes (21, 22). Through its second PDZ domain (PDZ2), PSD-95 binds both the NMDAR 2B subunit (NR2B) and neuronal nitric oxide synthase (nNOS) (22). This interaction couples NMDAR activity to the production of nitric oxide (NO), a signaling molecule that mediates NMDAR-dependent excitotoxicity (23). Research has shown that NMDAR function is unaffected by genetically disrupting PSD-95 in vivo (24) or by suppressing its expression in vitro (25). Nonetheless, PSD-95 deletion dissociates NMDAR activity from NO production and suppresses NMDAR-dependent excitotoxicity.

Although NMDARs play an important neurotoxic role in hypoxic/ischemic brain injury (26), blocking NMDAR function may be deleterious in animals and humans (27-29). Targeting PSD-95 protein therefore represents an alternative therapeutic approach for diseases that involve excitotoxicity that may circumvent the negative consequences of blocking NMDAR function. However, mutation or suppression of PSD-95 is impractical as a therapy for brain injury and cannot be applied after an injury has occurred. Therefore, rather than alter PSD-95 expression, I questioned whether interfering with the NMDAR/PSD-95 interaction could suppress excitotoxicity in vitro and ischemic brain damage in vivo.

BRIEF DESCRIPTION OF THE DRAWINGS

In order that the invention may be better understood, preferred embodiments will now be described by way of example only with reference to the accompanying drawings wherein:

FIGS. 2a1-b2 represent bar charts of selective activations of AMPA/Kainate receptors with Kainate (2a1 and 2-a2); and loadings with Vscc's (2-b1) and calcium loading (2-b2).

DETAILED DESCRIPTION OF PREFERRED EMBODIMENTS

Figure 1A:
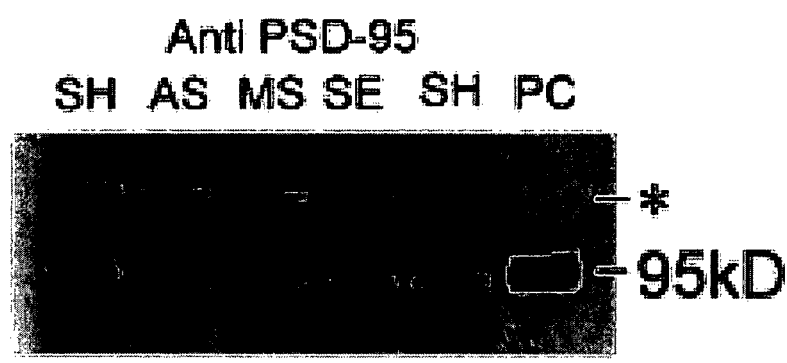
FIG. 1a is an immunublot.
Figure 1B:
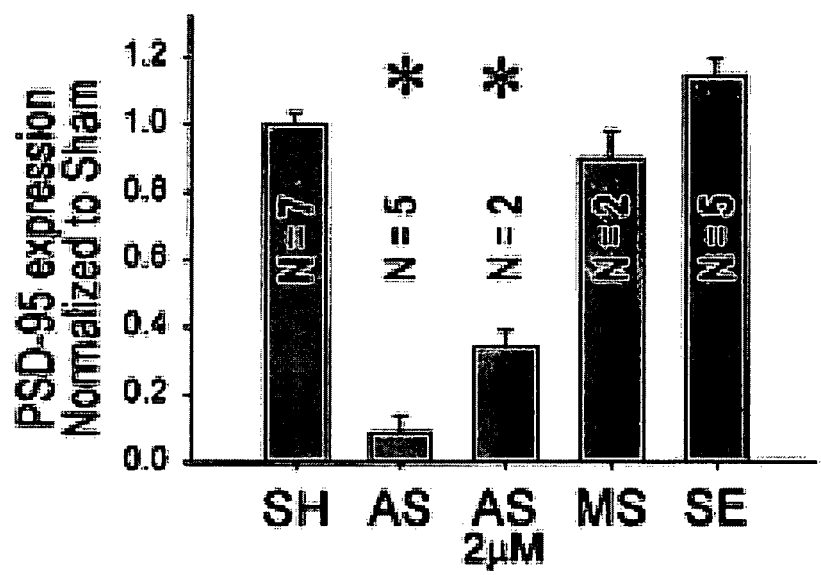
FIG. 1b is a bar chart providing densitometric analysis of PSD-95 expression.

Cultured cortical neurons were prepared by standard techniques (4,9) and switched to serum-free media at 24 h [Neurobasal with B27 supplement (Gibco)]. The AS ODN corresponded to nucleotides 435-449 of mouse PSD-95/SAP90 mRNA (GeneBank Acc. No. D50621). Filter-sterilized phosphodiester AS SE, and MS ODNs (5 µM) were added in culture medium during feedings at 4, 6, 8 and 10 days after plating. Cultures were used for all experiments (FIGS. 1-4) on day 12. ODN sequences exhibited no similarity to any other known mammalian genes (BLAST search (10)).

Immunoblotting was done as described in ref. "26". Tissue was harvested and pooled from 2 cultures/lane. The blotted proteins were probed using a monoclonal anti-PSD-95 mouse IgG1 (Transduction Labs, 1:250 dilution), polyclonal anti PSD-93 (1:1000 dilution) and anti SAP-102 (1:2000 dilution) rabbit serum antibodies (Synaptic Systems GmbH), a monoclonal anti NR1 mouse IgG2a (PharMingen Canada, 1:1000 dilution) or a monoclonal anti NNOS(NOS type I) mouse IgG2a (Transduction Labs, 1:2500 dilution). Secondary antibodies were sheep anti-mouse, or donkey anti-rabbit Ig conjugated to horseradish peroxidase (Amersham). Immunoblots for PSD-95 were obtained for all experiments (FIGS. 1-4) from sister cultures, and all gels quantified using an imaging densitometer (Bio-Rad GS-670).

cGMP determinations were performed 10 min after challenging the cultures with NMDA, kainate, or high-K (FIGS. 4c-e) with the Biotrak cGMP enzymeimmunoassay system according to the kit manufacturer's instructions (Amersham). Staining for NADPH diaphorase (FIG. 4b) was done as described in ref. 12.

Whole cell patch-clamp recordings in the cultured neurons were performed and analyzed as described in ref. 13. During each experiment a voltage step of −10 mV was applied from holding potential and the cell capacitance was calculated by integrating the capacitative transient. The extracellular solution contained (in mM): 140 NaCl, 5.4 KCl, 1.3 $CaCl_2$, 25 HEPES, 33 glucose, 0.01 glycine, and 0.001 tetrodotoxin (pH=7.3-7.4, 320-335 mOsm). A multi-barrel perfusion system was employed to rapidly exchange NMDA containing solutions. The pipette solution contained (in mM): 140 CsF, 35 CsOH, 10 HEPES, 11 EGTA, 2 tetraethylammonium chloride (TEA), 1 $CaCl_2$, 4 MgATP, pH 7.3 at 300 mOsm. Lucifer yellow (LY; 0.5% w/v) was included in the pipette for experiments in FIG. 3d.

Excitotoxicity and $Ca^{2+}$ accumulation measurements were performed identically to the methods described and validated in refs. 4 and 14. I used measurements of propidium iodide fluorescence as an index of cell death, and of radiolabelled $^{45}Ca^{2+}$ accumulation for $Ca^{2+}$ load determinations in sister cultures on the same day. Experimental solutions were as previously described (4). $Ca^{2+}$ influx was pharmacologically channeled through distinct pathways as follows: To NMDARs by applying NMDA (×60 min) in the presence of both CNQX (Research Biochemicals Inc.) and nimodipine (Miles Pharmaceuticals), to non-NMDARs by applying kainic acid (×60 min or 24 h) in the presence of both MK-801 (RBI) and nimodipine, and to VSCCs using 50 mM $K^+$ solution (×60 min) containing 10 mM $Ca^{2+}$ and S(−)-Bay K 8644, an L-type channel agonist (300-500 nM; RBI), MK-801 and CNQX. Antagonist concentrations were (in µM): MK-801 10, CNQX 10, nimodipine 2. All three antagonists were added after the 60 min agonist applications for the remainder of all experiments (24 h). A validation of this approach in isolating $Ca^{2+}$ influx to the desired pathway in these cortical cultures has been published (4).

Whole cell patch-clamp recordings in the cultured neurons were performed and analyzed as described in Z. Xiong, W. Lu, J. F. MacDonald, *Proc Natl Acad Sci USA* 94, 7012 (1997). During each experiment a voltage step of −10 mV was applied from holding potential and the cell capacitance was calculated by integrating the capacitative transient. The extracellular solution contained (in mM): 140 NaCl, 5.4 KCl, 1.3 $CaCl_2$, 25 HEPES, 33 glucose, 0.01 glycine, and 0.001 tetrodotoxin (pH=7.3-7.4, 320-335 mOsm). A multi-barrel perfusion system was employed to rapidly exchange NMDA containing solutions. The pipette solution contained (in mM): 140 CsF, 35 CsOH, 10 HEPES, 11 EGTA, 2 tetraethylammonium chloride (TEA), 1 $CaCl_2$, 4 MgATP, pH 7.3 at 300 mOsm. Lucifer yellow (LY; 0.5% w/v) was included in the pipette for experiments in FIG. 3D.

Data analysis: data in all figures were analyzed by ANOVA, with a post-hoc Student's t-test using the Bonferroni correction for multiple comparisons. All means are presented with their standard errors.

In Greater Detail:

FIG. 1 shows increased resilience of PSD-95 deficient neurons to NMDA toxicity in spite of $Ca^{2+}$ loading. A. Immunoblot showing representative effects of sham (SH) washes, and PSD-95 AS, SE and MS ODNs, on PSD-95 expression. PC: positive control tissue from purified rat brain cell membranes. Asterisk: non-specific band produced by the secondary antibody, useful to control for protein loading and blot exposure times. B. Densitometric analysis of PSD-95 expression pooled from N experiments. Asterisk: different from other groups, one-way ANOVA, F=102, p<0.0001. ODNs were used at 5 µM except where indicated (AS 2 µM). C. Representative phase contrast and propidium iodide fluorescence images of PSD-95 deficient (AS) and control (SE) cultures 24 h after a 60 min challenge with 30 µM NMDA. Scale bar: 100 µM. D. Decreased NMDA toxicity at 24 h in PSD-95 deficient neurons following selective NMDAR activation ×60 min (n=16 cultures/bar pooled from N=4 separate experiments). Asterisk: differences from SE, MS and SH (Bonferroni t-test, p<0.005). Death is expressed as the fraction of dead cells produced by 100 µM NMDA in sham-ODN-treated controls (validated in 4,14). E. No effect of PSD-95 deficiency on NMDAR-mediated $Ca^{2+}$ loading (n=12/bar, N=3; reported as the fraction of $^{45}Ca^{2+}$ accumulation achievable over 60 min in the sham controls by 100 µM NMDA, which maximally loads the cells with calcium (4).

FIG. 2 shows that PSD-95 deficiency does not affect toxicity and $Ca^{2+}$ loading produced by activating non-NMDARs and $Ca^{2+}$ channels. Cultures were treated with SH washes or AS or SE ODNs as in FIG. 1. A. Selective activation of AMPA/kainate receptors with kainate in MK-801 (10 µM) and nimodipine (NIM; 2 µM) produces toxicity over 24 h (A1) irrespective of PSD-95 deficiency, with minimal $^{45}Ca^{2+}$ loading (A2). B. Selective activation of VSCCs produces little toxicity (B1), but significant $^{45}Ca^{2+}$ loading (B2) that is also insensitive to PSD-95 deficiency. n=4 cultures/bar in all experiments.

FIG. 3 shows that there is no effect of perturbing PSD-95 on receptor function. A. Immunoblots of PSD-95 ODN-treated cultures probed for PSD-95, NR1, PSD-93, and SAP-102 using specific antibodies. PC: positive control tissue from purified rat brain cell membranes. B. NMDA dose-response curves and representative NMDA currents (inset) obtained with 3-300 μM NMDA. C. NMDA current density measurements elicited with 300 μM NMDA (AS: n=18; SE: n=19; SH: n=17; one-way ANOVA F=1.10, p=0.34), and analysis of NMDA current desensitization. $I_{ss}$=steady-state current; $I_{peak}$=peak current. AS: n=15; SE: n=16; SH: n=16 (ANOVA, F=0.14, p=0.87). Time constants for current decay were AS: 1310±158 ms; SE, 1530±185 ms; SH: 1190±124 ms (ANOVA, F=1.22, p=0.31). D. Currents elicited with 300 PM NMDA in neurons dialyzed with LY (insert) and 1 mM tSXV or control peptide.

FIG. 4 shows the effect of coupling of NMDAR activation to nitric oxide signaling by PSD-95. A. L-NAME protects against NMDA toxicity (n=4, N=2). Asterisk: difference from 0 μM L-NAME (Bonferroni t-test, p<0.05). B. No effect of SH and of PSD-95 AS and MS ODNs on NNOS expression in cultures (immunoblot) and on NADPH diaphorase staining in PSD-95 AS and SE-treated neurons. PC: positive control tissue from purified rat brain cell membranes. C. Effect of isolated NMDAR activation on cGMP formation (n=12 cultures/bar pooled from N=3 separate experiments) D,E. Effects of VSCC activation (n=8/bar, N=2), and AMPA/kainate receptor activation (n=4/bar, N=1) on cGMP formation. Data in C-E are expressed as the fraction of cGMP produced in SE-treated cultures by 100 μM NMDA. Asterisk: differences from both SH and SE controls (Bonferroni t-test, p<0.0001). F. Sodium nitroprusside toxicity is similar in PSD-95 AS, SE and SH treated cultures.

PSD-95 expression was suppressed in cultured cortical neurons to <10% of control levels, using a 15-mer phosphodiester antisense (AS) oligodeoxynucleotide (ODN) (FIG. 1A,B) Sham (SH) washes, sense (SE) and missense (MS) ODNs (9) had no effect. The ODNs had no effect on neuronal survivability and morphology as gauged by viability assays, herein below, and phase-contrast microscopy (not shown).

Figure 1C:
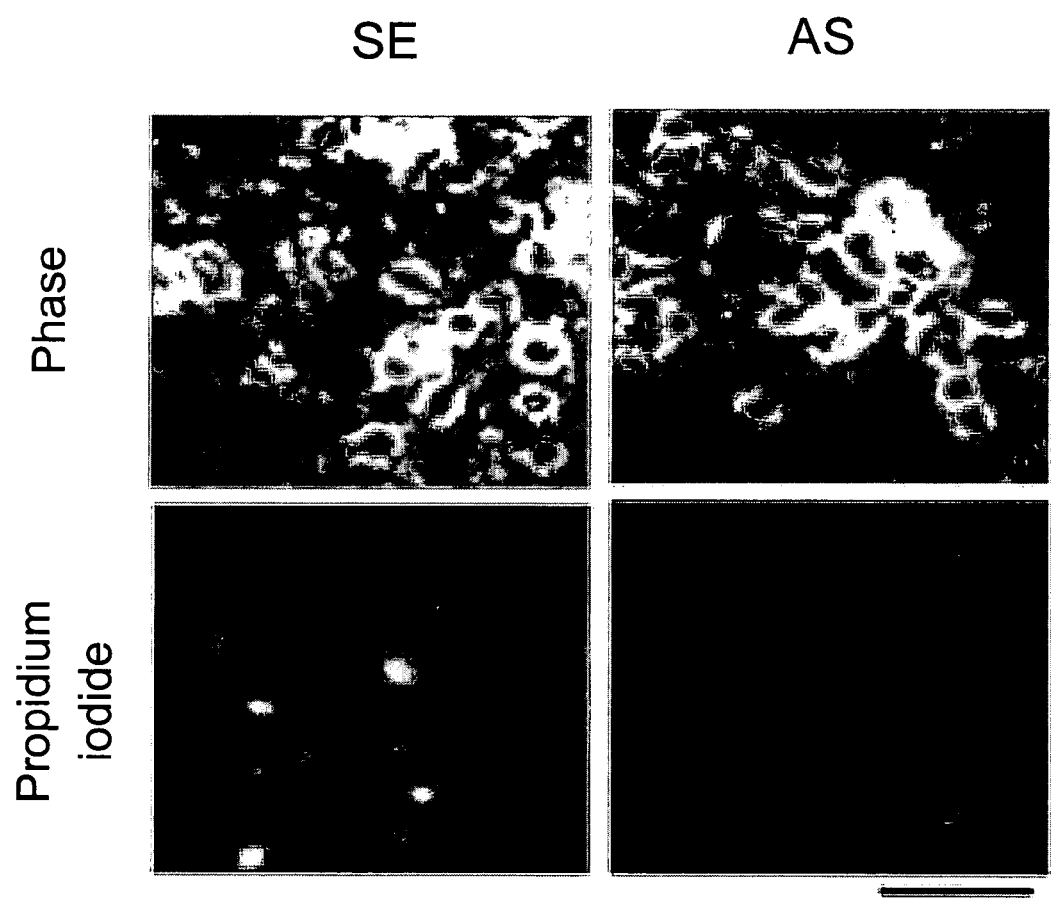
FIG. 1c represents representative phase contrast and propidium fluorescence images.
Figures 1D, 1E:
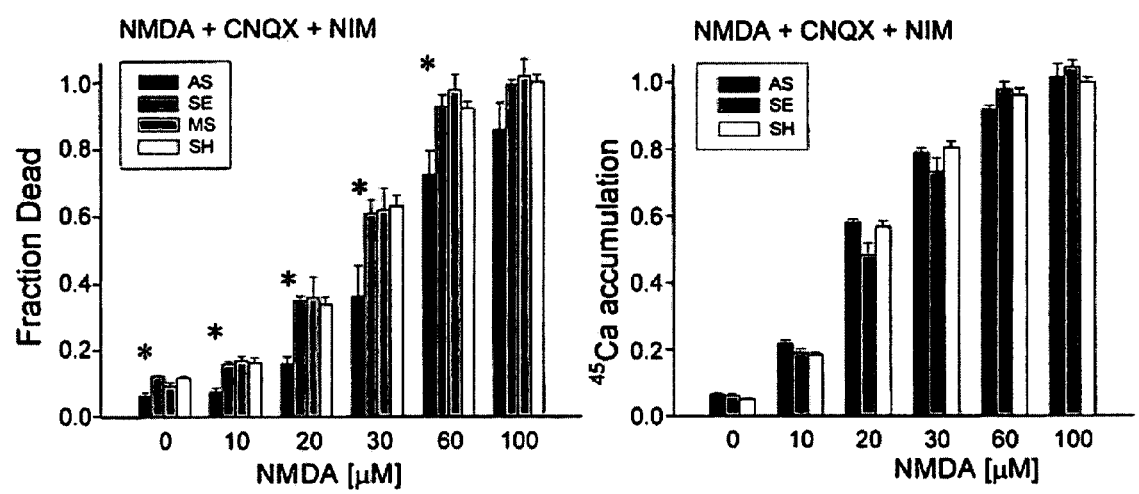
FIG. 1d is a bar chart of NMDA concentration against fraction of dead cells.
FIG. 1e is a bar chart of NMDA concentration against Calcium accumulation.

To examine the impact of PSD-95 on NMDAR-triggered excitotoxicity, ODN-treated cultures were exposed to NMDA (10-100 μM) for 60 min, washed, and either used for $^{45}Ca^{2+}$ accumulation measurements, or observed for a further 23 h $Ca^{2+}$ influx was isolated to NMDARs by adding antagonists of non-NMDARs and $Ca^{2+}$ channels (4). NMDA toxicity was significantly reduced in neurons deficient in PSD-95 across a range of insult severities (FIGS. 1C,D; $EC_{50}$: AS: 43.2±4.3; SE: 26.3±3.4, Bonferroni t-test, p<0.005). Concomitantly however, PSD-95 deficiency had no effect on $Ca^{2+}$ loading into identically treated sister cultures (FIG. 1E). Therefore, PSD-95 deficiency induces resilience to NMDA toxicity despite maintained $Ca^{2+}$ loading.

I next examined whether the increased resilience to $Ca^{2+}$ loading in PSD-95 deficient neurons was specific to NMDARs. Non-NMDAR toxicity was produced using kainic acid (30-300 μM), a non-desensitizing AMPA/kainate receptor agonist (15), in the presence of NMDAR and $Ca^{2+}$ channel antagonists (4). Kainate toxicity was unaffected in PSD-95 deficient in neurons challenged for either 60 min (not shown) or 24 h (FIG. 2A1). Non-NMDAR toxicity occurred without significant $^{45}Ca^{2+}$ loading (FIG. 2A2), as >92% of neurons in these cultures express $Ca^{2+}$-impermeable AMPA receptors (4). However, $Ca^{2+}$ loading through VSCCs, which is non-toxic (4) (FIG. 2B1), was also unaffected by PSD-95 deficiency (FIG. 2B2). Thus, suppressing PSD-95 expression affects neither toxicity nor $Ca^{2+}$ fluxes triggered through pathways other than NMDARs.

Figure 3A:
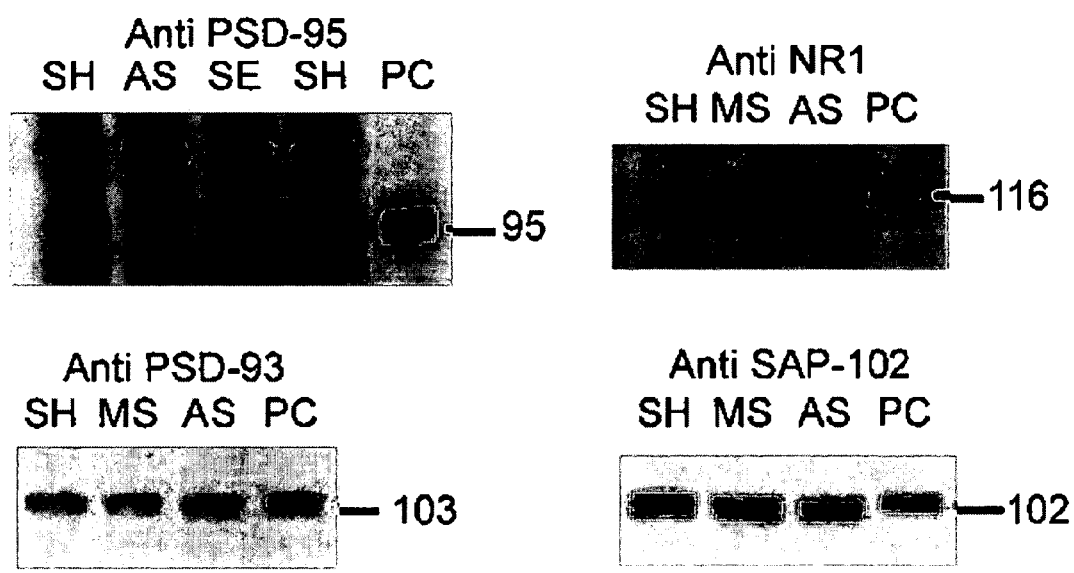
FIGS. 3a-d represent immunoblots (3a); NMDA dose-response curves (3b); NMDA current density measurements (3c); and current/time graph (3d) dialyzed with lucifer yellow.
Figure 3B:
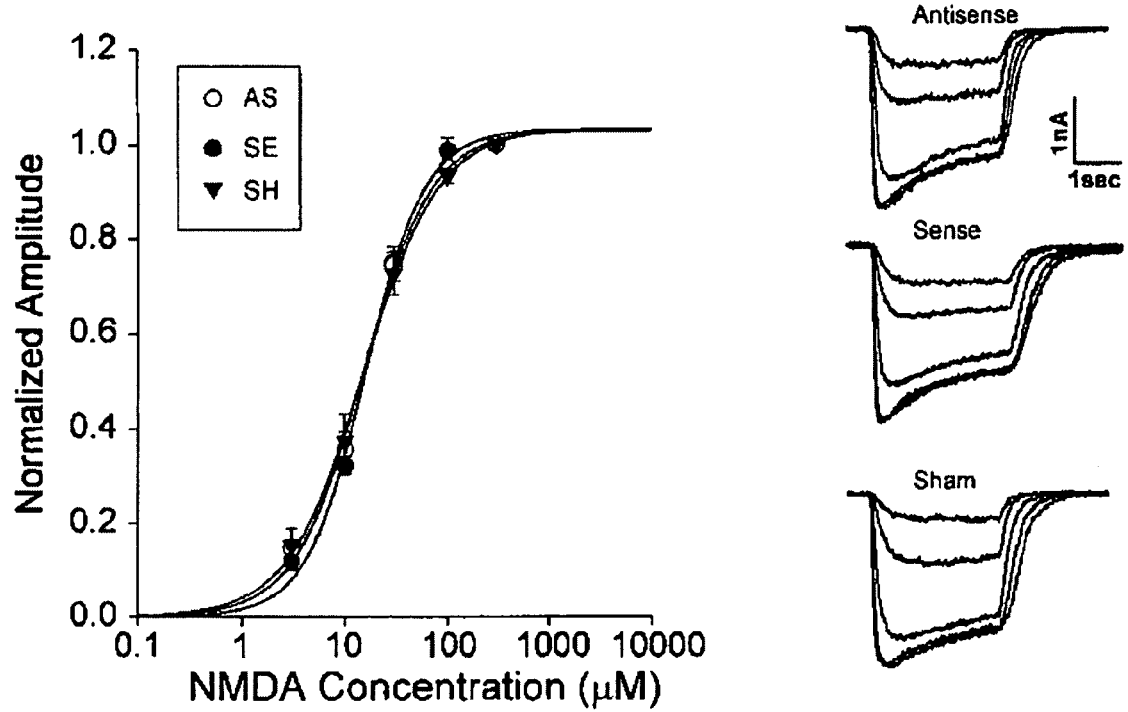
Figure 3C:
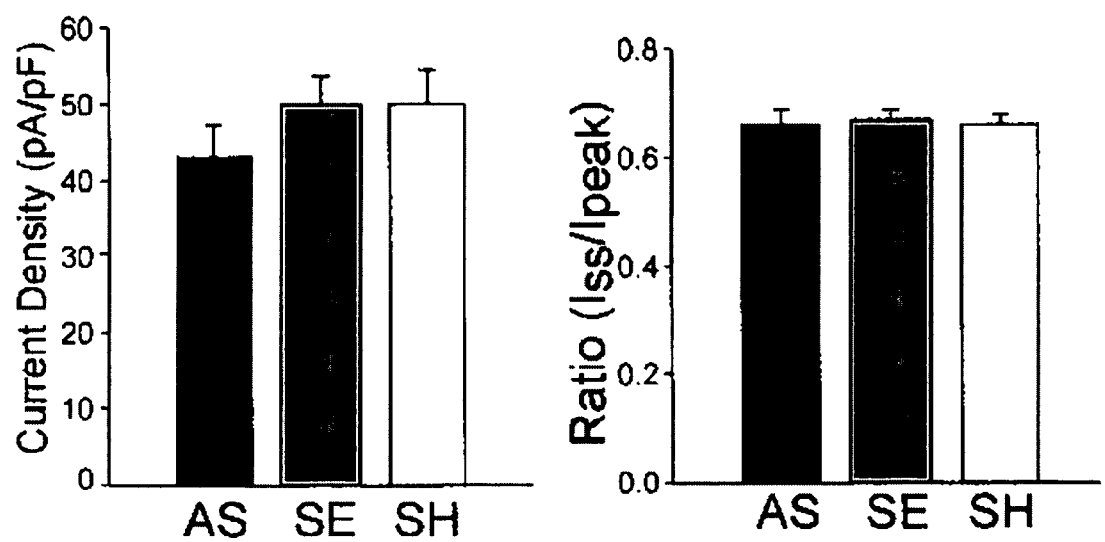

Immunoblot analysis (11) of PSD-95 deficient cultures revealed no alterations in the expression of the essential NMDAR subunit NR1, nor of two other NMDAR-associated MAGUKs, PSD-93 and SAP-102 (FIG. 3A). This indicated that altered expression of NMDARs and their associated proteins was unlikely to explain reduced NMDA toxicity in PSD-95 deficiency (FIG. 1C,D). Therefore, I examined the possibility that PSD-95 modulates NMDAR function. NMDA currents were recorded using the whole-cell patch technique (16) (FIG. 3B). PSD-95 deficiency had no effect on passive membrane properties, including input resistance and membrane capacitance [Capacitance: AS 55.0±2.6 pF (n=18); SE 52.7±3.2 pF (n=19); SH 48.1±3.4 pF (n=17; ANOVA, F=1.29, p=0.28)]. Whole-cell currents elicited with 3-300 μM NMDA were also unaffected. Peak currents were AS: 2340±255 pA (n=18); SE: 2630±276 (n=19); SH: 2370±223 (n=17) (FIG. 3B, inset; one-way ANOVA, F=0.43, p=0.65). NMDA dose-response relationships also remained unchanged (FIG. 3B; $EC_{50}$ AS: 16.1±0.8 μM (n=7); SE: 15.5±2.1 (n=6); SH: 15.9±2.9; one-way ANOVA, F=0.02, p=0.98), as were NMDA current density and desensitization (FIG. 3C).

Figure 3D:
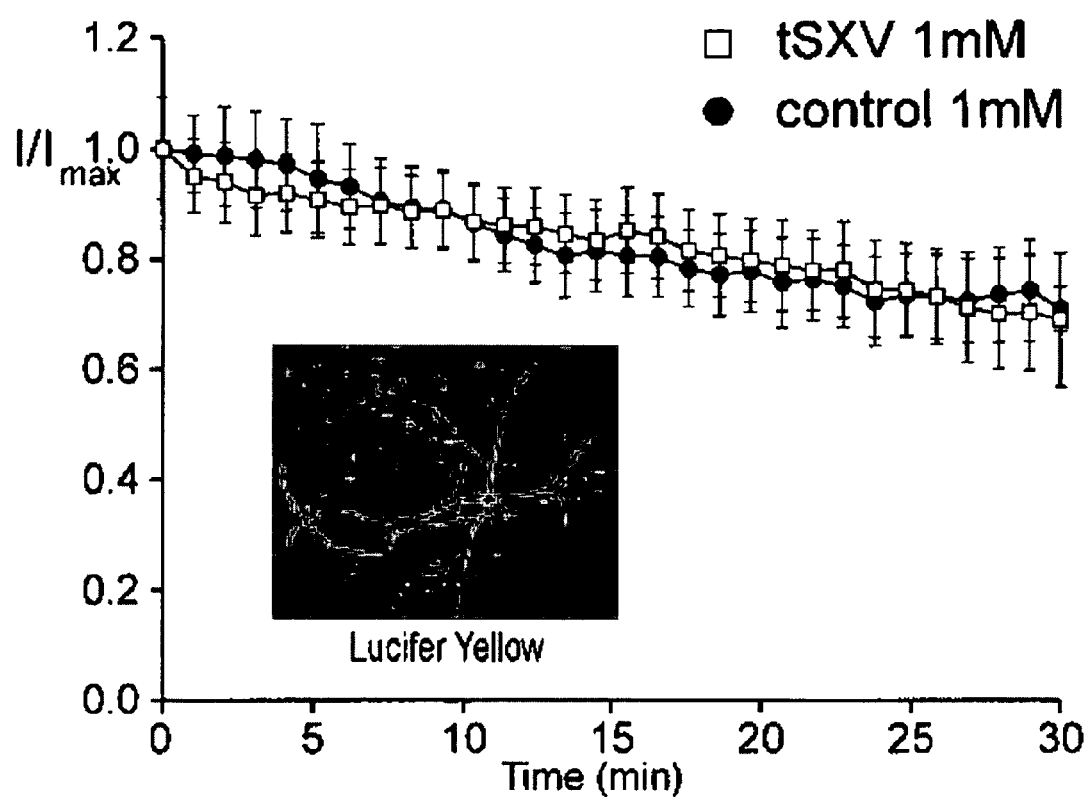

To further examine the effect of PSD-95 binding on NMDAR function, a 9 aa peptide, KLSSIESDV (SEQ ID NO:1) corresponding to the C-terminal domain of the NR2B subunit characterized by the tSXV motif (6) was injected into the neurons. At 0.5 mM, this peptide competitively inhibited the binding of PSD-95 to GST-NR2B fusion proteins (6), and was therefore predicted to uncouple NMDARs from PSD-95. Intracellular dialysis of 1 mM tSXV or control peptide, CSKDTMEKSESL (SEQ ID NO:6) (6) was achieved through patch pipettes (3-5 MΩ) also containing the fluorescent tracer Lucifer Yellow (LY). This had no effect on NMDA currents over 30 min despite extensive dialysis of LY into the cell soma and dendrites (FIG. 3D). Peak current amplitudes were tSXV: 2660±257 pA (n=9), control: 2540±281 pA (n=10; $t_{17}$)=0.31, p=0.76).

The data is consistent with that obtained from recently generated mutant mice expressing a truncated 40K PSD-95 protein that exhibited enhanced LTP and impaired learning (17). Hippocampal CA1 neurons in PSD-95 mutants exhibited no changes in NMDAR subunit expression and stoichiometry, cell density, dendritic cytoarchitecture, synaptic morphology, or NMDAR localization using NR1 immunogold labeling of asymmetric synapses. NMDA currents, including synaptic currents, were also unchanged (16). I also found no effects of PSD-95 deficiency on NMDAR expression, on other NMDAR associated MAGUKs, nor on NMDA-evoked currents. In addition, NMDAR function gauged by measuring NMDA-evoked $^{45}Ca^{2+}$-accumulation was unaffected. Thus, the neuroprotective consequences of PSD-95 deficiency must be due to events downstream from NMDAR activation, rather than to altered NMDAR function.

The second PDZ domain of PSD-95 binds to the C-terminus of NR2 subunits and to other intracellular proteins (8). Among these is NNOS (18), an enzyme that catalyzes the production of nitric oxide (NO), a short-lived signaling molecule that also mediates $Ca^{2+}$-dependent NMDA toxicity in cortical neurons (12). Although never demonstrated experimentally, the NMDAR/PSD-95/nNOS complex was postulated to account for the preferential production of NO by NMDARs over other pathways (8). To determine whether NO signaling plays a role in NMDA toxicity in the present cultures, I treated the cells with $N^G$-nitro-L-arginine methyl ester (L-NAME), a NOS inhibitor (12). L-NAME protected the neurons against NMDA toxicity (FIG. 4A), indicating the possibility that suppressing PSD-95 might perturb this toxic signaling pathway.

Figure 4A:
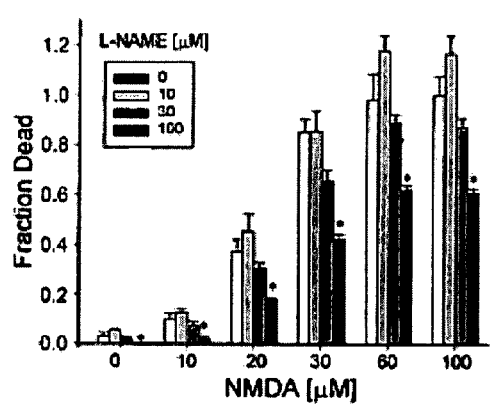
FIG. 4 bar charts (4a; 4c-4f) and immunoblot 4b of effect on nNOS expression in cultures are hereinafter better described and explained.
Figure 4B:
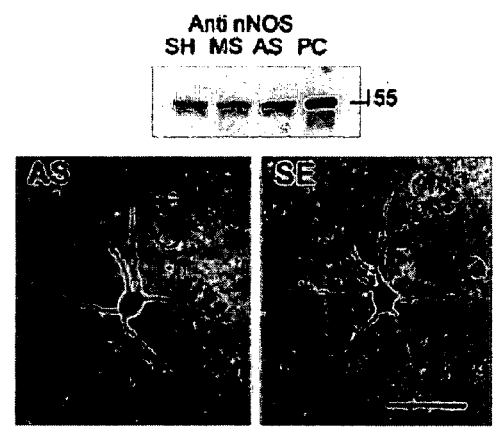
Figure 4E:
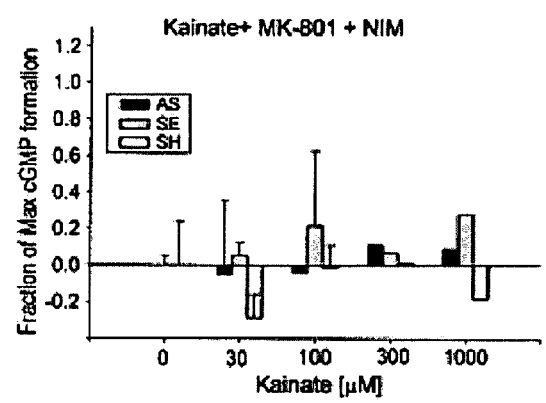

The effect of suppressing PSD-95 expression on NO signaling and toxicity was examined using cGMP formation as a surrogate measure of NO production by $Ca^{2+}$-activated NNOS (20,21). PSD-95 deficiency had no impact on nNOS expression (FIG. 4B), nor on the morphology (FIG. 4B) or counts of NADPH diaphorase-staining (12) neurons (SH: 361±60, SE: 354±54, AS: 332±42 staining neurons/10 mm coverslip, 3 coverslips/group). However, in neurons lacking PSD-95 challenged with NMDA under conditions that isolated $Ca^{2+}$ influx to NMDARs (4), cGMP production was markedly attenuated (>60%; FIG. 4C, one-way ANOVA, $p<0.0001$). Like inhibited toxicity (FIGS. 1,2), inhibited cGMP formation in neurons lacking PSD-95 was only observed in response to NMDA. It was unaffected in neurons loaded with $Ca^{2+}$ through VSCCs (FIG. 4D), even under high neuronal $Ca^{2+}$ loads matching those attained by activating NMDARs (compare FIGS. 1E and 2B2) (4). NNOS function therefore, was unaffected by PSD-95 deficiency. AMPA/kainate receptor activation failed to load the cells with $Ca^{2+}$ (FIG. 2A2), and thus failed to increase cGMP levels (FIG. 4E). These findings indicate that suppressing PSD-95 selectively reduces NO production efficiency by NMDAR-mediated $Ca^{2+}$ influx, but preserves NO production by $Ca^{2+}$ influx through other pathways.

Bypassing nNOS activation with NO donors restored toxicity in neurons lacking PSD-95. The NO donors sodium nitroprosside (12) (FIG. 4F; $EC_{50}$ 300 µM) and S-nitrosocysteine (17) (not shown) were highly toxic, irrespective of PSD-95 deficiency. Thus, reduced NMDA toxicity in PSD-95 deficient cells was unlikely to be caused by altered signaling events downstream from NO formation.

Figure 4F:
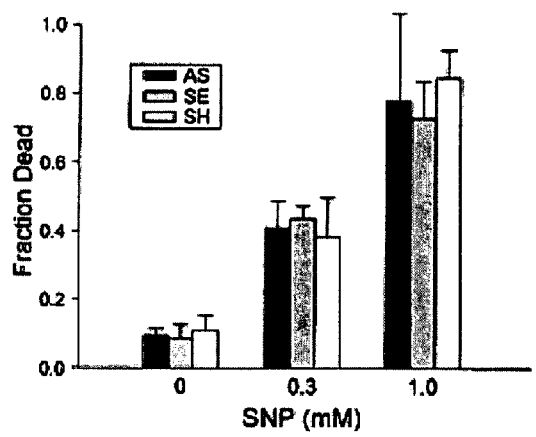

Suppressing PSD-95 expression uncoupled NO formation from NMDAR activation (FIG. 4C), and protected neurons against NMDAR toxicity (FIG. 1C,D) without affecting receptor function (FIGS. 1E, 3A-D), by mechanisms downstream from NMDAR activation, and upstream from NO-mediated toxic events (FIG. 4F). Therefore, PSD-95 imparts NMDARs with signaling and neurotoxic specificity through the coupling of receptor activity to critical second messenger pathways. These results have broader consequences, as NMDAR activation and NO signaling are also critical to neuronal plasticity, learning, memory, and behavior (1, 18,19). Thus, these data provide experimental evidence for a mechanism by which PSD-95 protein may govern important physiological and pathological aspects of neuronal functioning.

FIG. 5 shows the utility of Tat-peptides in dissociating the NMDAR/PSD-95 interaction (A) The hypothesis: The NMDAR/PSD-95 complex (left panel) may be dissociated using Tat peptides fused either to the C-terminus of NR2B (Tat-NR2B9c; middle) or to the first and second PDZ domains of PSD-95 (pTat-PDZ1-2; right), thus reducing the efficiency of excitotoxic signaling via $Ca^{2+}$-dependent signaling molecules (B) Intracellular accumulation of Tat-NR2B9c-dansyl (10 µM) but not control peptide (Tat-38-48-dansyl; 10 µM) was observed 30 min after application to cortical neuronal cultures using confocal microscopy (excitation: 360 nm, emission: >510 nm; representative of 5 experiments). Fluorescence of cultures treated with Tat-38-48-dansyl was similar to background (not shown). (C) Time course of Tat-NR2B9c-dansyl (10 µM) fluorescence after application to cortical cultures at room temperature (symbols: mean±S.E of 4 experiments). Inset: fluorescence images from representative experiment (D) Tat-NR2B9c, but not control peptides (see text), inhibits the co-immunoprecipitation of PSD-95 with NR2B in rat forebrain lysates (Left: Representative gel; Right: means±S.E of 4 experiments, ANOVA, F=6.086, * p=0.0041).

Figure 5A:
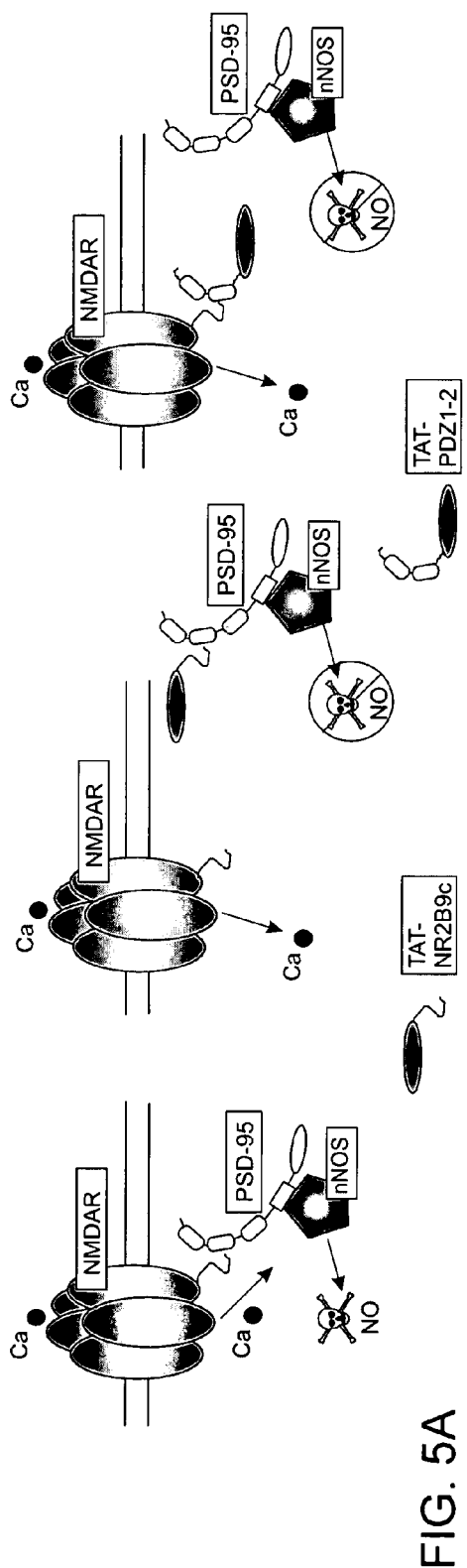
FIG. 5. (A) Shows the hypothesis: The NMDAR/PSD-95 complex may be dissociated by peptides encoding either to the C-terminus of NR2 or the second PDZ domains of PSD-95 (B) Fluorescence of cultures treated with Tat-38-48-dansyl and Tat-NR2B9c dansyl. (C) Time course fluorescence after Tat-NR2B9c-dansyl application (D) Effect of peptides on co-immunoprecipitation of PSD-95 with NR2B.

In more detail, a conserved tSXV motif at the C-terminus of the NR2B subunit is critical for binding to the PDZ2 domain of PSD-95. I hypothesized that interfering with this interaction might disrupt the coupling between NMDARs and PSD-95. This might be achieved by the intracellular introduction of exogenous peptides that bind to either the NR2B or the PDZ2 interaction domains (FIG. 5A). To this end I used a peptide comprised of the nine C-terminal residues of NR2B (KLSSIEESDV; NR2B9c (SEQ ID NO:1)), which is anticipated to bind the PDZ2 domain of PSD-95. As an alternative means to interfere with the NMDAR/PSD-95 interaction I constructed a protein comprised of residues 65-248 of PSD-95 encompassing the first and second PDZ domains (PDZ1-2), which contains the principal binding domain in PSD-95 for the C-terminus of NR2B. NR2B9c or PDZ1-2 on their own did not enter cells (not shown) and therefore, I fused each to a peptide corresponding to the cell-membrane transduction domain of the HIV-1-Tat protein (YGRKKRRQRRR (SEQ ID NO:3); Tat) to obtain a 20 amino acid peptide (Tat-NR2B9c) and the fusion protein pTat-PDZ1-2. pTat-PDZ1-2 and pTat-GK fusion proteins were generated by insertion of PSD95 residues 65-248 encoding the PDZ 1 and 2, and residues 534-724 encoding the guanylate kinase-like domains, respectively, into pTAT-HA plasmids (generous gift of S. Dowdy, Washington University, St. Louis, Mo.). Fusion proteins contain a 6×His-tag, the protein transduction domain of HIV-1 Tat and a hemagglutinin-tag N-terminal to the insert. Plasmids were transformed into BL21(DE3)LysS bacteria (Invitrogen) and recombinant proteins were isolated under denaturing conditions on a Nickle-His column (Amersham-Pharmacia). These are anticipated to transduce cell membranes in a rapid, dose-dependent manner independent of receptors and transporters (30).

To determine whether Tat-NR2B9c was able to transduce into neurons, I conjugated the fluorophore dansyl chloride to Tat-NR2B9c and to a control peptide comprised of HIV-1-Tat residues 38-48 (KALGISYGRKK (SEQ ID NO:7); Tat38-48) outside the Tat transduction domain (31).

Electrophysiological Recordings were made in 400 µM hippocampal slices from 20-36 day old Sprague-Dawley rats perfused at room temperature with ACSF containing (in mM) 126 NaCl, 3 KCl, 2 $MgCl_2$, 2 $CaCl_2$, 1.2 $KH_2PO_4$, 26 $NaHCO_3$ and 10 glucose and bubbled with 95% $O_2$/5% $CO_2$. Whole-cell recordings of CA1 neurons were performed using the "blind" method with an Axopatch-1D amplifier (Axon Instruments, Foster City, Calif.) at holding potential –60 mV. Pipettes (4-5 MΩ) were filled with solution containing (mM): 135 CsCl, 2 $MgCl_2$, 0.1 $CaCl_2$, 0.5 EGTA, 10 HEPES, 4 Mg-ATP, 0.2 GTP, and 5 QX-314, pH 7.4, 310 mOsm. Field potentials were recorded with glass micropipettes (2-4 MΩ) filled with ACSF placed in the stratum radiatum 60-80 µM from the cell body layer. Synaptic responses were evoked by stimulation (0.05 ms) of the Schaffer collateral-commissural pathway with a bipolar tungsten electrode in the presence of bicuculline methiodide (10 µM). For $I_{NMDA}$ recording, $Mg^{2+}$ was removed from and 20 µM CNQX was added in ACSF. Following 10-20 min base line recordings of EPSCs, $I_{NMDA}$ and fEPSPs, Tat-peptides were applied in ACSF and recordings were continued for 30 min thereafter.

Figure 5B:
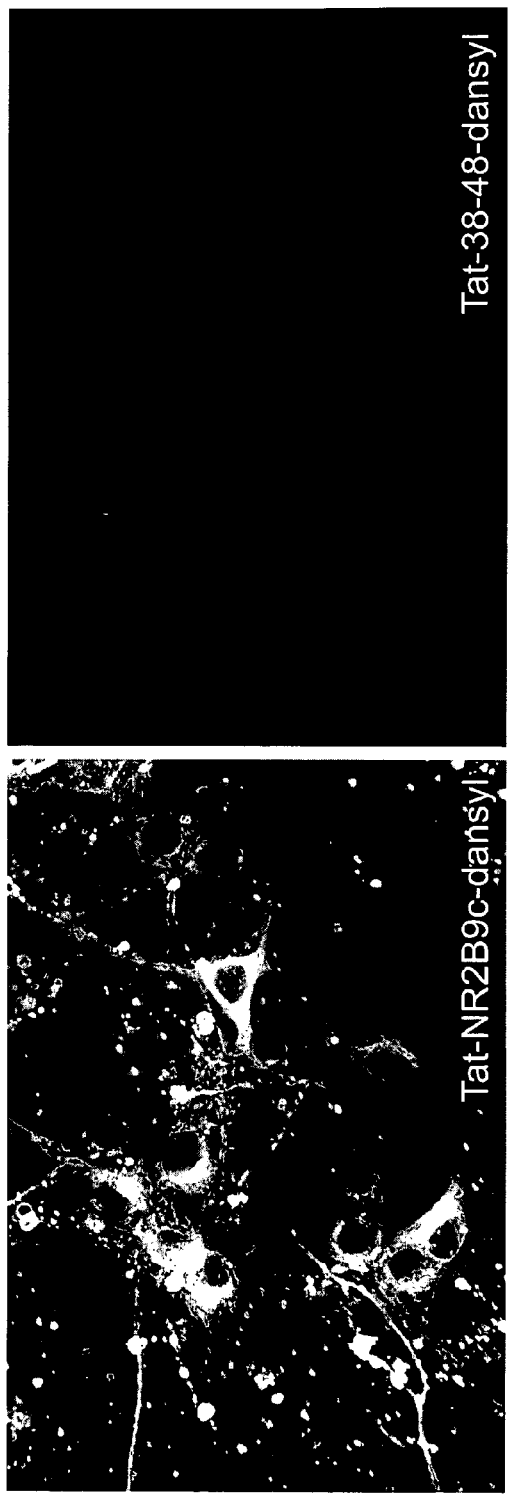

I bath applied these to cultured cortical neurons and observed their fluorescence by confocal microscopy. Neurons treated with Tat-NR2B9c-dansyl (10 µM) exhibited fluorescence in their cytoplasm and processes, indicating intracellular peptide delivery (FIG. 5B, left). Sister cultures treated with Tat38-48-dansyl (10 µM) exhibited only background fluorescence, indicating no observable peptide uptake in the absence of the Tat transduction domain (FIG. 5B, right). Tat-NR2B9c-dansyl was detectable in the neurons within 10 min of the start of the application and the peptide accumulated to a maximum level over the next 20 min (FIG. 5C). This level was maintained until the dansyl-Tat-NR2B9c was washed from the bath and the peptide remained detectable within the neurons for more than 5 hours thereafter. Therefore, the Tat transduction domain was able to act as a carrier for NR2B9c and the Tat-NR2B9c fusion peptide remained in neurons for many hours after being applied extracellularly.

To determine whether Tat-NR2B9c may disrupt the interaction between NMDARs and PSD-95, I made use of rat brain proteins prepared under weakly denaturing conditions known to permit the NMDAR/PSD-95 interaction. Adult (7-8 W) wistar rat forebrains were removed and homogenized in ice-cold buffer (0.32M Sucrose, 0.1 mM Na3VO4, 0.1 mM PMSF, 0.02M PNPP, 0.02M glycerol phosphate, and 5 µg/ml each of antipain, aprotinin, and leupeptin). Homogenates were centrifuged at 800 gr for 10 min at 4° C. The supernatants were combined and centrifuged at 11,000 g at 4 degree for 20 min and the pellet (P2) was resuspended in homogenization buffer. P2 membranes were adjusted 200 µg protein/90 ul with homogenization buffer with a final concentration of 1% DOC and 0.1% Triton X-100. The proteins were incubated with Tat-NR2B9c or with one of three controls: Tat38-48, the Tat transduction sequence conjugated to two alanine residues (Tat-AA), or a Tat-NR2B9c peptide in which the C-terminal tSXV motif contained a double point mutation (Tat-KLSSIEADA; Tat-NR2BAA) rendering it incapable of binding PSD-95. I immunoprecipitated NMDARs, together with associated proteins, with an antibody that selectively recognizes NR2B. The proteins were separated by SDS-PAGE and probed with anti-PSD-95 or anti-NR2B antibodies[16] NR2B was precipitated from rat forebrain extracts using a polyclonal rabbit anti-NR2B antibody generated against the C-terminal region encompassing amino acid residues 935-1, 455 of the NR2B protein. Proteins were then separated on 8% SDS-PAGE gels and probed with monoclonal anti-NR2B (Clone 13, Transduction Laboratories) or anti PSD-95 antibodies (Clone 7E3-1B8, Affinity Bioreagents. Inc). Detection of proteins was achieved using HRP-conjugated secondary antibodies and enhanced chemiluminescence. I found that Tat-NR2B9c reduced the co-immunoprecipitation of PSD-95 with NR2B. On average the optical density signal was reduced by 37.6±8.2% as compared with controls (FIG. 5D). In contrast, none of the three control peptides reduced the co-immunoprecipitation of PSD-95 with NR2B. Thus, I conclude that Tat-NR2B9c disrupts the interaction between NMDARs and PSD-95 and that this is dependent upon an intact PDZ binding motif in the peptide.

FIG. 6 shows neuroprotection and reduction of NO signaling by Tat-peptides without affecting NMDAR function (A) Effect of Tat-NR2B9c (50 nM) on field excitatory post-synaptic currents (fEPSC) in CA1 neurons in acute hippocampal slices. (B) Effect of 50 nM Tat-NR2B9c or Tat-38-48 (control) on whole-cell excitatory post synaptic currents (EPSC). (C) Effect of Tat-NR2B9c on the NMDA component of the EPSC isolated pharmacologically by applying the AMPAR antagonist CNQX, and concomitant removal of extracellular $Mg^{2+}$. (D) Effect of 50 nM Tat-NR2B9c treatment on NMDA-evoked $^{45}Ca^{2+}$ uptake in cortical cultures. Tat-peptides were bath-applied 1 h prior to the NMDA application. (E) Effect of 5 µM Tat-NR2B9c treatment on NMDA-evoked cGMP production in cortical cultures. Asterisk: differences from control and Tat-NR2B-AA at each NMDA concentration (Bonferroni t-test, p<0.01). (F) Decreased excitotoxicity at 20 h at all NMDA concentrations in cultured cortical neurons pre-treated with 50 nM Tat-NR2B9c or pTat-PDZ1-2 for 1 h. Asterisk: differences from control, Tat-NR2B-AA and pTat-GK at each NMDA concentration (Bonferroni t-test, p<0.005). Right panels: Representative phase contrast and propodium iodide fluorescence images of cultures 20 h after challenge with 100 µM NMDA with and without Tat-NR2B9c treatment. Bars in (D), (E) and (F) indicate the mean±S.E. for 12 cultures in 3 separate experiments.

Figure 6A:
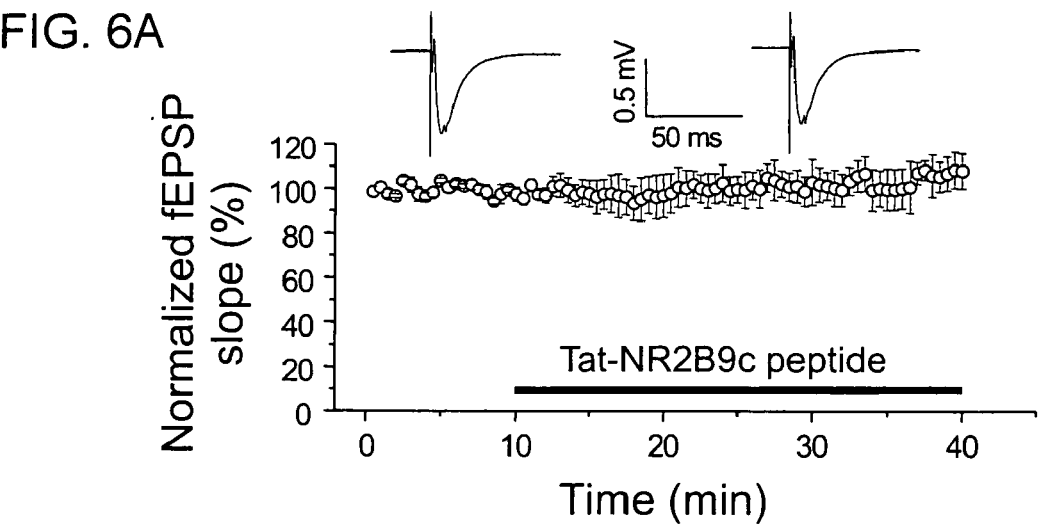
FIG. 6. Effect of Tat-NR2B9c on (A-C) electrophysiological function of neurons (D) NMDA-evoked $^{45}Ca^{2+}$ uptake in cortical cultures. (E) NMDA-evoked cGMP production in cortical cultures. (F) NMDA-evoked excitotoxicity in cortical cultures.
Figure 6B:
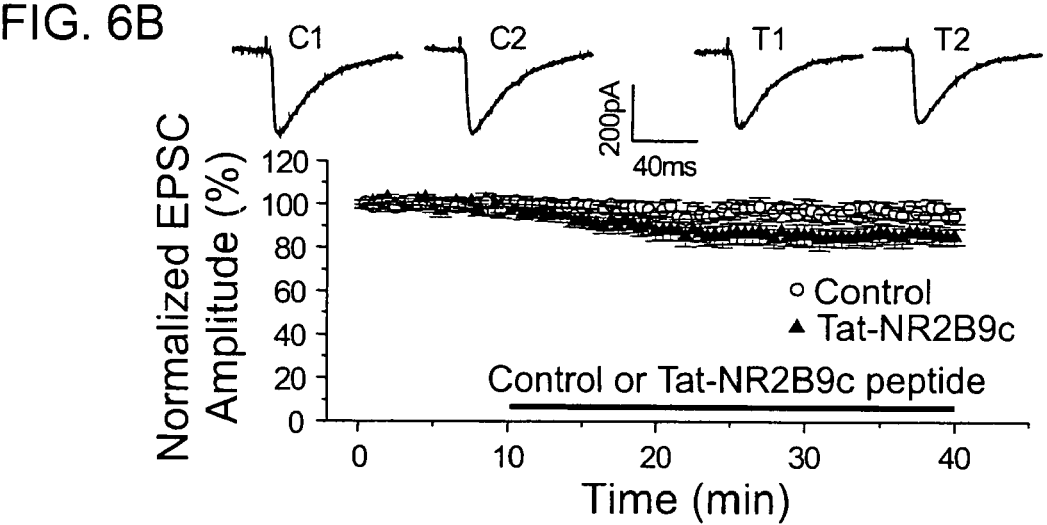
Figure 6C:
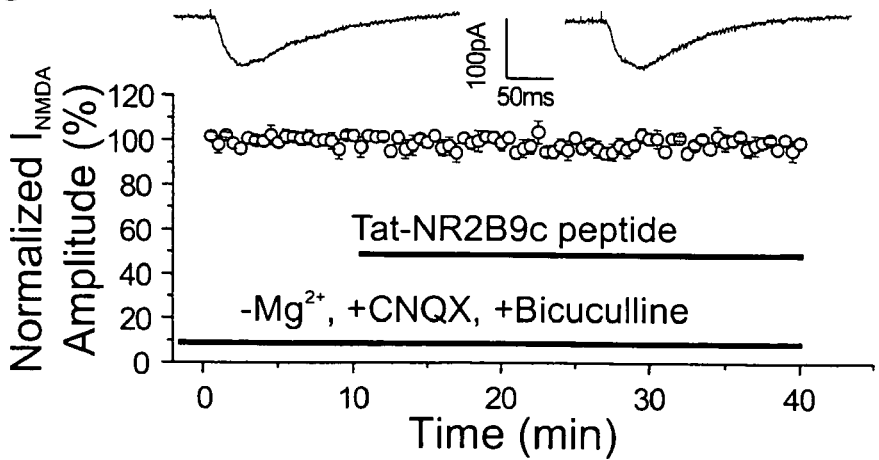
Figure 6D:
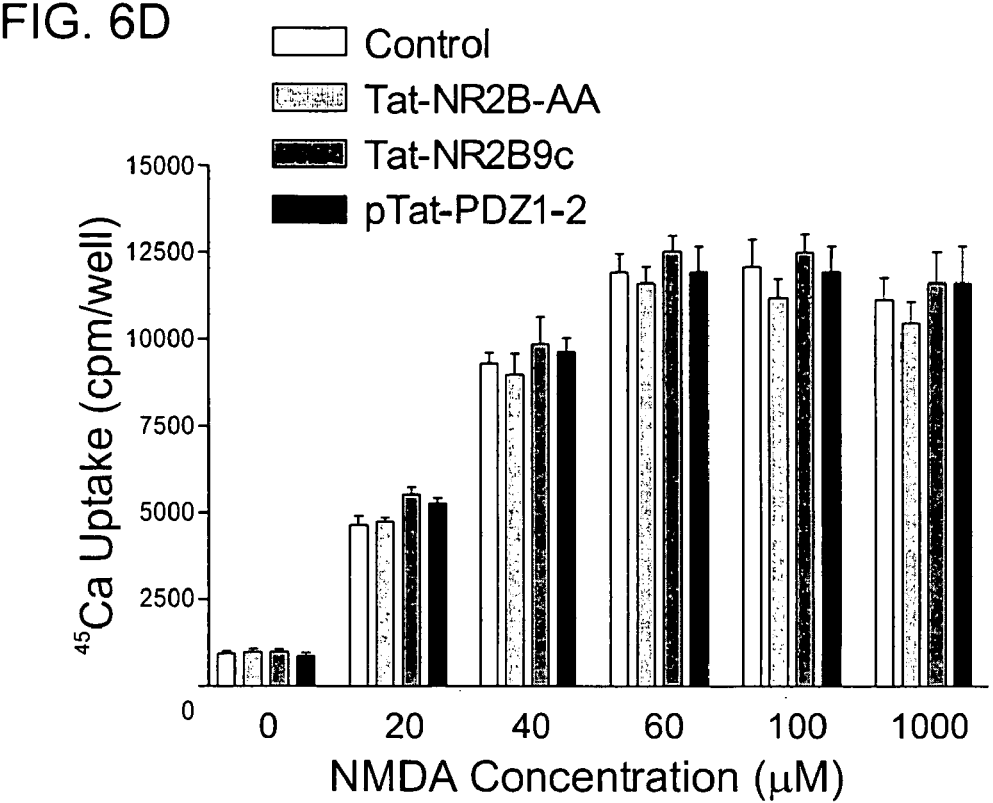

In more detail, as NMDAR-mediated synaptic responses are not altered by the loss of PSD-95 (24) 1 predicted that Tat-NR2B9c would not affect the function of NMDARs. This was tested by examining the effect of Tat-NR2B9c on NMDAR-mediated currents and on NMDA-evoked uptake of $^{45}Ca^{2+}$. Bath-applying Tat-NR2B9c (50 nM) to acute rat hippocampal slices had no effect on synaptic responses of CA1 neurons evoked by stimulation of the Schaffer collateral-commissural pathway (FIG. 6A) nor on patch recordings of the total excitatory post-synaptic currents (EPSC) recorded in CA1 neurons, (FIG. 6B) nor on the pharmacologically isolated AMPA (not shown) or NMDA components of the EPSC (FIG. 6C). Moreover, using cortical cultures I found that pre-treating cultures with Tat-NR2B9c or with pTat-PDZ1-2 (each at 50 nM) did not alter the uptake of $^{45}Ca^{2+}$ produced by applying NMDA (FIG. 6D); CNQX (10 µM) and nimodipine (2 µM) were present in the extracellular solution in these and all subsequent experiments using cultured neurons so as to isolate signaling and thereby preventing secondary activation of AMPARs or of voltage-gated $Ca^{2+}$ channels, respectively (25,32,33).

Figure 6E:
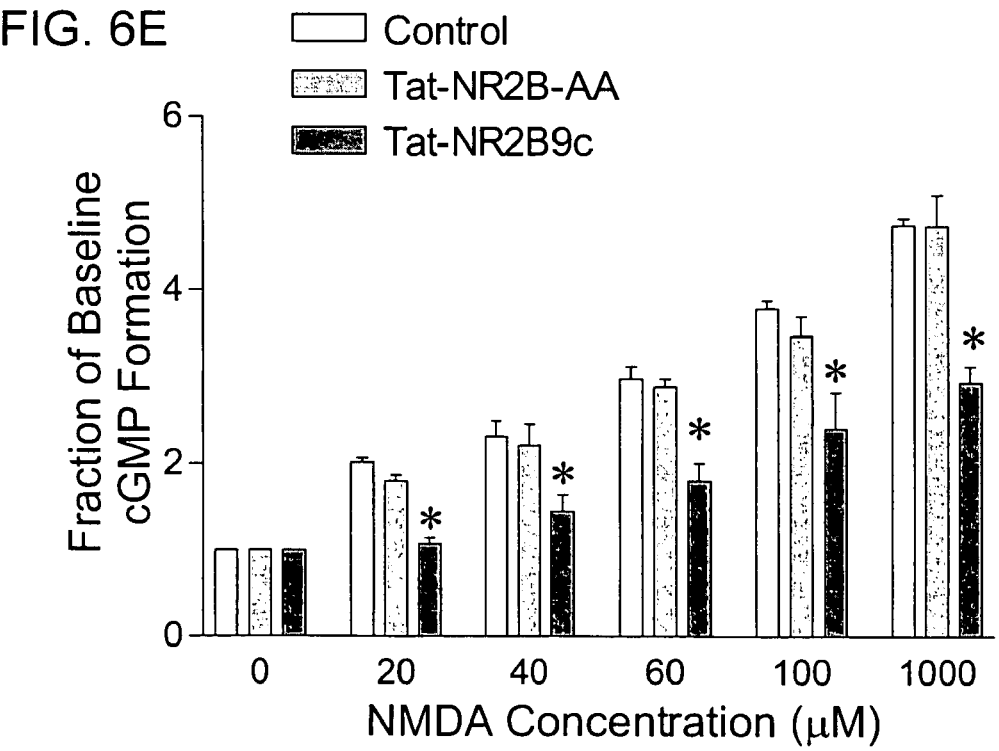

As the function of NMDARs was unaffected by administering Tat-NR2B9c, I next determined whether this peptide altered signaling events downstream of NMDAR activation. To this end I examined stimulation of nNOS, as a key downstream signaling enzyme that mediates the neurotoxic effects of NMDAR activation[5]. I measured NMDA-evoked changes in the levels of guanosine 3',5'-monophosphate (cGMP) as a surrogate measure of NO production by NMDAR stimulated nNOS activity[7;20]. Cultured cortical neurons were pre-treated for 1 h with Tat-NR2B9c (50 nM), the non-interacting Tat-NR2B-AA (50 nM) or with sham washes and challenged with NMDA (0-1000 µM) in the presence of CNQX and nimodipine as above. NMDA produced a concentration-dependent increase in cGMP that was significantly suppressed (average of 39.5±6.7%) by pre-treating the cultures with Tat-NR2B9c (FIG. 6E). In contrast, NMDAR-stimulated elevation of cGMP was unaffected by pre-treatment with Tat-NR2B-AA. Thus, Tat-NR2B9c, but not a mutant peptide incapable of interacting with PSD-95, depressed NMDAR-evoked stimulation of NO-cGMP signaling.

Figure 6F:
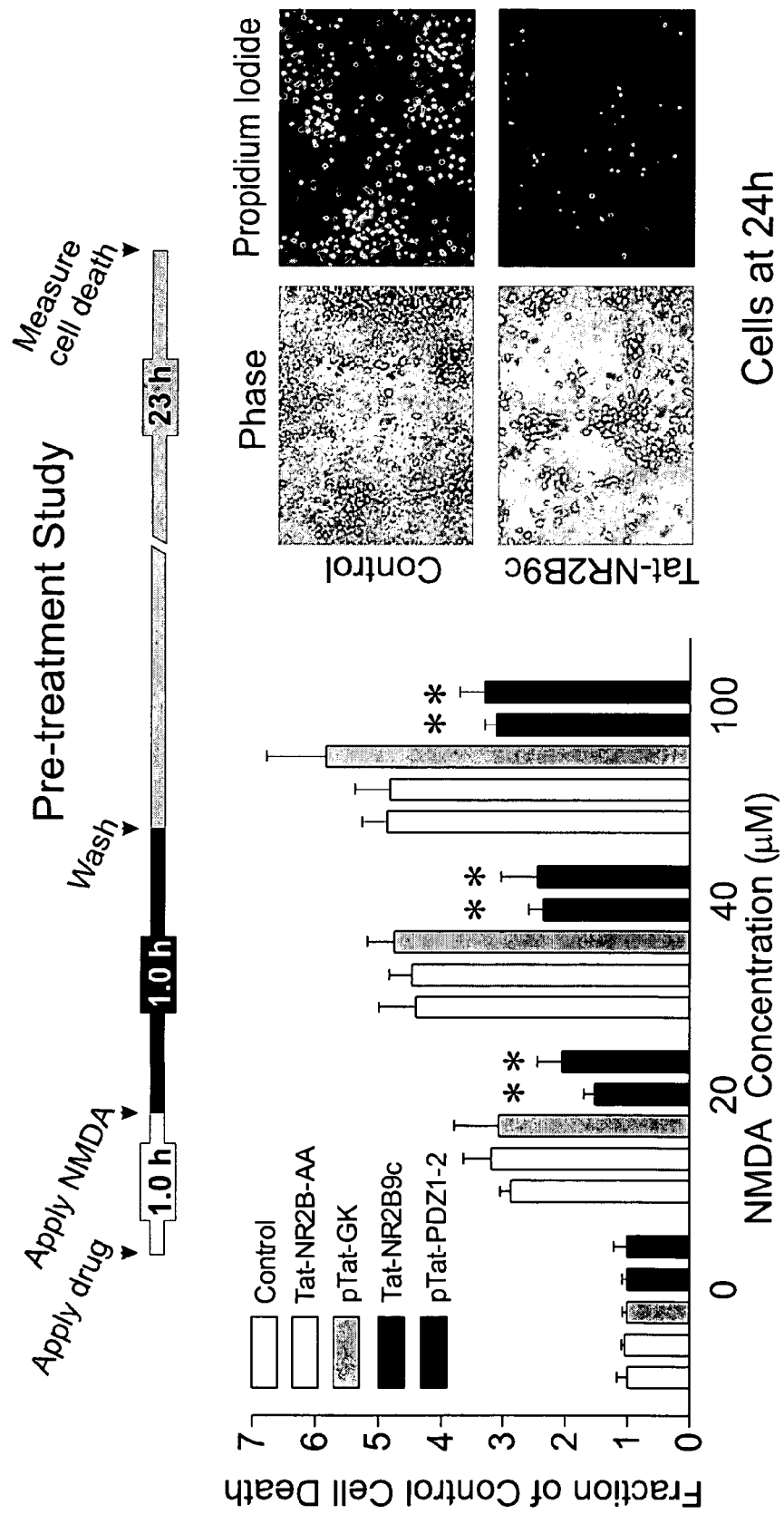

Although Tat-NR2B9c and pTat-PDZ1-2 did not affect NMDAR function, Tat-NR2B9c was shown to interfere with NMDAR/PSD-95 binding and to suppress downstream NO signaling. Thus, I predicted that Tat-peptide treatment should enhance neurons' resilience to NMDA toxicity. To test this I pre-treated cortical neuronal cultures with Tat-peptides (50 nM) for 1 h, then applied NMDA (0-100 µM) for 1 h followed by a 20 h observation period (FIG. 6F, inset). Control neurons were treated with sham washes, or with the non-interacting control Tat-NR2BAA. In cultures treated with Tat-NR2B9c, cell death was significantly reduced at all concentrations tested (FIG. 6F) whereas pre-treatment with Tat-NR2B-AA had no effect on cell death. Thus, NMDAR-stimulated neurotoxicity is suppressed by pre-treatment with Tat-NR2B9c, suppression that is lost by mutating the PSD-95 binding region of the peptide.

If Tat-NR2B9c suppresses NMDA excitotoxicity by interfering with the binding of NR2B to PSD-95 then interfering with this binding by an alternative means should also suppress the toxicity. I tested pTat-PDZ1-2, predicted to interfere with PSD-95 binding to NR2B and which permeates into the cells (not shown), though without effect on NMDA-evoked $Ca^{2+}$ accumulation (FIG. 6D). Pre-treating the cultures with pTat-PDZ1-2 attenuated the neurotoxicity of NMDA to a similar degree as Tat-NR2B9c (FIG. 6F). As a control, I made and used pTat-GK, a Tat fusion protein containing residues 534-724 of PSD-95 comprising the carboxyl-terminal guanylate-kinase homology domain that lacks enzymatic activity[21]. pTat-GK, which is devoid of the necessary domains to bind NR2B, had no effect on the NMDA evoked cell death (FIG. 6F). Thus, interfering with the NMDAR/PSD-95 interaction using peptides that target either side of the interaction reduces in vitro excitotoxicity produced by NMDAR activation.

FIG. 7 shows neuroprotection by Tat-NR2B9c pretreatment in-vivo. (A) Detection of Tat-NR2B9c-dansyl but not Tat38-48-dansyl in the cortex of C57BL/6 mouse brain 1 h after intraperitoneal injection (0.5 μmole total dose). Fluorescence of brains from animals treated with Tat-38-48-dansyl was similar to background (not shown). (B) Composite neurological scores (see text) during and 24 h after MCAo. (C) Pre-treatment with 3 mmole/g Tat-NR2B9c but not mutated Tat-NR2B-AA or saline (control) significantly reduced (i) total infarct area and volume (inset), ANOVA; F=7.3, p<0.005 and (ii) cortical infarct area and volume (inset), ANOVA; F=8.35, p<0.005 measured 24 h after transient MCAo. (n=6 animals per group; symbols and bars indicate mean±S.E). Infarct volume was calculated by analyzing the infarct area in 8 stereotactic coordinates of the brain as shown at right inset.

Agents that block NMDAR activity were initially deemed as promising neuroprotectants for stroke and other neurological disorders involving excitotoxic mechanisms, but were later shown to be deleterious or ineffective in animal and human studies (27,28,29). However, Tat-peptides peptides that target the NMDAR/PSD-95 interaction protect against NMDA toxicity without blocking NMDARs. Therefore I reasoned that treatment with Tat-NR2B9c in vivo could serve as an improvement on NMDA blockers in the treatment of ischemic brain damage.

Before testing this I determined whether Tat-NR2B9c could be delivered into the brain in the intact animal. I injected 25 g C57BL/6 mice intraperitoneally with a 500 μmole dose of either Tat-NR2B9c-dansyl, or with Tat38-48-dansyl as a non-transducing control. 40 μM cryostat coronal brain sections taken 1 h after injection[22] were examined for peptide uptake using dansyl fluorescence detection by confocal microscopy. The mice were perfused with fixative solution (3% paraformaldehyde, 0.25% glutaraldehyde, 10% sucrose, 10 U/mL heparin in Saline) 1 hour after peptide injection. Brains were removed, frozen in 2-methylbutane at −42° C. and 40 μM sections were cut using a Leitz Kryostat. Brain sections from animals injected with Tat-NR2B9c exhibited strong fluorescence in the cortex (FIG. 7A, right), and in all other areas examined (hippocampus, striatum; not shown), whereas signal from controls remained at background levels (FIG. 7A, left). Similar results were obtained using intravenous injection in rats (not shown). Thus, Tat-NR2B9c enters the brain upon peripheral administration.

Next, I examined whether pretreatment with Tat-peptides would reduce stroke damage. Experiments were carried out in adult male Sprague-Dawley rats subjected to transient middle cerebral artery occlusion (MCAO) for 90 minutes by the intraluminal suture method (36,37). Animals were fasted overnight and injected with atropine sulfate (0.5 mg/kg IP). After 10 minutes anesthesia was induced with 3.5% halothane in a mixture of nitrous oxide and oxygen (Vol. 2:1) and maintained with 0.8% halothane. Rats were orally intubated, mechanically ventilated, and paralyzed with pancuronium bromide (0.6 mg/kg IV). Body temperature was maintained at 36.5-37.5° C. with a heating lamp. Polyethylene catheters in the femoral artery and vein were used to continuously record blood pressure and to sample blood for gas and pH measurements. Transient MCAO was achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia. Animals were pretreated with either saline, the Tat-NR2B-AA control, or with Tat-NR2B9c by a single intravenous bolus injection 45 min prior to MCAO (3 nMoles/g). Physiological parameters (body temperature, blood pressure, blood gases) were monitored and maintained throughout the experiment (Table 1). All experimental manipulations and analyses of data were performed by individuals blinded to the treatment groups. The extent of cerebral infarction was measured 24 h after MCAO onset (FIG. 7C inset). The postural reflex test (38), and the forelimb placing test (39) were used to grade neurological function on a scale of 0 to 12 (normal=0; worst=12) during MCAO (at 50 minutes) and 24 h thereafter.

Figure 7B:
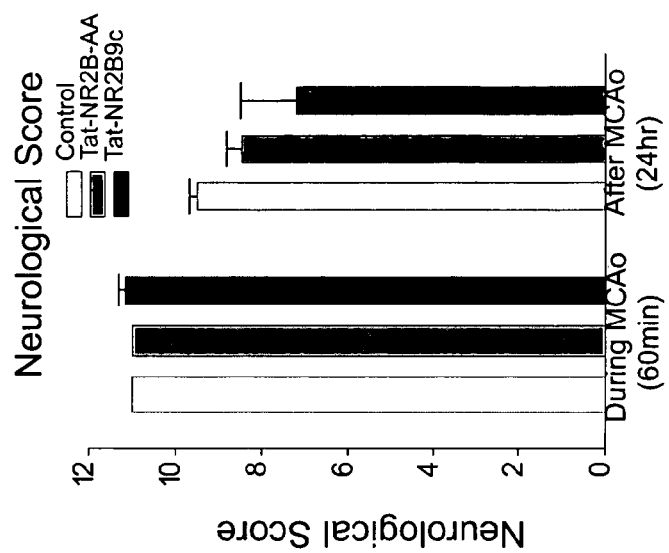
FIG. 7. (A) Detection of Tat-NR2B9c-dansyl in the mouse brain 1 h after intraperitoneal injection (B) Composite neurological scores (see text) during and 24 h after MCAo. (C) Effect of Pre-treatment with Tat-NR2B9c on (i) total infarct area and volume (inset), and (ii) cortical infarct area and volume (inset) after transient MCAo.
Figure 7A:
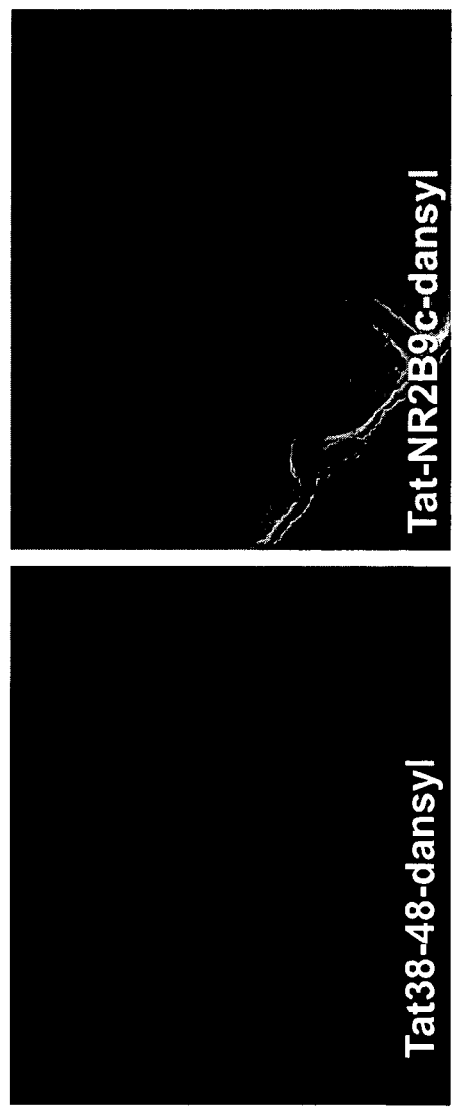
Figure 7C:
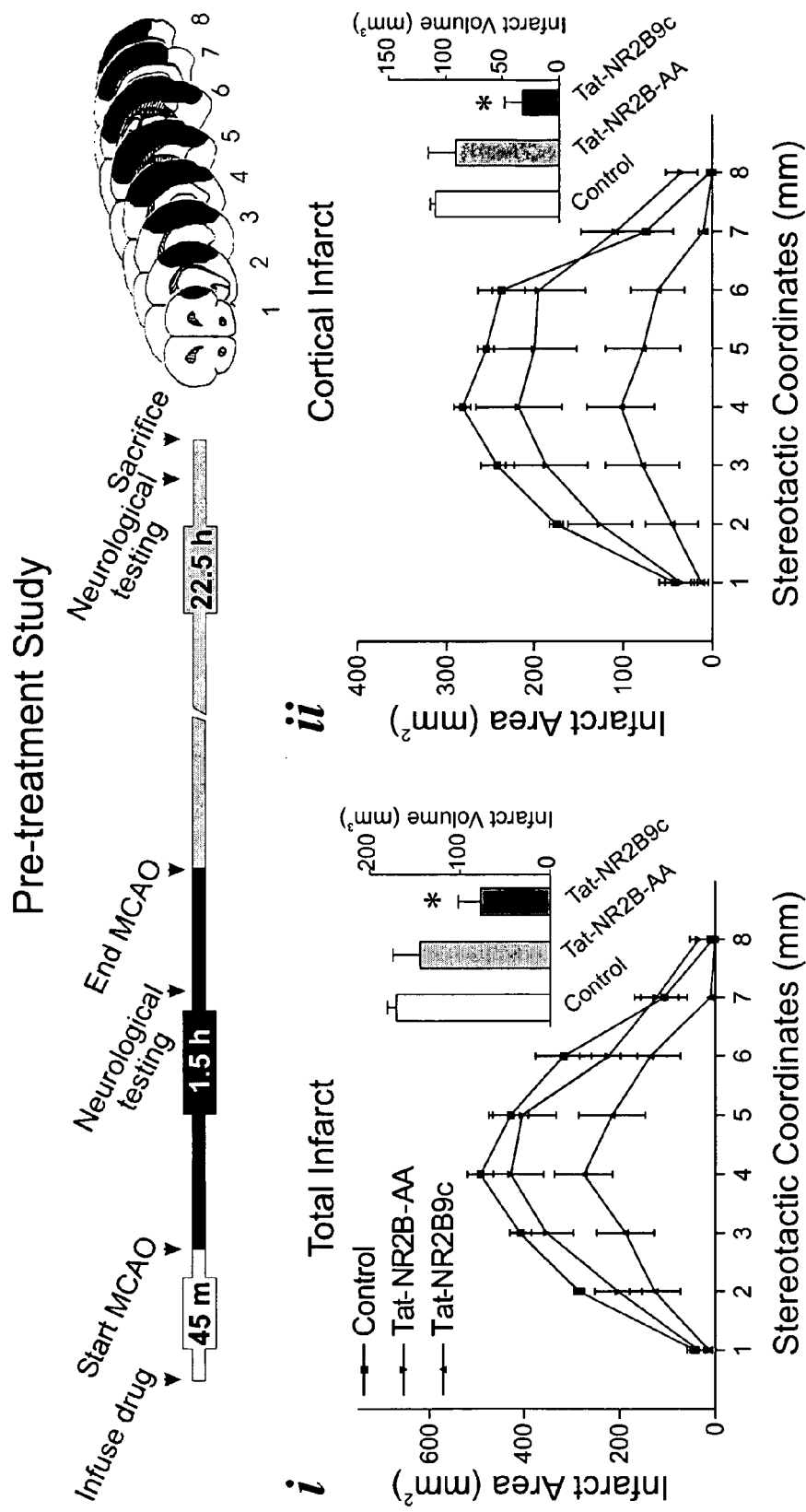

Pretreatment with Tat-NR2B9c produced a trend toward improvement in 24 h neurological scores in animals treated with Tat-NR2B9c (FIG. 7B). Moreover, the treatment reduced the volume of total cerebral infarction by 54.6±11.27% as compared with stroke volume in controls (FIG. 7$C_i$; ANOVA, F=7.289, p=0.0048). This effect was largely accounted-for by a 70.7±11.23% reduction in cortical infarction (FIG. 7$C_{ii}$, ANOVA, F=8.354, p=0.0027), which is thought to be largely caused by NMDAR-dependent mechanisms.

A treatment for stroke with a single-bolus drug injection would be most therapeutically valuable if effective when given after the onset of ischemia. I thus first evaluated whether treatment with Tat-peptides could be neuroprotective when applied post-insult in vitro.

Figures 8A, 8B:
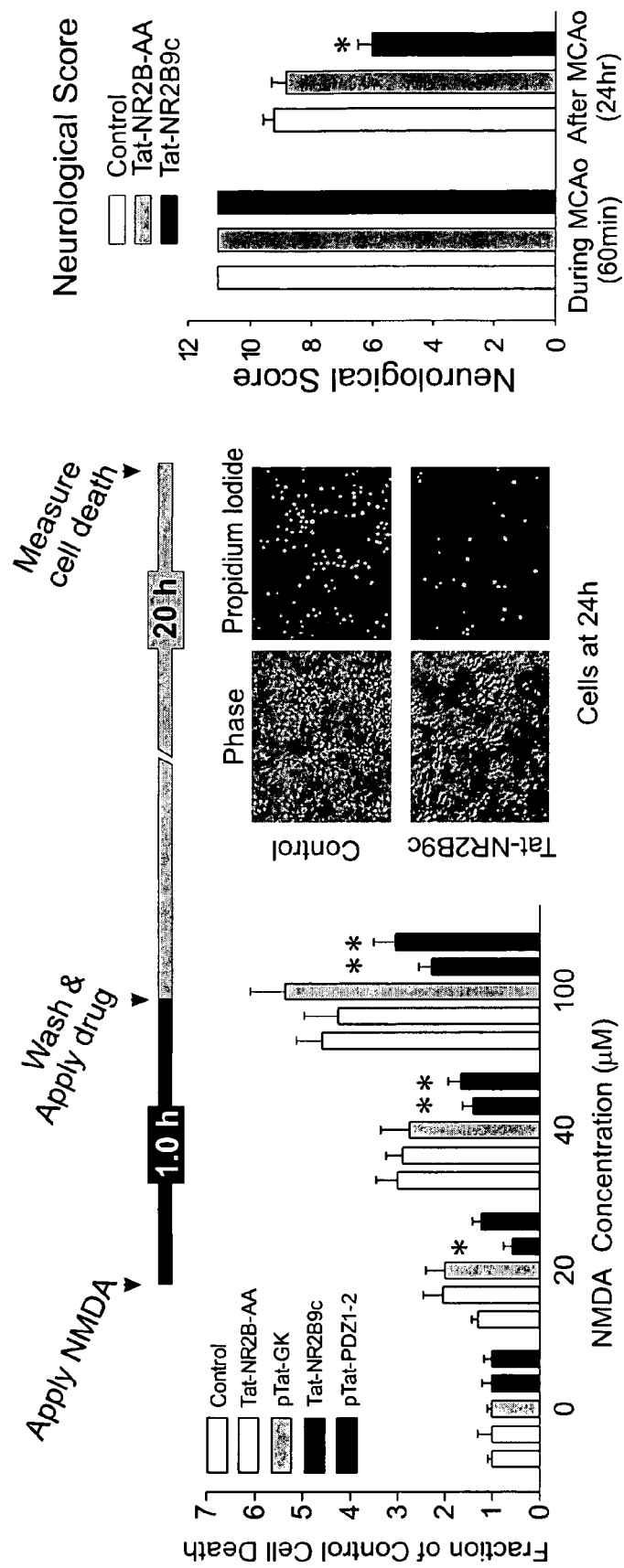
FIG. 8. (A) Neuroprotective effects of post-treatment in cultured cortical neurons post-treated with Tat-NR2B9c or pTat-PDZ1-2 (B) Composite neurological scores (see text) during and 24 h after MCAo. (C) Effect of post-treatment with Tat-NR2B9c on (i) total infarct area and volume (inset), and (ii) cortical infarct area and volume (inset) after transient MCAo.
Figure 8C:
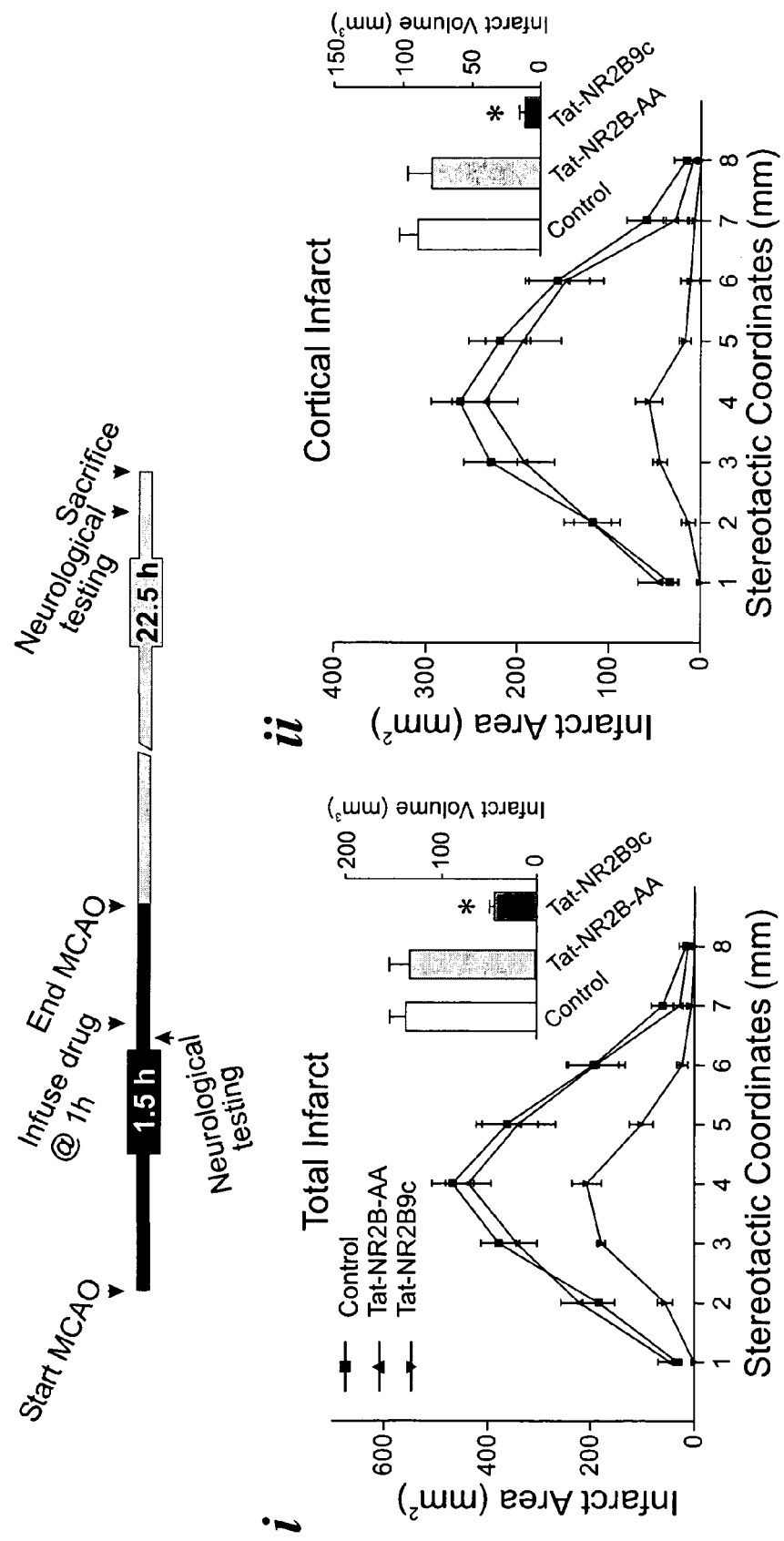
Figure 8D:
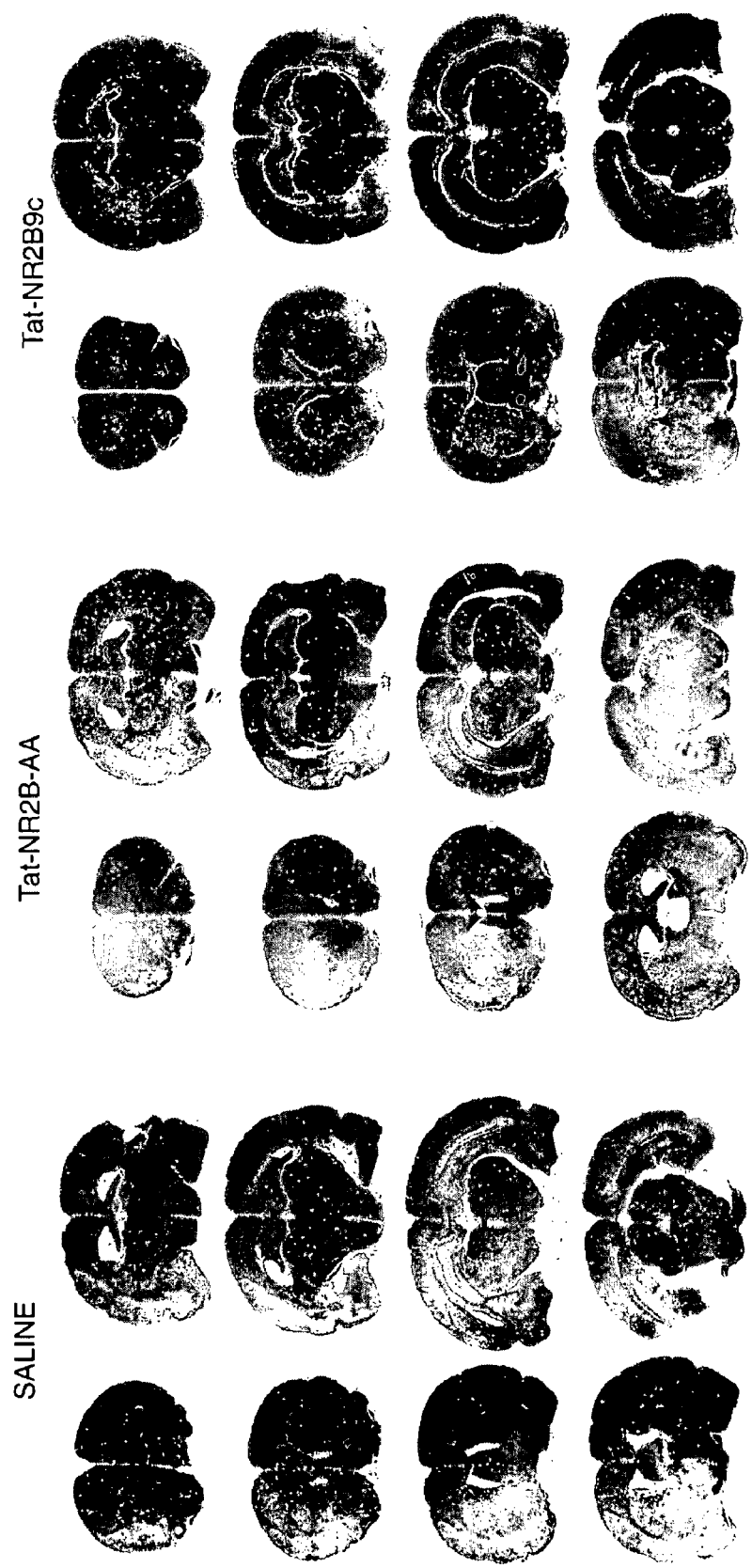

FIG. 8 shows neuroprotection by post-treatment with Tat-NR2B9c in-vitro and in-vivo (A) Decreased excitotoxicity at 20 h in cultured cortical neurons post-treated with 50 nM Tat-NR2B9c or pTat-PDZ1-2 at 1 h after NMDA application. Bars indicate the mean±S.E. for 12 cultures in 3 separate experiments. Asterisk: differences from control, Tat-NR2B-AA and pTat-GK at each NMDA concentration (Bonferroni t-test, p<0.005). Right panels: Representative phase contrast and propodium iodide fluorescence images of cultures 24 h after challenge with 100 μM NMDA with and without Tat-NR2B9c treatment. (B) Composite neurological scores (see text) during and 24 h after MCAo. Asterisk: difference from control and Tat-NR2B-AA (ANOVA; F=17.25, p<0.0001). (C) Post-treatment with 3 nmole/g Tat-NR2B9c (9 animals) but not mutated Tat-NR2B-AA (8 animals) or saline controls (10 rats) significantly reduced (i) total infarct area and volume (inset), ANOVA; F=12.0, p<0.0005 and (ii) cortical infarct area and volume (inset), ANOVA; F=12.64, p=0.0001 as measured 24 h after transient MCAo. Symbols and bars indicate mean±S.E (D). Representative appearance of H&E stained rat brain sections from which the infarct areas were analyzed.

Cultured cortical neurons were exposed to an NMDA challenge (0-100 μM) for 1 h and were then treated with the Tat-peptides (all at 50 nM) described in the pre-treatment study (FIG. 6F). Cell death was gauged 20 h thereafter (FIG. 8A-inset). Post-treatment with Tat-NR2B9c or with pTat-PDZ1-2 significantly reduced the vulnerability of neurons to NMDA toxicity as compared with control cultures post-treated with sham washes, with Tat-NR2BAA, or with pTat-GK (FIG. 8A). Thus, when administered 1 h after the start of the NMDA insult each of the Tat fusion constructs that target the NMDAR/PSD-95 interaction significantly reduced neuronal cell death in vitro.

Next, I examined whether treatment with Tat-NR2B9c could attenuate ischemic neuronal damage in-vivo when given after stroke onset. A post-treatment study was conducted in which the rats were subjected to transient MCAO for 90 minutes as before, but the intravenous saline or Tat-peptide bolus (Tat-NR2B9c or Tat-NR2B-AA; 3 nMole/g) was injected 1 h after MCAO onset (FIG. 8C-*inset*). Infarction volume and neurological outcome measurements were performed at times identical to the pre-treatment study. Body temperature, blood pressure and blood gases were monitored throughout the 24 h experiment and maintained equivalent between groups (Table 2).

Post-treatment with Tat-NR2B9c, but not with Tat-NR2B-AA or saline, resulted in animals exhibiting a significant improvement in 24 h neurological scores as compared with controls (FIG. 8B; ANOVA, F=17.25, p<0.0001). Most strikingly, post-treatment with Tat-NR2B9c reduced the volume of total cerebral infarction by 67.0±3.75% as compared with stroke volume in controls (FIG. $8C_i$; ANOVA, F=11.99, p=0.0002). Similar to the previous study, this reduction was accounted-for by a 86.97±4.38% reduction in cortical infarction volume (FIGS. $8C_{ii}$, 4D; ANOVA, F=12.64, p<0.0001).

The aforesaid description demonstrates that introducing into cells an exogenous peptide containing the C-terminal nine amino acids of the NR2B NMDAR subunit has profound effects on signaling pathways downstream of NMDAR activation, on in vitro excitotoxicity, and on in vivo ischemic brain damage. The effects of this peptide are lost by mutating amino acids that are essential for mediating PDZ binding to PSD-95. In addition, a protein comprising PDZ1-2 of PSD-95 shares the effects of the NR2B C-terminal peptide. Together these findings imply that the downstream signaling from NMDARs that leads to negative consequences for neuronal viability may be interrupted by interfering with the interaction between NR2B and PSD-95.

I have discovered that the strategy of treating neurons with Tat-fusion peptides is effective in reducing vulnerability to excitotoxicity in vitro and stroke damage in vivo. As this occurs without affecting NMDAR activity then adverse consequences of blocking NMDARs are not expected. Efficacy after the insult onset suggests that targeting the NMDAR/PSD-95 interaction is a practical future strategy for treating stroke.

TABLE 1

Physiological Variables in Pre-Treatment MCAO Study

| Physiological Variables | Control (n = 6) | TAT-NR2BAA (n = 6) | TAT-NR2B9c (n = 6) |
|---|---|---|---|
| Before anesthesia | | | |
| Body weight, g | 269 ± 6 | 273 ± 7 | 271 ± 5 |
| Before MCAo (45 min) | | | |
| Body Temperature, °C | 36.7 ± 0.07 | 36.7 ± 0.17 | 36.6 ± 0.21 |
| MABP, mmHg | 119 ± 4 | 115 ± 5 | 120 ± 9 |
| Before MCAo (30 min) | | | |
| Body Temperature, °C | 36.8 ± 0.08 | 36.5 ± 0.12 | 36.7 ± 0.19 |
| MABP, mmHg | 107 ± 3 | 110 ± 4 | 76 ± 5* |
| Blood gases | | | |
| PH | 7.44 ± 0.02 | 7.44 ± 0.02 | 7.44 ± 0.02 |
| PO2, mmHg | 104 ± 3 | 110 ± 7 | 123 ± 8 |
| PCO2, mmHg | 39.6 ± 1.3 | 39.1 ± 1.4 | 38.1 ± 1.4 |
| Before MCAo (15 min) | | | |
| Body Temperature, °C | 36.9 ± 0.11 | 36.6 ± 0.15 | 36.7 ± 0.20 |
| MABP, mmHg | 111 ± 6 | 115 ± 5 | 90 ± 6* |
| During MCAo (5 min) | | | |
| Body Temperature, °C | 36.9 ± 0.03 | 36.6 ± 0.17 | 36.7 ± 0.16 |
| MABP, mmHg | 132 ± 6 | 135 ± 7 | 112 ± 9 |
| Blood gases | | | |
| PH | 7.44 ± 0.02 | 7.44 ± 0.02 | 7.44 ± 0.02 |
| PO2, mmHg | 118 ± 3 | 109 ± 4 | 112 ± 6 |
| PCO2, mmHg | 39.2 ± 0.6 | 39.6 ± 0.5 | 41.0 ± 1.3 |
| During MCAo (15 min) | | | |
| Body Temperature, °C | 36.9 ± 0.09 | 36.7 ± 0.15 | 36.8 ± 0.23 |
| MABP, mmHg | 116 ± 9 | 111 ± 6 | 98 ± 6 |
| After MCAo (15 min) | | | |
| Body Temperature, °C | 36.9 ± 0.09 | 36.8 ± 0.08 | 36.8 ± 0.12 |
| After MCAo (24 hr) | | | |
| Body Temperature, °C | 36.6 ± 0.14 | 37.0 ± 0.25 | 36.5 ± 0.14 |
| Body weight, g | 238 ± 6 | 244 ± 6 | 250 ± 5 |

MABP: Mean arterial blood pressure
*P < 0.05, Student's t-test

TABLE 2

Physiological Variables in Post-Treatment MCAO Study

| Physiological Variables | Control (n = 10) | TAT-NR2BAA (n = 8) | TAT-NR2B9c (n = 9) |
|---|---|---|---|
| Before anesthesia | | | |
| Body weight, g | 314 ± 4 | 301 ± 5 | 306 ± 7 |
| Before MCAo (15 min) | | | |
| Body Temperature, °C | 36.9 ± 0.07 | 36.7 ± 0.07 | 36.6 ± 0.07 |
| MABP, mmHg | 103 ± 4 | 103 ± 6 | 103 ± 5 |
| Blood gases | | | |
| PH | 7.43 ± 0.01 | 7.45 ± 0.01 | 7.43 ± 0.02 |
| PO2, mmHg | 113 ± 4 | 113 ± 4 | 105 ± 4 |
| PCO2, mmHg | 39.4 ± 1.0 | 37.9 ± 1.1 | 40.1 ± 1.0 |
| During MCAo (15 min) | | | |
| Body Temperature, °C | 36.9 ± 0.07 | 36.7 ± 0.11 | 37.0 ± 0.07 |
| MABP, mmHg | 120 ± 5 | 121 ± 5 | 119 ± 8 |
| Blood gases | | | |
| PH | 7.44 ± 0.01 | 7.46 ± 0.01 | 7.43 ± 0.01 |
| PO2, mmHg | 113 ± 3 | 108 ± 2 | 111 ± 4 |
| PCO2, mmHg | 39.3 ± 0.7 | 48.0 ± 1.2 | 39.8 ± 0.9 |
| During MCAo (60 min) | | | |
| Body Temperature, °C | 37.1 ± 0.21 | 37.0 ± 0.31 | 36.7 ± 0.11 |
| MABP, mmHg | 146 ± 5 | 149 ± 4 | 143 ± 5 |
| During MCAo (65 min) | | | |
| Body Temperature, °C | 37.1 ± 0.16 | 37.0 ± 0.29 | 36.9 ± 0.08 |
| MABP, mmHg | 134 ± 6 | 136 ± 5 | 137 ± 4 |
| After MCAo (15 min) | | | |
| Body Temperature, °C | 37.0 ± 0.09 | 36.9 ± 0.23 | 36.8 ± 0.08 |
| MABP, mmHg | 128 ± 6 | 116 ± 4 | 119 ± 4 |
| After MCAo (24 hr) | | | |
| Body Temperature, °C | 36.6 ± 0.14 | 36.7 ± 0.27 | 36.4 ± 0.24 |
| Body weight, g | 276 ± 3 | 276 ± 6 | 279 ± 8 |

MCAo: Middle cerebral artery occlusion;
MABP: Mean arterial blood pressure

My next objective was to determine if a single injection of TAT-NR2B9c administered systemically 3 hours post-ischemia in rats could produce long-term functional neuroprotection.

First, I determined the effects of a single i.v. injection of varying doses of TAT-NR2B9c on baseline behaviours in male Sprague-Dawley rats. No significant changes in sensory-motor, open field, or exploratory behaviour (13) were detected over 4 hours at doses ranging from $5\times10^{-7}$ to $5\times10^{-5}$ moles/kg (0.5-50 nmols/g).

Next I investigated the effects of a single i.v. injection of TAT-NR2B9c (3 nmoles/g), a control peptide (TAT-NR2B-AA) consisting of the TAT-NR2B9c peptide in which the COOH-terminal tSXV motif contained a double point mutation rendering it incapable of binding PSD-95 (Kornau et al., 1995)(3 mmoles/g), and saline on a variety of physical, sensory-motor, emotive and cognitive tests. Adult male Sprague-Dawley rats were subjected to transient unilateral middle cerebral artery occlusion (MCAO) for 90 minutes by the intraluminal suture method (Longa et al., 1989; Belayev et al., 1996) under isoflurane (2% in medical air) anesthesia supplemented with 0.05% oxygen (previously shown to maintain blood gases in the normal range; data not shown). Core temperature and non-invasive blood pressure were monitored prior, during and subsequent to surgery and were not significantly different between groups Mean ($\forall$ SE) core temperature recorded prior, during or subsequent to surgery was Tat-NR2B9c: 36.7 ($\forall$ 0.2), 37.1 ($\forall$ 0.1), 37.9 ($\forall$ 0.2); Tat-NR2B-AA: 36.9 ($\forall$ 0.1), 37.2 ($\forall$ 0.2), 37.3 ($\forall$ 0.1); Saline: 37.1 ($\forall$ 0.1), 37.4 ($\forall$ 0.1), 37.5 ($\forall$ 0.3). Mean ($\forall$ SE) systolic blood pressure recorded prior, during or subsequent to surgery was Tat-NR2B9c: 106 ($\forall$ 4.3), 112 ($\forall$ 6.3), 122 ($\forall$ 5.5); Tat-NR2B-AA: 113 ($\forall$ 8.8), 109 ($\forall$ 5.9), 115 ($\forall$ 5.9); Saline: 105 ($\forall$ 5.9), 109 ($\forall$ 3.6), 118 ($\forall$ 7.0)) [F (2,27)=0.50, p=0.614 and F (2,27)=0.14, p=0.867 for temperature and blood pressure respectively]. Drug solutions were injected (i.v) 3 hours after the onset of ischemia (1.5 hours after suture removal). Animals that did not experience intracerebral hemorrhage during surgery or 2 hours subsequent to recovery from final anesthesia were re-coded to ensure lack of experimenter bias and subjected to an intensive post-operative care protocol developed Ain house@ (modified from Modo et al., 2000) that resulted in 100% survival.

Figure 9A:
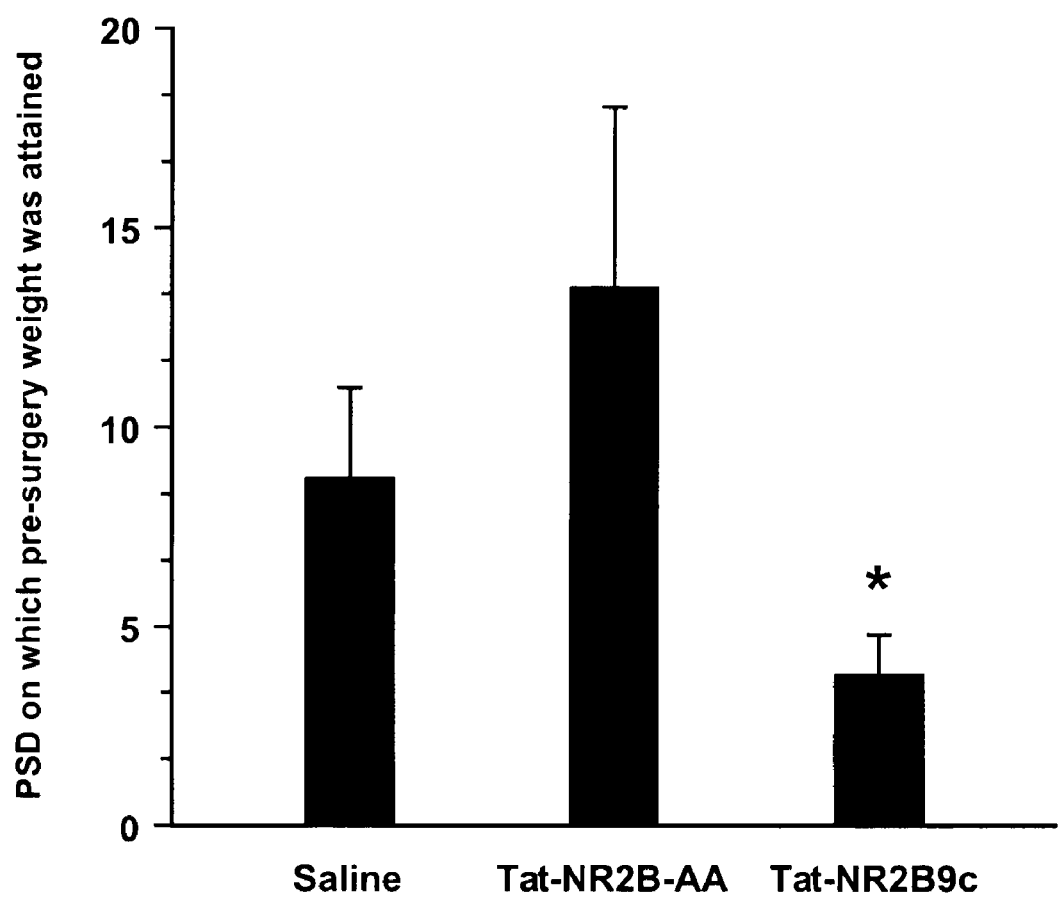
FIG. 9. A. Rats treated with Tat-NR2B9c at 3 hours post-MCAO returned to pre-surgery weight significantly earlier than rats in the two control groups [t(25.6)=2.73, p<0.05]. B. Mean sensory-motor score ($\forall$ SE) over 56 days post-MCAO (maximum unilateral deficit score=7) in groups treated with Tat-NR2B9c (stars), Tat-NR2B-AA (squares) or saline (circles) reveals significant long-term functional neuroprotection with Tat-Nr2B9c [ANOVA; F(2,27)=4.25, p=0.025]. C. and D. Mean ($\forall$ SE) number of paw slips (C) and latency (D) in performance of a horizontal ladder task on post-surgery days 5, 9 and 14. Rats treated with Tat-NR2B9c made significantly fewer paw slips [ANOVA; F(2,27)=3.80, p=0.035] and had significantly reduced latencies [ANOVA, F(2,27)=6.94, p=0.005] relative to controls.

Examination of the day on which animals returned to pre-surgery weight for 2 consecutive days revealed that, on average, NR2B9c treated rats reached criteria about 1 week earlier than saline or NR2B-AA treated rats; an effect that was significant when control group data were combined [t(25.6=2.73, p<0.05](In cases where data analysis of individual groups by ANOVA, with or without repeated measures as appropriate, revealed an F statistic corresponding to 0.05<p<0.1, data from Tat-NR2B-AA and saline groups was combined for comparison with Tat-NR2B9c by Student's t-test with unequal N's.) and approached significance when groups were analyzed separately by repeated measures ANOVA (FIG. 9A). Moreover, analysis of individual weight data post-surgery revealed that TAT-NR2B9c treated rats were significantly heavier than controls on a number of days including day 56 post-injury [t(28)=1.67, p=0.05].

Figure 9B:
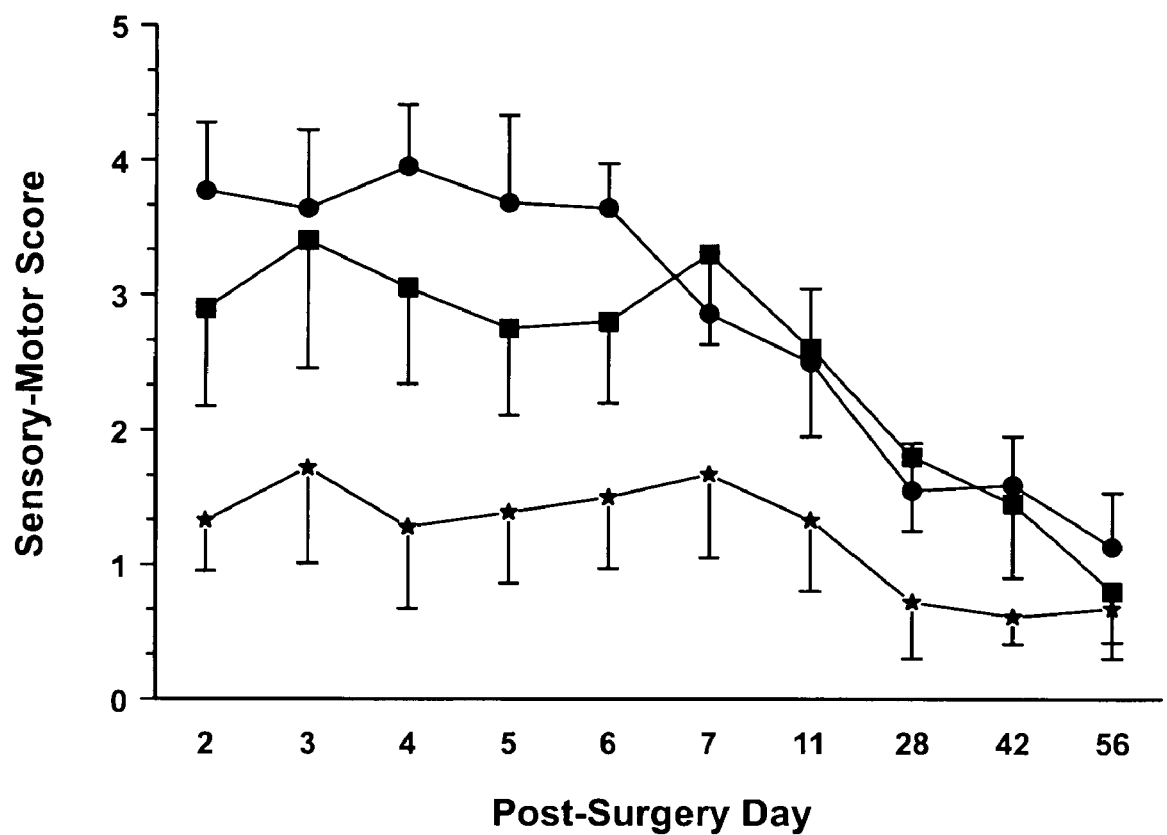
Figure 9C:
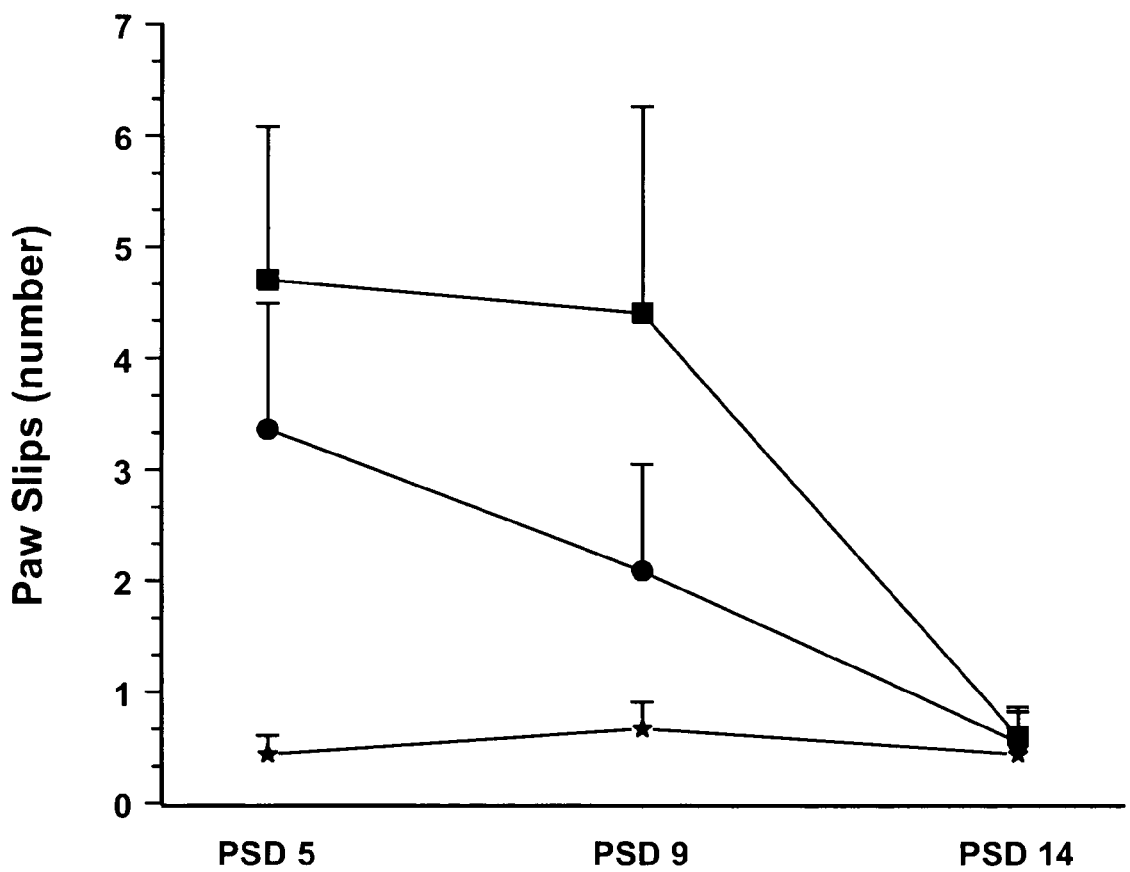
Figure 9D:
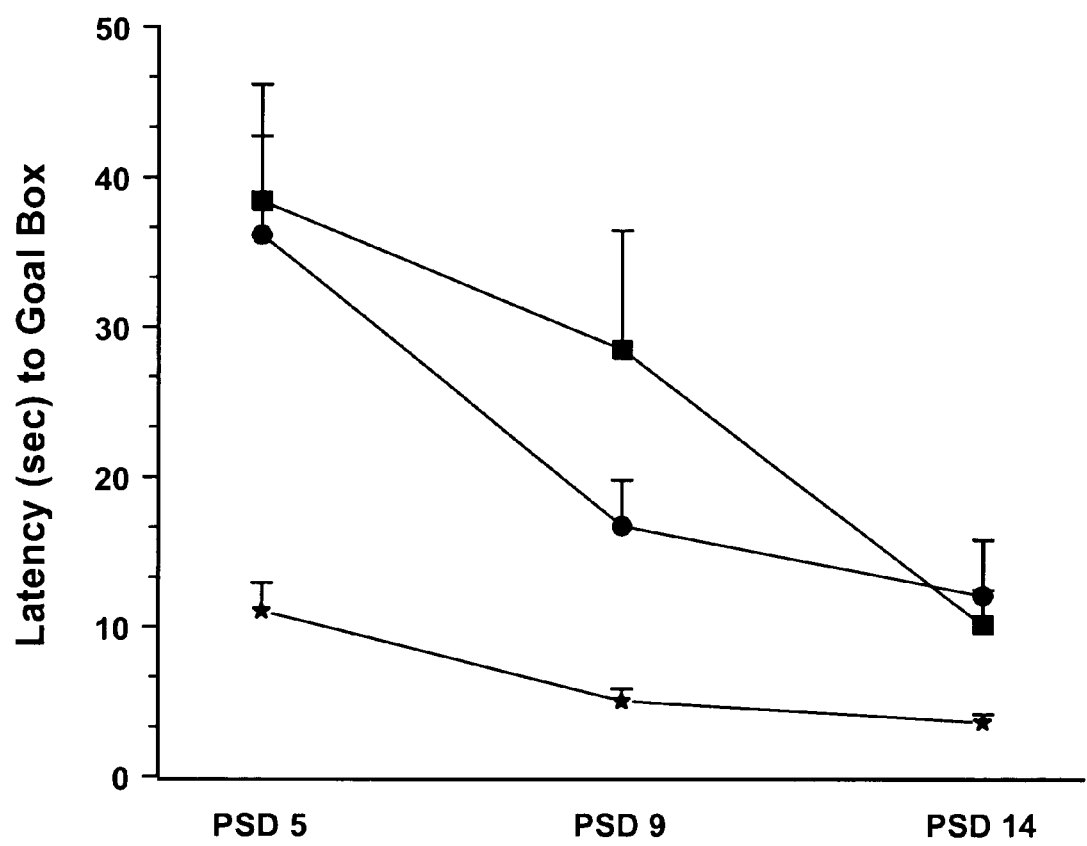

Ischemic strokes often result in impairment to sensory-motor function (Hunter et al., 2000). I employed an 11 point bilateral sensory-motor test battery to measure function daily for the first week and on preset days until day 56 following surgery. Analysis of daily cumulative score data (2 way ANOVA with day as a repeated measure) revealed a significant main effect for treatment [F (2,27)=4.25, p=0.0248]. Subsequent post-hoc analysis (Tukey's HSD) indicated that rats treated with NR2B9c were significantly less impaired than those receiving TAT-NR2B-AA or saline (FIG. 9B). To my knowledge this is the first demonstration of functional neuroprotection in rats almost two months after a single injection of an anti-excitotoxic compound. To assess more complex sensory-motor skills I tested rats on a standard horizontal ladder on postsurgery days 5, 9 and 14. Analysis of the number of paw slips revealed a significant overall effect for treatment [F (2,27)=3.80, p=0.035] which was due to NR2B9c rats making significantly fewer errors than rats receiving NR2B-AA, who were not different than saline (FIG. 9C). Performance in the horizontal ladder task can also be analyzed as the latency to reach the goal box. Using this performance parameter, rats treated post-ischemia with NR2B9c had significantly shorter escape latencies than animals treated with either saline or NR2B-AA [F (2,27)=6.94, p=0.005] (FIG. 9D).

Figure 10A:
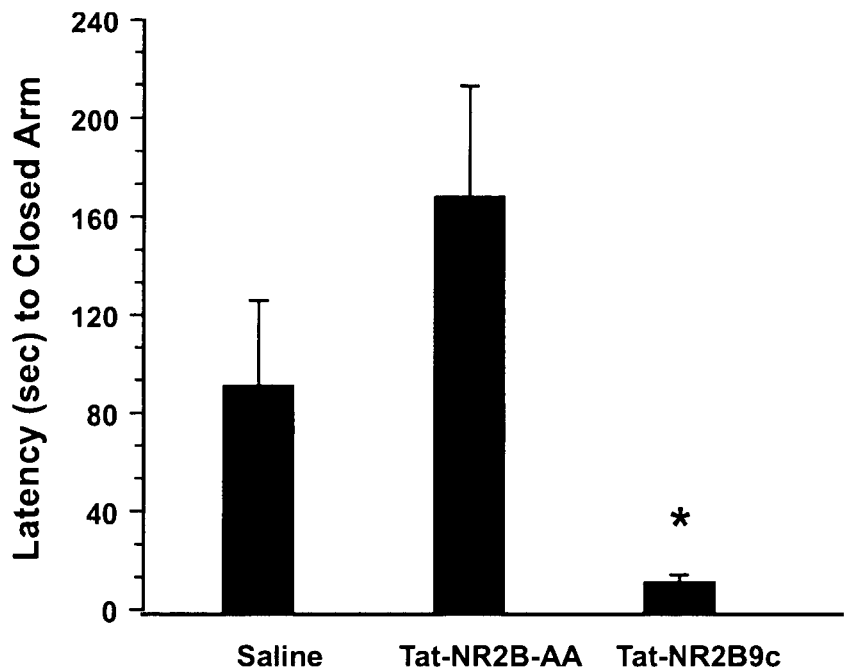
FIG. 10. A. Habituation score for grid crosses in the open field arena. Untreated rats reduce exploratory activity upon repeat exposure. Asterisk indicates a significant difference from Tat-NR2B-AA and Saline [ANOVA, F(2,29)=6.62, p=0.0046]. B. Mean ($\forall$ SE) latency to retreat from the open to the closed arm in the elevated plus maze 6 days following MCA occlusion. Asterisk indicates a significant difference from Tat-NR2B-AA [ANOVA, F(2,27)=5.02, p=0.0140]. Saline (n=11), Tat-NR2B-AA (n=10), Tat-NR2B9c (n=9).
Figure 10B:
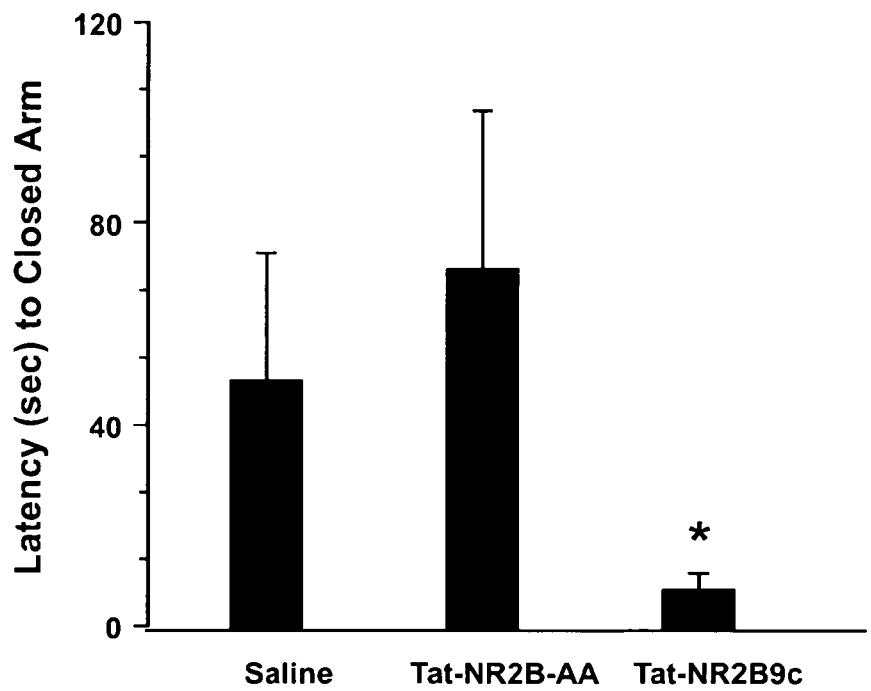

Patients who survive an ischemic stroke often present with emotional deficits that manifest as chronic depression, anxiety and emotional lability (House et al., 2004). Reliable measures of emotionality in rodents are difficult to study in isolation from confounding variables such as motor impairment, especially when animals can not be treated with either reinforcing or aversive chemicals due to their inclusion in other tests. None-the-less I tested animals using two well established models; exploration of an open field and elevated plus maze performance on days 5, 10, 15 and 6, 13, 20 respectively. Separate two-way repeated measures ANOVAs on the open field data revealed no significant differences between groups with respect to either total grid crosses (p=0.412) or time in locomotion (p=0.577). Interestingly, however, rats that had received NR2B9c following stroke habituated to the open field arena whereas those in the two control groups did not (FIG. 10A). Because rats normally habituate to these environments rapidly, these data can be interpreted as evidence that the NR2B9c rats are behaving more normally than those in the control groups. To test this I established a habituation score for each group based on the difference between day 5 and day 15 performance. Analysis of the results revealed a significant difference between experimental animals and both control groups [F (2,27)=6.62, p<0.01](FIG. 10A). Performance in the elevated plus maze was quantified as the mean latency to enter the closed arm from an open arm start position; normally rats tend to avoid open spaces. The data presented in FIG. 10B indicate that NR2B9c treated rats tended to have shorter latencies to enter the closed arm than those in other groups. This tendency was statistically significant on all three test days if data from both control groups was combined (19)[Day 6: t(20)=4.05, p<0.01; Day 13: t(20) =2.62, p<0.01; Day 20: t(20)=1.95, p<0.05].

Figure 11A:
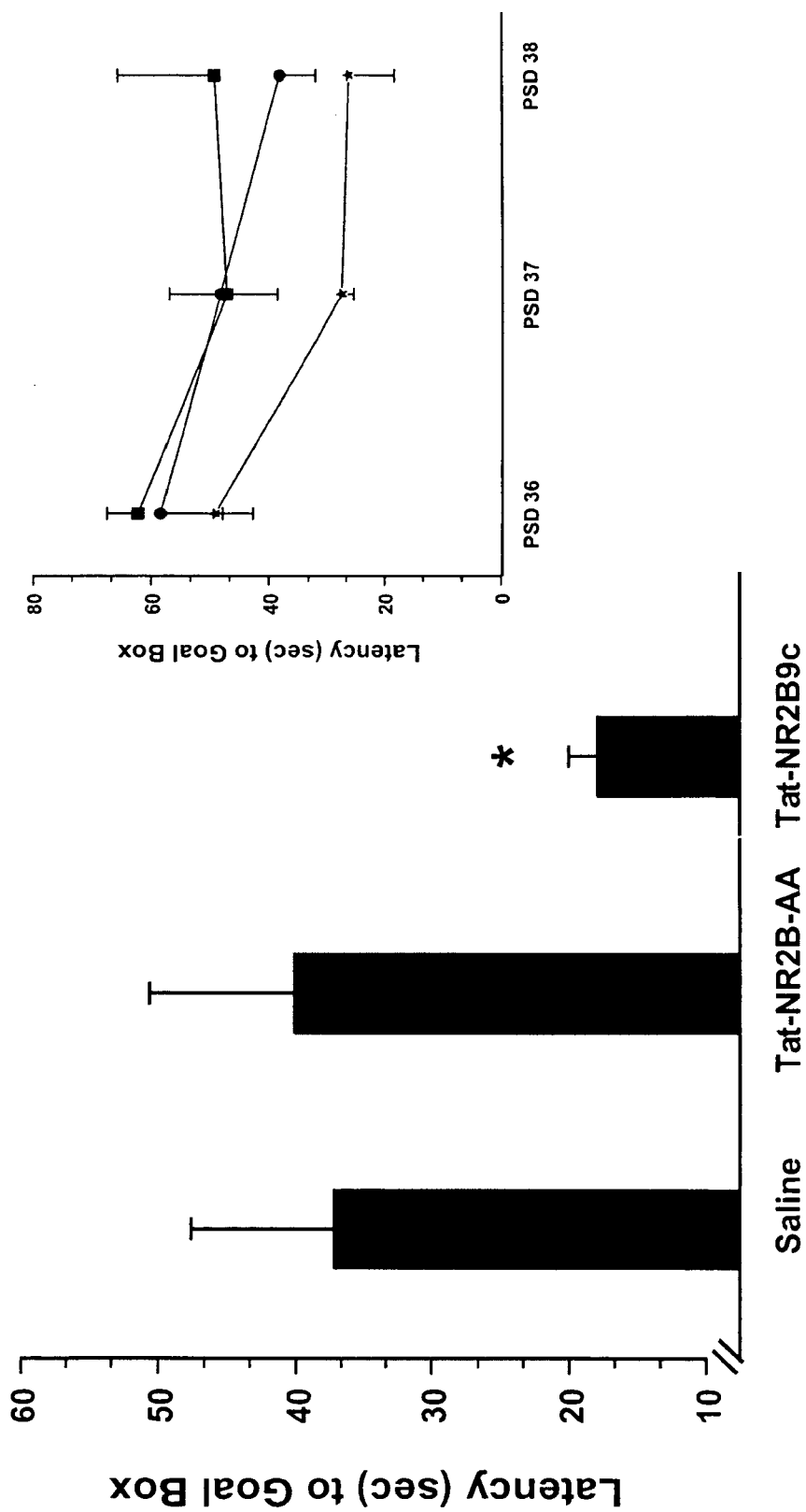
FIG. 11. A. Performance in the Barnes Circular maze approximately 1 month post-MCAo. Rats treated with Tat-NR2B9c performed significantly better on retest than rats in the combined control group [t(23)=1.86, p<0.01] and had consistently lower latencies during the acquisition phase of the test (insert)[ANOVA, p=0.077]. B. Performance in the Morris Water maze at approximately 2 months post-MCAo. Tat-NR2B9c treated rats spent significantly more time in the quadrant previously occupied by the platform during probe trial testing than combined controls [t(28)=2.07, p=0.024] but were not different on the acquisition phase of the task (insert).
Figure 11B:
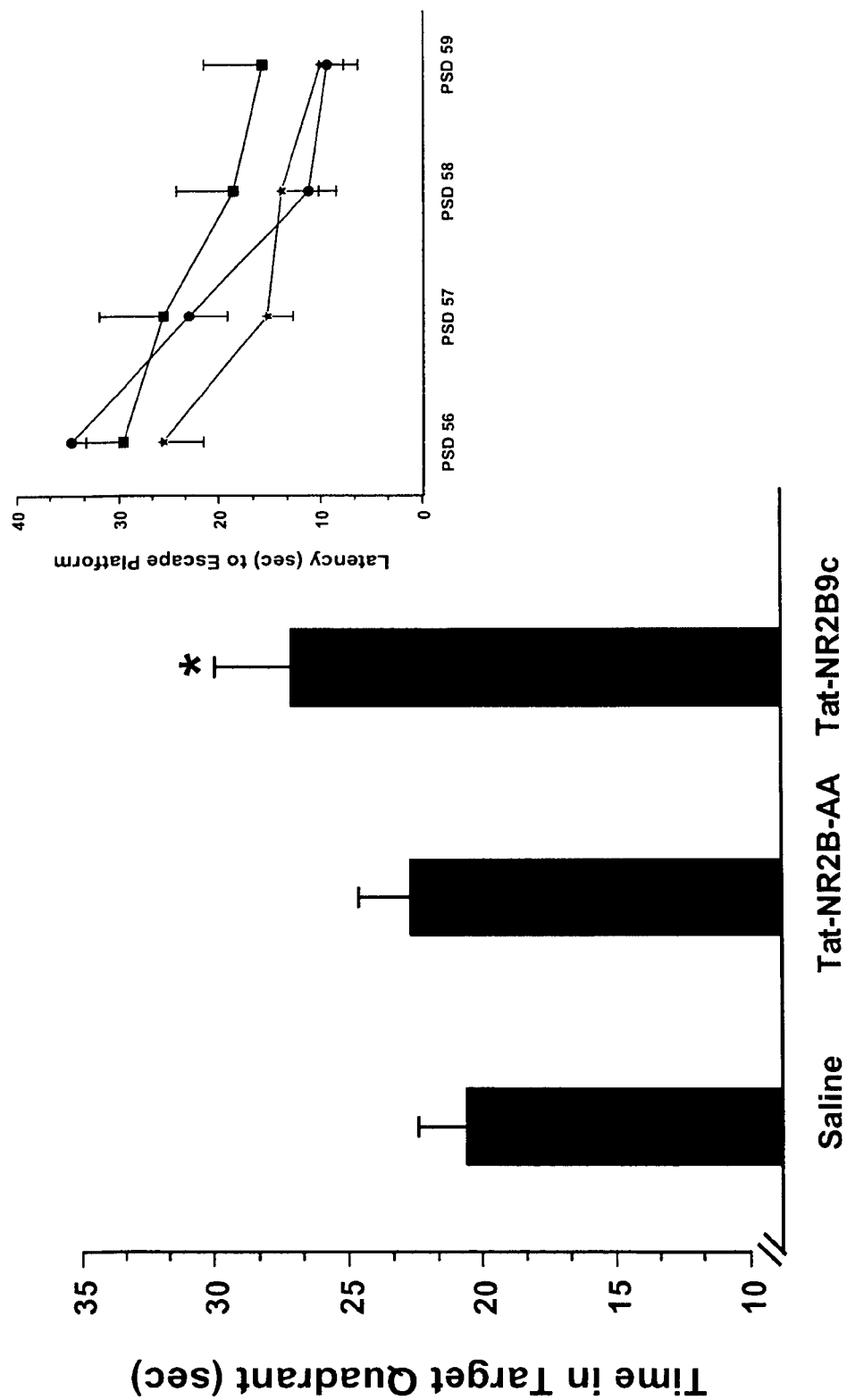

Long-term cognitive deficits are among the most common disabilities in surviving stroke patients. Loss or retention of cognitive function in response to drug treatment in these studies was measured using two well established, but quite different, tests; the Barnes circular maze (days 36-45)(Barnes, 1979) and the Morris water maze (days 56-61)(Morris 1984). Rats treated with NR2B9c had consistently shorter mean escape latencies during the acquisition phase of Barnes maze testing (FIG. 11A insert); an effect that approached significance when data from both control groups were combined (19)[F (1,28)=3.37, p=0.077). On retest (to assess memory), however, TAT-NR2B9c treated rats performed significantly better than both saline and NR2B-AA rats (FIG. 11A) [t(23)=1.86, p<0.01 relative to combined control). A comparable effect was found in the Morris water maze when animals were tested approximately 2 months post-injury. No significant group differences were observed in the acquisition phase of the task (FIG. 11B insert) but compared to combined control rats (20), animals injected with a single dose of TAT-NR2B9c three hours post-ischemia had significantly reduced memory deficits as evidenced by increased time in the target quadrant (FIG. 11B)[t(28)=2.07, p=0.024].

Figure 12A:
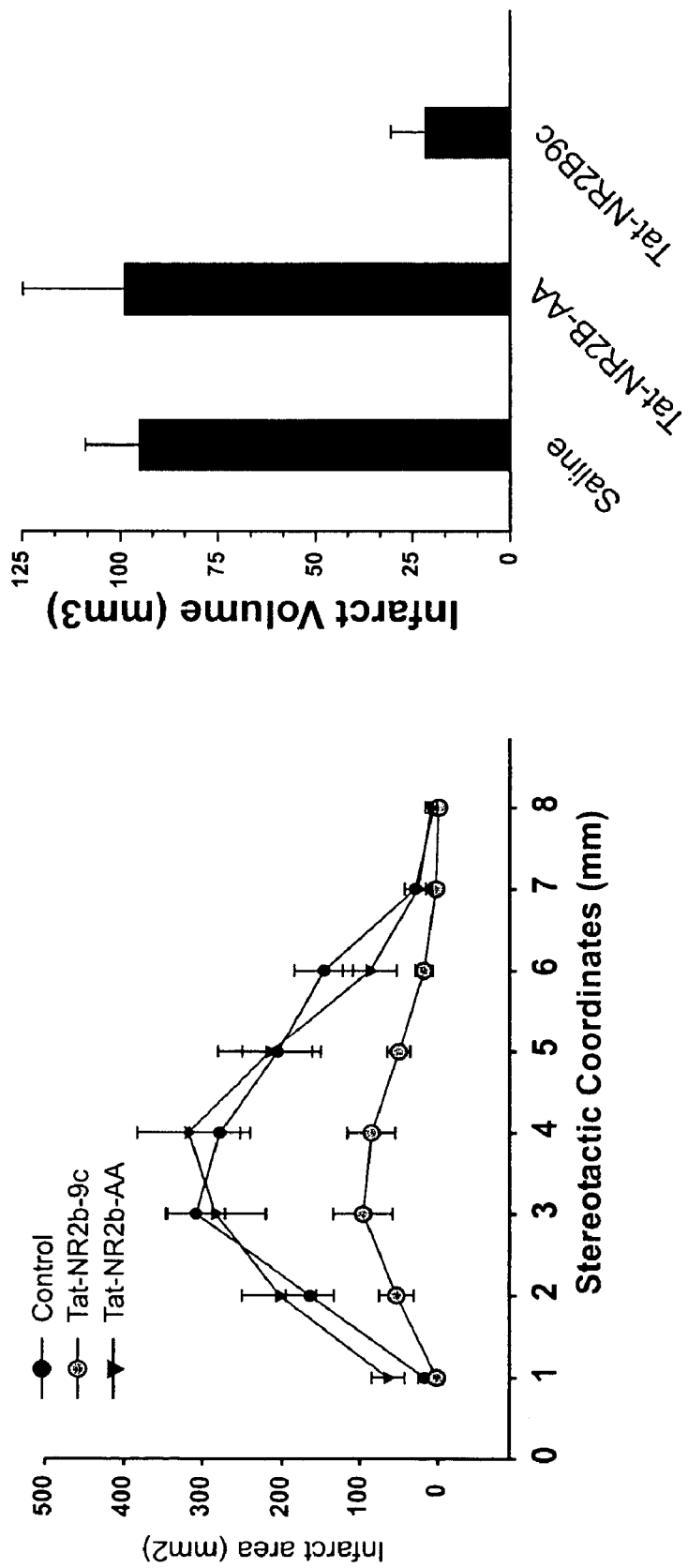
FIG. 12. Post-mortem analysis 62 days post-MCAo reveals that rats treated with TAT-NR2B9c had significantly reduced infarct areas and infarct volumes [ANOVA, F (2,27)=5.72, p=0.0085] relative to both saline and mutated Tat peptide controls.
Figure 12B:
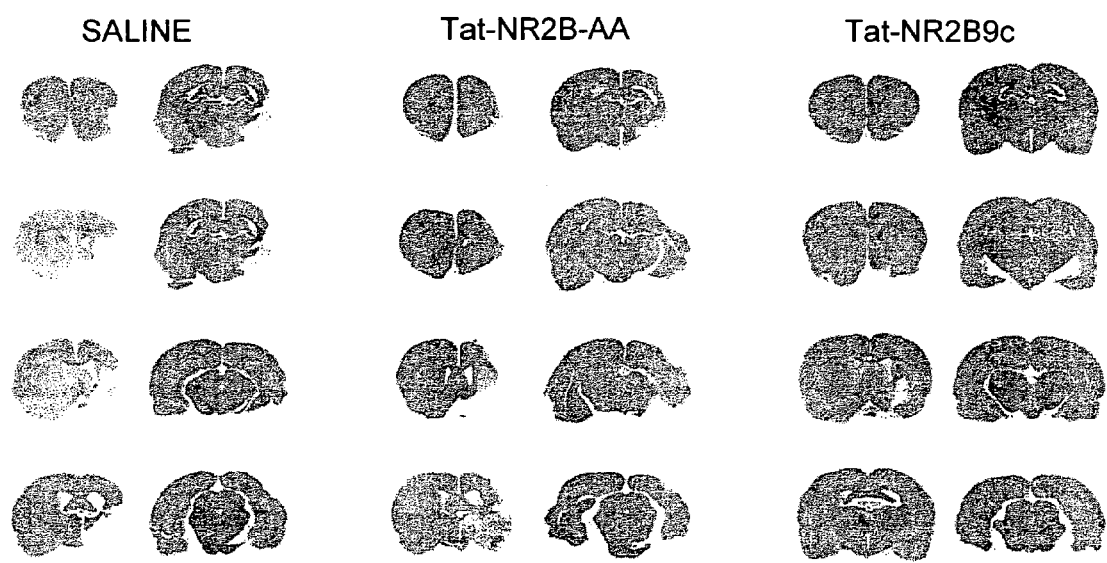

Lastly, I euthanized all rats at 62 days post-surgery and quantified cerebral infarct volume. Treatment with TAT-NR2B9c reduced total infarct area and volume relative to TAT-NR2B-AA and saline (FIG. 12)[F [2,27]=5.72, p=0.0085].

My results show, for the first time, that post-ischemic treatment with an exogenous peptide that perturbs NMDAR-PSD 95 interactions results in significant functional neuroprotection and significantly reduced cerebral infarct volumes for up to 2 months in rats. Rats treated with this peptide display no abnormal behaviour following acute exposure within this dosage range, and no long-term adverse effects were observed during these studies, consistent with the presumed mechanism of action of this compound. Targeting of NMDAR-PSD 95 interactions appears to be a practical future strategy for treating stroke and possibly other neurological disorders.

Next, I investigated the effects of different doses of a single i.v. injection of TAT-NR2B9c (0, 0.03, 0.3, 1 or 3 mmoles/g) on the size of the cerebral infarct. The peptide was injected 3 hours after the onset of the stroke, and the infarction size was measured 24 hours after stroke onset using histological analysis of infarction volumes. The experiments were carried out in adult male Sprague-Dawley rats subjected to transient middle cerebral artery occlusion (MCAO) for 90 minutes by the intraluminal suture method (Aarts et al., 2002). Animals were fasted overnight and injected with atropine sulfate (0.5 mg/kg IP). After 10 minutes anesthesia was induced with 3.5% halothane in a mixture of nitrous oxide and oxygen (Vol. 2:1) and maintained with 0.8% halothane. Rats were orally intubated, mechanically ventilated, and paralyzed with pancuronium bromide (0.6 mg/kg IV). Body temperature was maintained at 36.5-37.5° C. with a heating lamp. Polyethylene catheters in the femoral artery and vein were used to continuously record blood pressure and to sample blood for gas and pH measurements. Transient MCAO was achieved for 90 min by introducing a poly-L-lysine-coated 3-0 monofilament nylon suture (Harvard Apparatus) into the circle of Willis via the internal carotid artery, effectively occluding the middle cerebral artery. This produces an extensive infarction encompassing the cerebral cortex and basal ganglia. Three hours after stroke onset, the animals were treated with either saline, or with 0.03, 0.3, 1 or 3 nmoles/g Tat-NR2B9c by a single intravenous bolus injection. Physiological parameters (body temperature, blood pressure, blood gases) were monitored and maintained throughout the experiment. All experimental manipulations and analyses of data were performed by individuals blinded to the treatment groups. The extent of cerebral infarction was measured 24 h after MCAO onset.

In addition, one group of animals received 6 mg/kg of the NR2B subunit-selective antagonist Ro25-6981 (Mutel et al., 1998; Loschman, P.A., et al., 2004), as members of the NR2B subunit-selective NMDA receptor antagonists such as Ifenprodil and Eliprodil (Williams, 2001; Nikan and Meltzer 2002) have been tested in human clinical trials in stroke. However, antagonists of NMDA receptors are effective primarily if administered before, or within minutes after the onset of a stroke. Therefore, in order to ensure effectiveness in the animal model, this antagonist was administered to the animals one hour prior to the stroke onset.

Figure 13A:
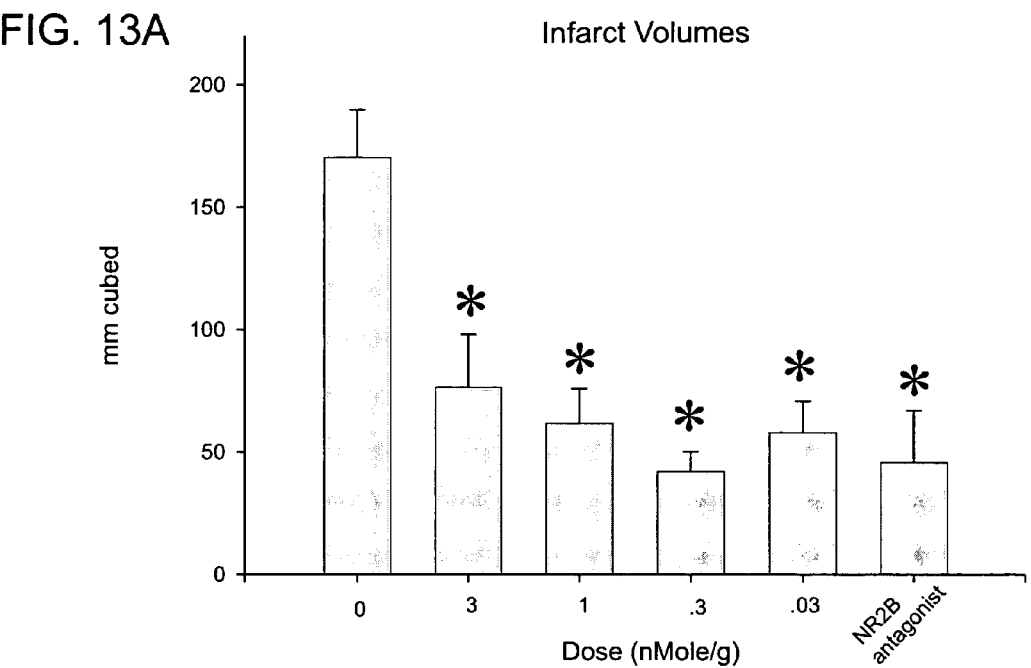
FIG. 13. Effects of the different doses of Tat-NR2B9c (administered 3 h after stroke onset) and of the NR2B antagonist Ro25-6981 (administered at 6 mg/kg 1 h before the stroke) on the infarct volume (FIG. 13A) and on the infarct areas in serial coronal sections of the rat brains (FIG. 13B). There was a significant reduction in infarct size in all animal groups treated with the agents at all doses as compared with the control (0 nmol/g) dose (ANOVA, F=8.087, P<0.001). Moreover, there were no differences in efficacy between the different doses, indicating that 0.03 nmole/g, a 100-fold lesser dose of Tat-NR2B9c than that administered in previous studies, is equally effective. Moreover, Tat-NR2B9c, administered 3 h after the stroke onset was as effective as Ro25-6981 administered 1 h before the stroke. Asterisks indicated differences from saline (0 nmol/g) control (Bonferroni t-test, P<0.004).
Figure 13B:
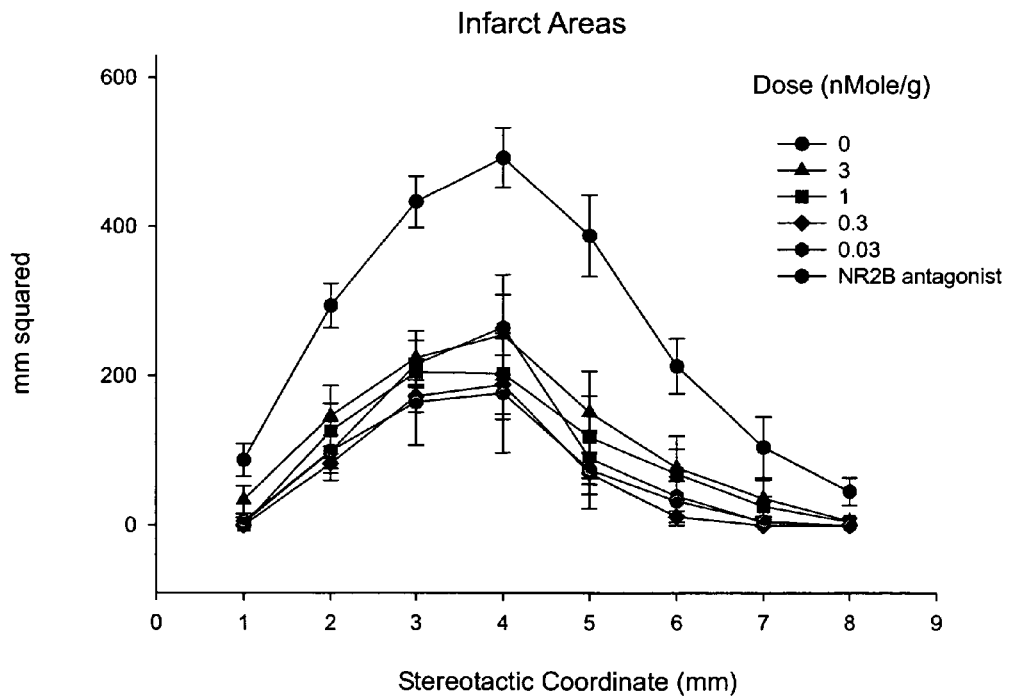

FIG. 13 shows the effects of the different doses of Tat-NR2B9c (administered 3 h after stroke onset) and of Ro25-6981 (administered 1 h before the stroke) on the infarct volume (FIG. 13A) and on the infarct areas in serial coronal sections of the rat brains (FIG. 13B). There was a significant reduction in infarct size in all animal groups treated with the agents at all doses as compared with the control (0 mmol/g) dose (ANOVA, F=8.087, P<0.001). Moreover, there were no differences in efficacy between the different doses, indicating that 0.03 nmole/g, a 100-fold lesser dose of Tat-NR2B9c that that administered in previous studies, is equally effective. Moreover, Tat-NR2B9c, administered 3 h after the stroke onset was as effective as Ro25-6981 administered 1 h before the stroke. These data indicate that Tat-NR2B9c has a very wide therapeutic range and, given its tolerability at the higher doses, it is a useful approach to the treatment of stroke in humans.

TBI can result in neurological impairment due to immediate CNS tissue disruption (primary injury), and surviving cells may be secondarily damaged by mechanisms triggered by the primary event, leading to further damage and disability (Teasdale and Graham, 1998; Amar and Levy, 1999).

Unlike in severe TBI, neurons in mild TBI are less affected by primary mechanical disruption, but may be vulnerable to subsequent events. Accordingly, to study secondary injury mechanisms in vitro, I developed a model of sublethal stretch-induced injury in cultured cortical neurons (Arundine et al., 2003). The sublethal stretch approach removes the confounding effects of neuronal loss from primary tissue disruption. I have extensively characterized this model. In brief, sublethally stretched neurons maintained cell membrane integrity, viability, and electrophysiological function. However, stretching evoked in the neurons a heightened vulnerability to subsequent challenges with L-glutamate or NMDA. This heightened vulnerability was specifically mediated by NMDA receptors (NMDARs), as stretched neurons did not become more vulnerable to either AMPA/kainate toxicity or to that induced by a $Ca^{2+}$ ionophore. Stretch-enhanced vulnerability to NMDA occurred independently of endogenous glutamate release, but required $Ca^{2+}$ influx through NMDARs. Stretch did not affect the electrophysiological properties of NMDARs nor excitatory synaptic activity, indicating that specificity of enhanced vulnerability to NMDA involves postsynaptic mechanisms downstream from NMDARs. The data indicated that sublethal in-vitro stretch injury triggers distinct secondary injury signaling pathways rather than causing a generalized increase in vulnerability to secondary insults.

Sublethal Stretch Injury Model.

To examine mechanisms that render neurons vulnerable to damage after mechanical injury, I developed an in-vitro model of sublethal stretch (detailed in (Arundine et al., 2003)). This was achieved in cortical neuronal cultures grown on a flexible substrate that could be stretched to a defined extent and duration using a commercially available device (Methods). The stretch injury severity was titrated downwards until no cells died post-insult for 24 h observation period (sublethal injury). This approach eliminates the confounding effects mechanical cell disruption (primary injury) on any damage that might be imposed by a subsequent insult (secondary injury). The cells were stretched to 130% of their original length for 1s. Preliminary studies demonstrated that at static peak deflection, the neurons and dendrites remained attached to the culture membrane (data not shown; see also (Smith et al., 1999)). Therefore, the membrane stretch likely correlated with cell stretch. I did not calculate the culture membrane strain, an estimate of the strain imparted to the cells, as the latter may differ from the strain of the underlying substrate. Sublethally stretched cells did not take up the cell viability indicator propidium iodide (PI), were morphologically unchanged, and exhibited normal whole-cell ionic currents (Arundine et al., 2003).

Stretch Renders Neurons More Vulnerable to Secondary Insults with NMDA.

Figures 14A, 14B, 14C:
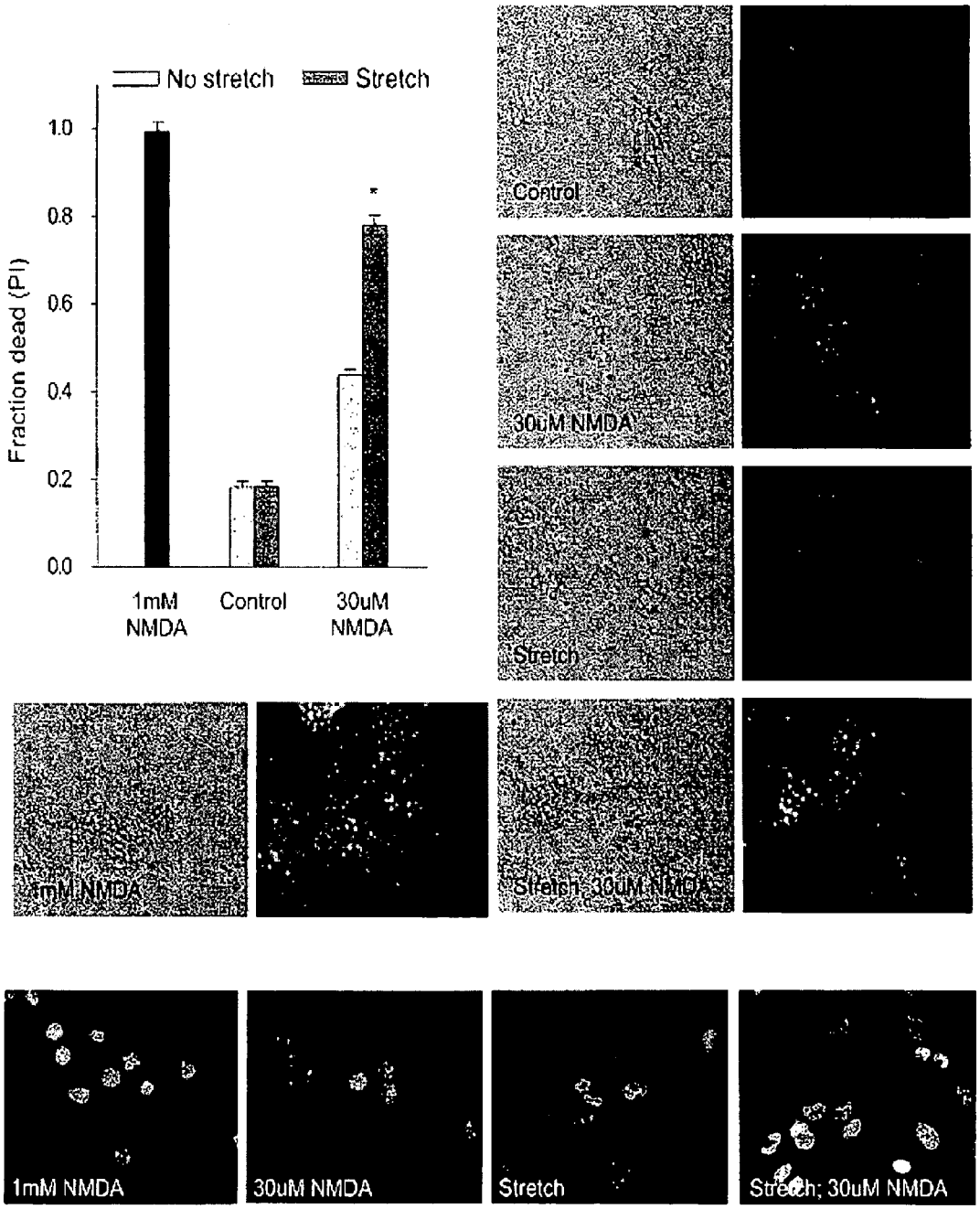
FIG. 14. Sublethal stretch injury renders cortical cultures vulnerable to low concentrations of NMDA. NMDA was applied for 1 h within 10 min of stretch. A. Effects of NMDA at the indicated concentration with or without prior stretch (130% for 1s). Cell death was measured at 20 h. Asterisk: difference from unstretched ($t_{61}$=13.23, p<0.001). Bars: mean±SE of 27-34 cultures from 3 separate dissections. B. Representative phase contrast and PI fluorescence images of unstretched and stretched cultures 20 h after challenge as indicated. C. High-magnification of Hoechst-stained neuronal nuclei 20 after the indicated challenge. NMDA (1 mM or 30 μM) applied to unstretched cultures did not affect the round nuclear morphology (white arrows). However, stretch caused condensation and irregularity of nuclear morphology (open arrows). Images were obtained using identical excitation, emission, and camera gain settings (Representative of 3 separate experiments).

Although stretch to 130% for 1 s (hereafter referred to as "stretch") did not kill the neurons, it made them more vulnerable to a subsequent application of NMDA at concentrations that were tolerated by most unstretched controls (FIG. 14A, B). I have shown previously that this enhanced vulnerability to a second challenge was not ubiquitous to all types of insults. Rather, stretched neurons exhibited an enhanced mortality when challenged with agonists of NMDA receptors (NMDA and L-glutamate), but not when challenged with selective AMPA/kainate receptor agonists, or with a $Ca^{2+}$ ionophore. Moreover, the enhanced vulnerability of stretched neurons to NMDA was not due to synaptic or non-synaptic release of excitatory amino acids from stretched cells, nor due to alterations of NMDA receptor function (Arundine et al., 2003).

Sublethal Stretch Injury Produces Irregular Nuclear Morphology.

To examine the effects of stretch on nuclear morphology, the cells were stained with the cell-permeant nuclear dye Hoechst 33258 (Methods). Nuclei of unstretched neurons exposed to lethal (1 mM) or sublethal (30 μM) NMDA concentrations remained round (FIG. 14C, white arrows). However, neurons exposed to sublethal stretch or to the lethal combination of stretch and 30 μM NMDA exhibited irregular and condensed nuclei (FIG. 14C-*red* arrows). This morphology has been interpreted as representing apoptosis in some studies examining the effects of low NMDA concentrations (Bonfoco et al., 1996; Bonfoco et al., 1995), and in past studies of in-vitro traumatic neuronal damage (Shah et al., 1997). Moreover, apoptosis has been implicated as a causative death mechanism in many animal studies of traumatic brain injury (Rink et al., 1995; Clark et al., 1997; Conti et al., 1998; Newcomb et al., 1999; Raghupathi et al., 2000; Wennersten et al., 2003). As NMDA alone did not produce irregular nuclei even at lethal (1 mM) concentrations, I questioned whether stretch biased the neurons to an apoptotic death. Thus, I next sought additional markers of apoptosis in these cells.

NMDA Challenge to Sublethally Stretched Neurons Produces DNA Fragmentation.

Figure 15A:
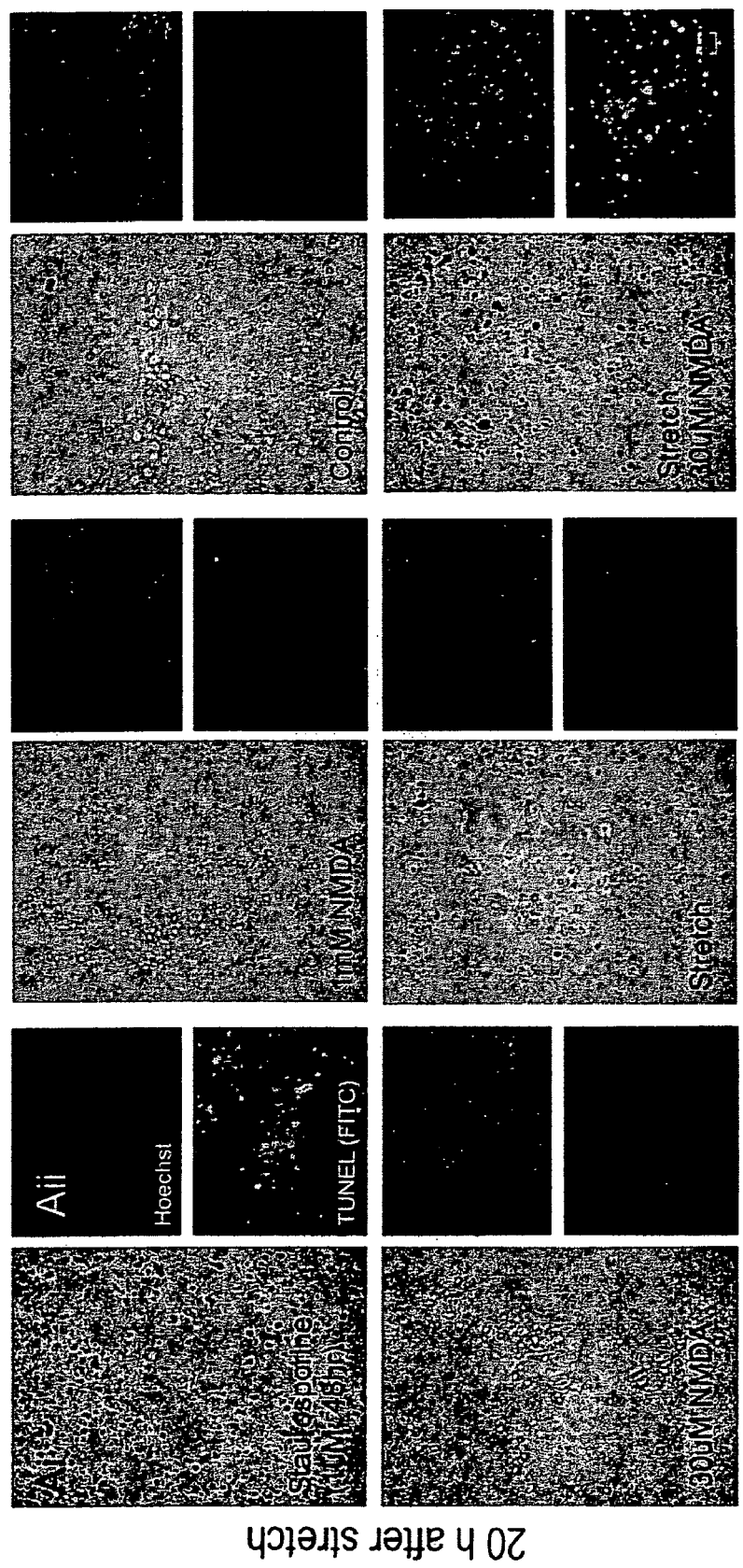
FIG. 15. Challenging sublethally-stretched neurons with low NMDA concentrations produces DNA damage. NMDA was applied for 1 h within 10 min of stretch A. TUNEL staining 20 h post-injury under the indicated conditions using the DAB (Ai) or FITC (Aii) methods. Nuclei in (Aii) were also counterstained with Hoechst. Each panel is representative of 3 experiments. B. Quantification of TUNEL staining at 20 h by each method. TUNEL positive cells were normalized to total cell number. Approximately 100-200 cells were counted per culture. Compared with unstretched controls, treatment with 1 μM staurosporine for 48 h and stretch+NMDA for 1 h resulted in increased TUNEL staining (Staurosporine: FITC-$t_{18}$=7.63, p<0.0001; DAB-$t_{53}$=30.70, p<0.0001, Stretch+NMDA: FITC-$t_{29}$=10.298, p<0.0001; DAB-$t_{83}$=23.923, p<0.0001). Treatment with NMDA alone (30 μM-1 mM) or stretch alone did not result in increased TUNEL staining. Asterisks: difference from unstretched control (Bonferroni t-test, p<0.05). Bars represent the mean±SE of 4-8 fields in each of 3 cultures in each of 3 (FITC) or 6 experiments (DAB). C. Staurosporine and stretch+30 μM NMDA, but not 1 mM NMDA alone or stretch alone, induce DNA laddering (arrowheads) 20 h post-insult. Representative of 3 separate experiments. D. Tunnel staining does not occur within 1 h of stretch. Phase-contrast and fluorescent TUNEL stain images taken 1 h after sham (no stretch) or stretch. Representative of 3 separate experiments.
Figures 15B, 15C:
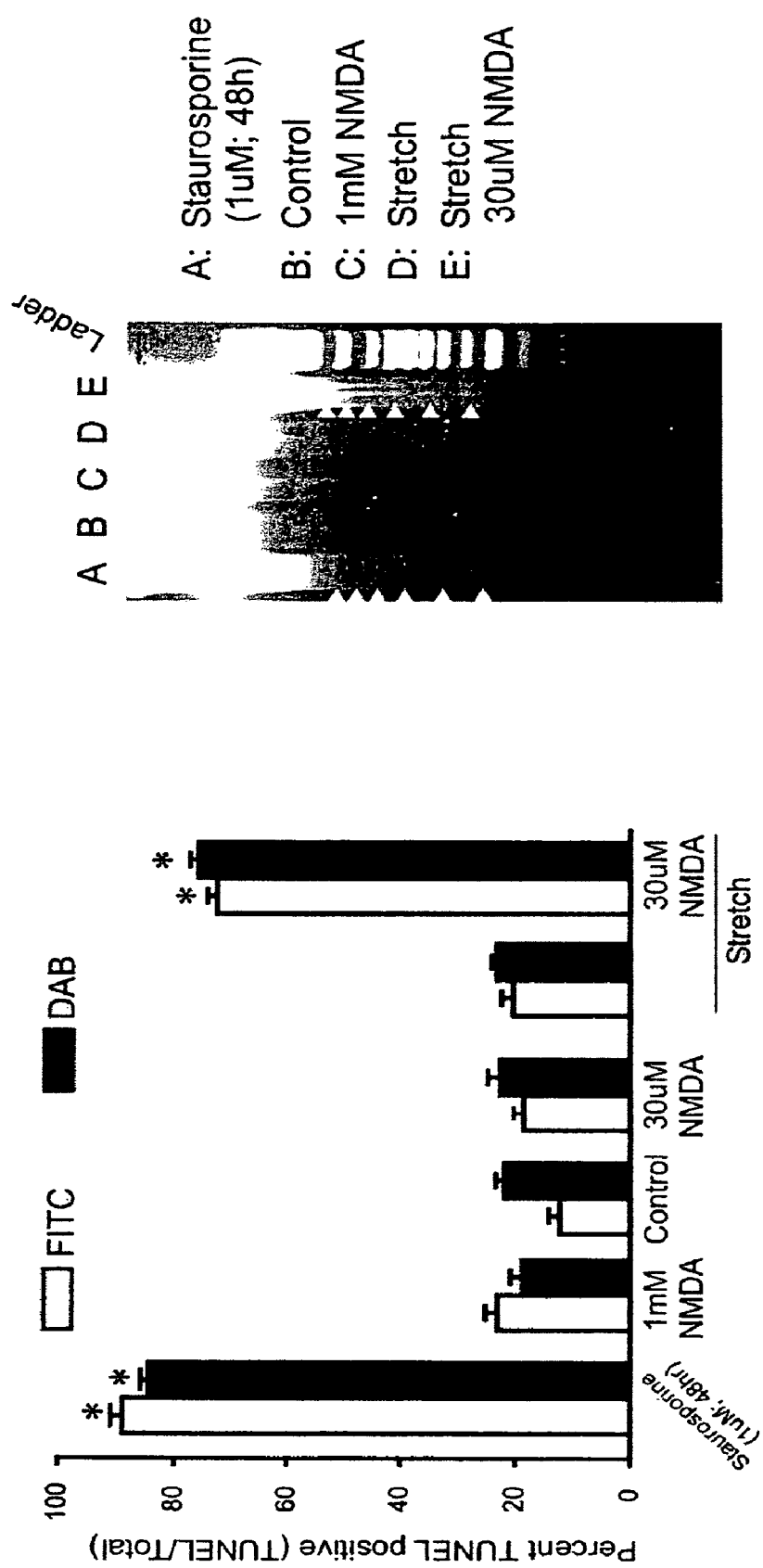

Internucleosomal DNA fragmentation is an important biochemical feature of apoptosis, and can be determined using in situ nick-end labeling (TUNEL) or by DNA fragmentation analysis by gel electrophoresis (Gavrieli et al., 1992; Gerschenson and Rotello, 1992; Allen et al., 1997). I used both techniques to detect DNA fragmentation in stretched cells 20 h after the insult (FIG. 15A-C). As a positive control for apoptosis the cultures were treated with staurosporine (1 μM for 48 h) as this is an established method for triggering an apoptotic death in cortical cultures (Yu et al., 1997; Budd et al., 2000). TUNEL staining was observed only in staurosporine treated cultures, and in stretched cultures that were also challenged with NMDA (FIG. 15A,B). Cultures exposed to the non lethal conditions of sham (unstretched controls), stretch alone, or 30 μM NMDA without stretch, did not TUNEL stain (FIG. 15A,B). Interestingly, cultures exposed to 1 mM NMDA, which is lethal (FIG. 14A), also failed to TUNEL stain (FIG. 15A,B), a finding consistent with a lack of effect of 1 mM NMDA on nuclear morphology (FIG. 14C).

Complementary results were obtained when DNA fragmentation was evaluated by DNA gel electrophoresis: DNA ladders suggestive of internucleosomal DNA fragmentation were only observed in staurosporine treated positive controls, and in stretched neurons that were also treated with 30 μM NMDA (FIG. 14C). These results show that DNA fragmentation was uniquely displayed by neurons undergoing the combination of sublethal stretch followed by NMDA at concentrations that would have been tolerated by most cells in the absence of prior stretch. A lethal excitotoxic challenge without stretch was insufficient to produce DNA fragmentation.

Figure 15D:
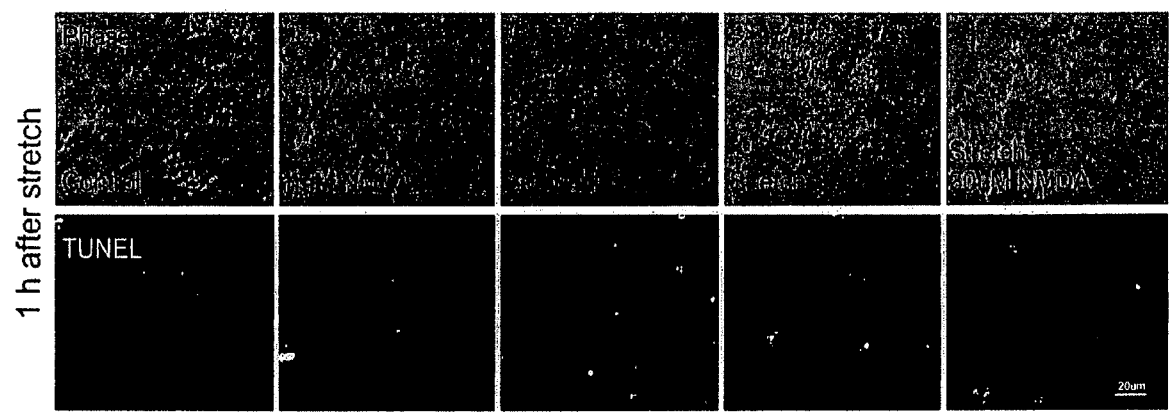

Since stretch is a physical insult, I questioned whether the mechanical deformation of nuclei might directly induce chromatin damage at the weakest points (internucleosomal breaks), thus initiating programmed cell death. To test this, I surmised that if the DNA damage is mechanically induced, then it should be evident immediately after stretch. Accordingly, I examined cells at 1 h post-injury by TUNEL staining. However, TUNEL positivity 1 h after stretch was no different than in unstretched controls (FIG. 15D). Similar results were obtained using DNA gel electrophoresis (not shown). Thus, it is unlikely that the DNA fragmentation induced after stretch+NMDA is caused by direct mechanical damage.

Although apoptosis causes DNA fragmentation, the converse is not necessarily true. For example, in traumatic head injury, DNA fragmentation analysis (TUNEL staining or gel electrophoresis) was of no value because these tests were positive for both processes both necrotic and apoptotic cells (Ishimaru et al., 1999). This is likely because DNA of necrotic cells also undergoes degradation, and reacts with the terminal transferase used in the TUNEL assay (Charriaut-Marlangue and Ben Ari, 1995; Grasl-Kraupp et al., 1995). Thus, to seek further evidence of apoptosis I next examined other indicators of apoptotic pathways.

Role of Classical Apoptosis in DNA Fragmentation of Sublethally Stretched Neurons Exposed to NMDA.

Previous studies have suggested that in models of glutamate toxicity, traumatic brain injury and ischemia, internucleosomal DNA fragmentation is mediated by pathways involving effector caspases, including caspase 3 (Tenneti et al., 1998; Eldadah and Faden, 2000; Pike et al., 2000). In response to various apoptotic stimuli, the pro-form of caspase 3 (i.e., inactive form) is cleaved into a smaller fragment (active caspase 3) that has proteolytic activity resulting in eventual endonuclease activation and DNA fragmentation (Enari et al., 1998; Sakahira et al., 1998; Yakovlev et al., 2001). Thus, I questioned whether caspase-associated pathways were involved in the DNA fragmentation observed after stretch.

Figure 16A:
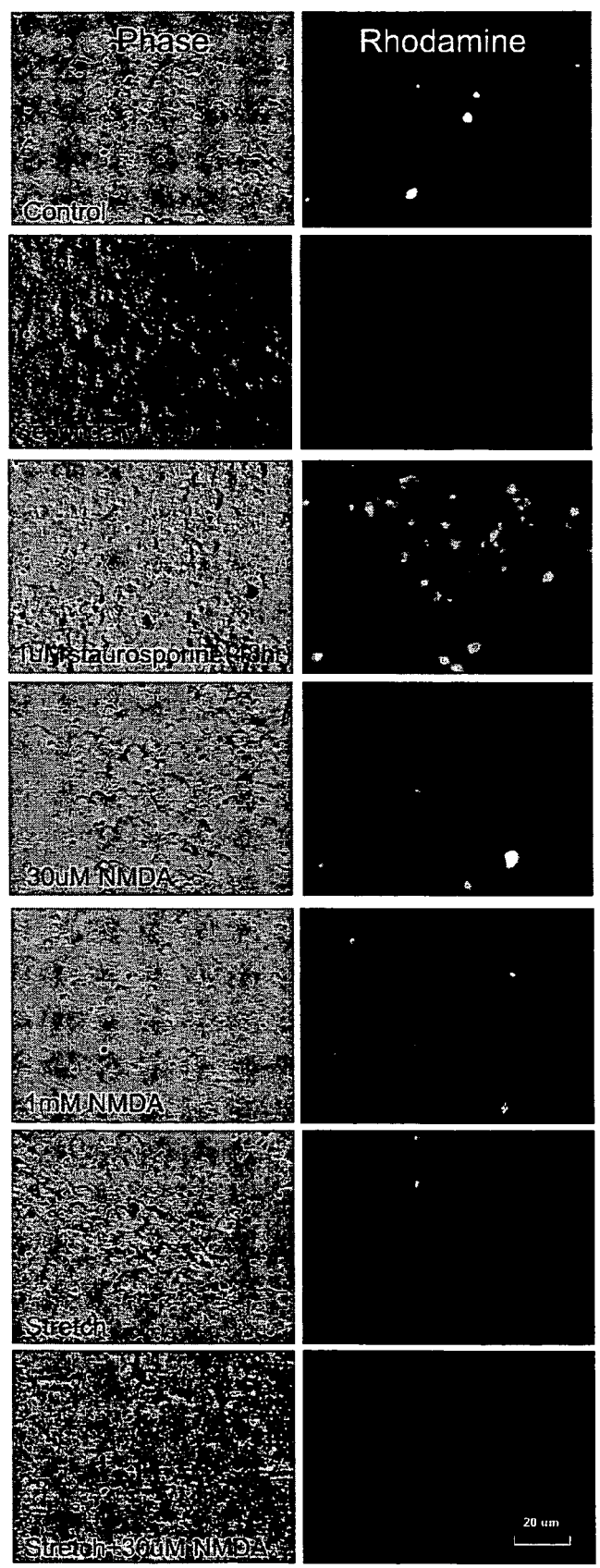
FIG. 16. Stretch +NMDA dependent cell death is not caspase mediated. A. Active caspase-3 immunoreactivity in fixed cortical neuronal cultures at 20 h after the insult using the indicated conditions. Only cultures treated with staurosporine exhibited pronounced active caspase 3 immunofluorescence. Bi. Immunoblot of caspase 3 (both pro- and active/cleaved forms) 20 h after the indicated insult. The pro-caspase 3 form (32 kDa) was detectable under all culture conditions, whereas only cultures treated with staurosporine displayed the active caspase-3 band (17 kDa). Representative of 3 experiments. Bii. Immunoblot of the time course of caspase 3 expression (both pro- and active/cleaved forms) after stretch with or without NMDA. While pro-caspase 3 (32 kDa) was detectable at all time points, neither stretch nor stretch+30 μM NMDA induced active caspase-3 (17 kDa) at any time-point. Representative of 2 experiments. C. Stretch-induced vulnerability to NMDA toxicity is not attenuated by the pan caspase inhibitor, zvadFMK. Treatment with 200 μM zvadFMK for 48 h attenuated staurosporine-induced death by 47% ($t_{17}$=9.561, p<0.001). Asterisks: difference from paired control, Bonferroni t-test, p<0.05). Bars: mean±SE of 9-13 cultures obtained from 3 separate dissections. D. zvadFMK treatment did not reduce DNA laddering (arrowheads) 20 h following NMDA challenge of stretched cultures (representative of 2 experiments).

First, I used immunofluorescence to examine the cultures for the presence of active caspase 3 20 h after stretch, a time point at which I found increased internucleosomal DNA fragmentation in neurons exposed to stretch+NMDA (FIG. 15A-C). Although cultures exposed to staurosporine (positive control) stained for active caspase 3, I failed to observe a concomitant increase in active caspase 3 under any other conditions (FIG. 16A). To examine this further I next checked for the presence of active caspase 3 by immunoblotting. However, at 20 h after stretch, there was no evidence of the cleaved form of caspase 3 (17 kDa; FIG. 16Bi). All conditions were immunopositive for the pro-form of caspase 3, as represented by 32 kDa band (FIG. 16Bi). Next, I tested whether active caspase 3 was detectable at earlier time points in stretched neurons treated with 30 μM NMDA. However, this also failed to reveal evidence of active caspase 3 at 1 h, 4 h, 8 h or 12 h following the insult.

Figure 16C:
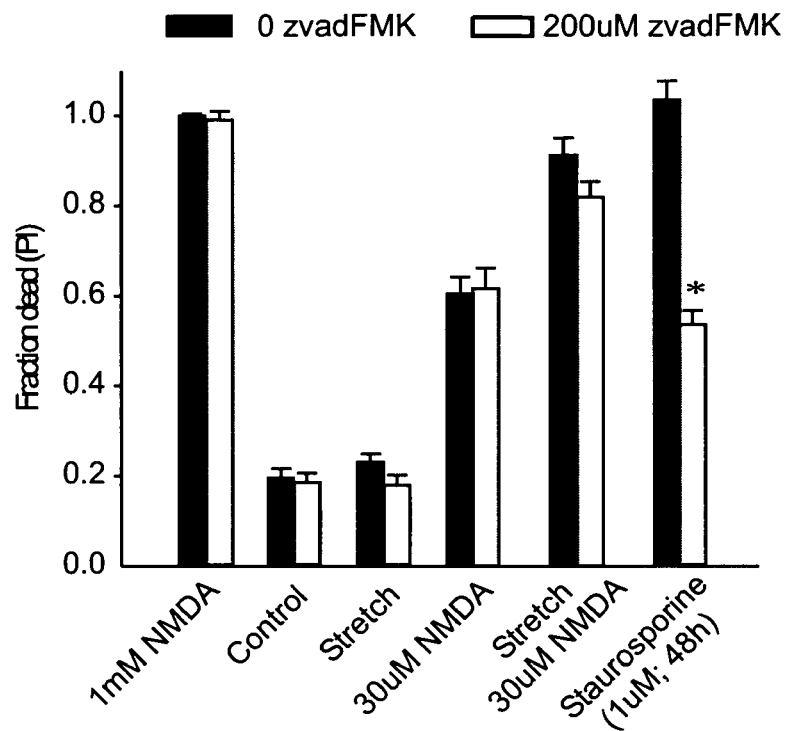
Figure 16D:
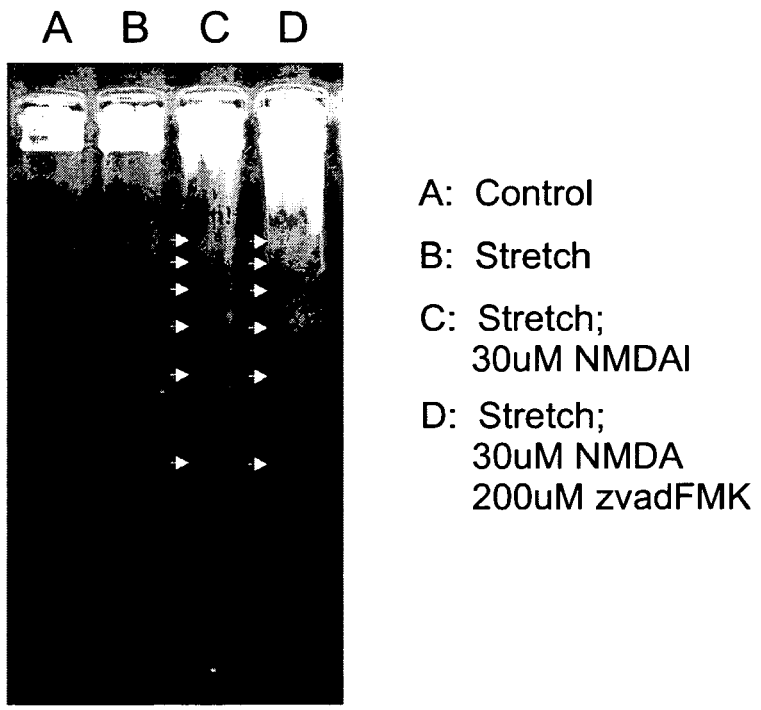

Though active caspase 3 was not detected, I next questioned whether other caspases might have been involved. Thus, I examined the effects of the pan caspase inhibitor z-VAD-FMK (Fearnhead et al., 1995). Previous studies suggest that z-VAD-FMK treatment of cortical neurons protects them from NMDA-induced apoptosis (Charriaut-Marlangue and Ben Ari, 1995; Grasl-Kraupp et al., 1995; Tenneti et al., 1998). Indeed, I found that cell death in cultures treated with staurosporine (1 μM; 48 h) can be significantly reduced when by pretreatment with 200 μM z-VAD-FMK (FIG. 16C). 200 μM z-VAD-FMK was not toxic to unstretched cultures or to those that underwent stretch alone. However, when treating stretched cultures with both 301 μM NMDA and z-VAD-FMK I found no significant reduction in cytotoxicity (FIG. 16C). Similarly, z-VAD-FMK did not reduce DNA fragmentation of neurons exposed to stretch+NMDA as measured by DNA gel electrophoresis (FIG. 16D). Taken together, these results suggest that caspase-mediated apoptosis is unlikely to explain the DNA fragmentation observed in sublethally stretched neurons challenged with NMDA.

Role of Caspase-Independent Apoptosis in DNA Fragmentation of Sublethally Stretched Neurons Exposed to NMDA.

In addition to caspase-mediated apoptosis there also exist caspase-independent mechanisms of DNA degradation. These are initiated by the cytoplasmic release of mitochondrial proteins such as endonuclease g (endo g) or apoptosis inducing factor (AIF). Endo g is a 30 kD nuclease involved in mitochondrial DNA replication (Cote and Ruiz-Carrillo, 1993). AIF is a mitochondrial flavoprotein (Susin et al., 1999). That translocates from the mitochondria to the nucleus after insults and activates nucleases that induce large-scale DNA fragmentation (>50 kbp) and cell death (Yu et al., 2003; Lorenzo and Susin, 2004). Released endo g can produce nuclear DNA cleavage directly (Wang, 2001). Recent studies of experimental traumatic brain injury have implicated AIF translocation from mitochondria to cell nuclei in the resulting damage (Zhang et al., 2002).

Figure 17A:
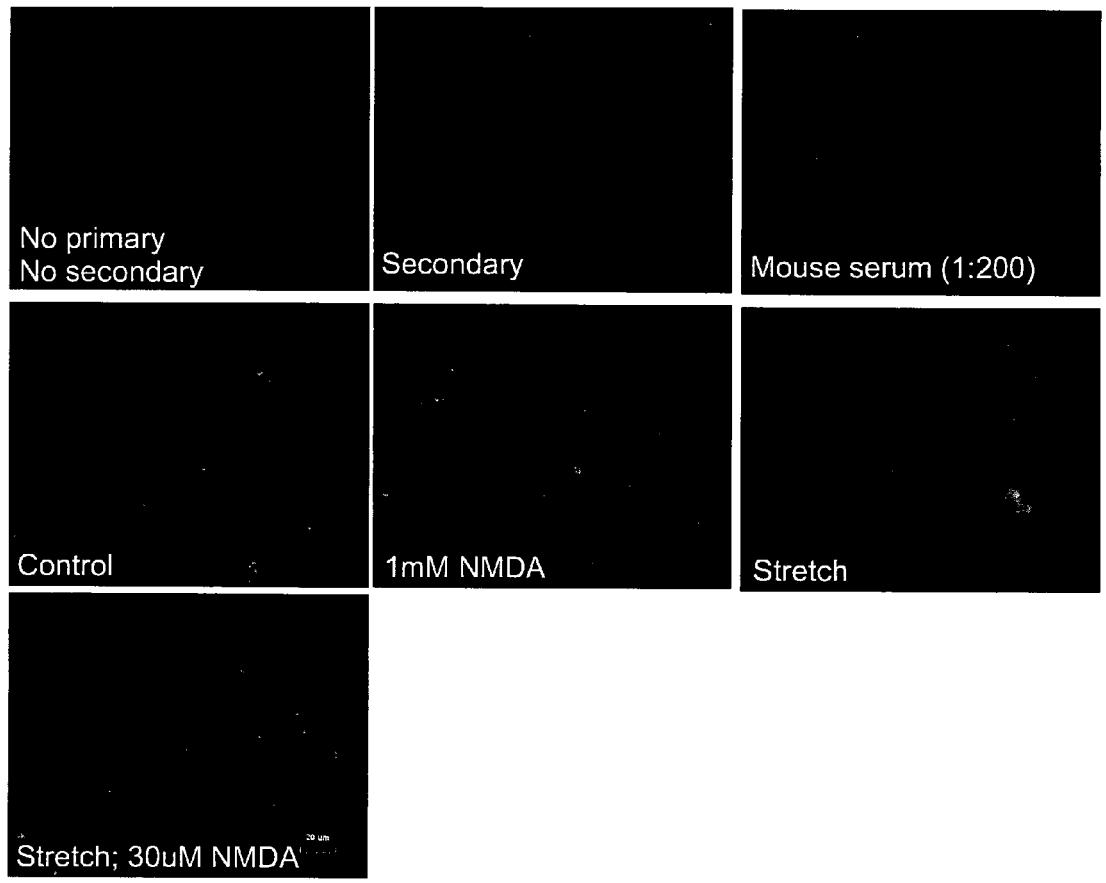
FIG. 17. NMDA challenge of stretched neurons does not cause death through caspase-independent apoptotic pathways. A. Lack of nuclear localization if AIF by Immunofluorescence. AIF was visualized in fixed cultures at 20 h post-insult. B. Immunoblots of AIF (65 kDa), endonuclease g (35 kDa) and NNOS (160 kDa) in nuclear and cytosolic fractions taken from cells at 6 h or 20 h post-insult (stretch ±30 μM NMDA). All cytoplasmic fractions were positive for immunoreactivity of AIF, endonuclease g and NNOS. However, nuclear fractions showed only trace immunoreactivity for any of these proteins (representative of 3 separate experiments). C. Inhibiting calpain does not reduce stretch-induced vulnerability to NMDA toxicity. Cultures were prencubated for 30 min with 10 μM calpain inhibitor III and then exposed to the indicated challenge. Calpain inhibitor III remained in the bath until cell death was measured at 20 h. Calpain inhibition reduced slightly the toxicity of NMDA in all conditions but failed to reduce the vulnerability of the cells to stretch. Asterisks: difference from paired control, Bonferroni t-test, p<0.05. Bars: mean±SE of 9-12 cultures obtained from 3 separate experiments.
Figures 17B, 17C:
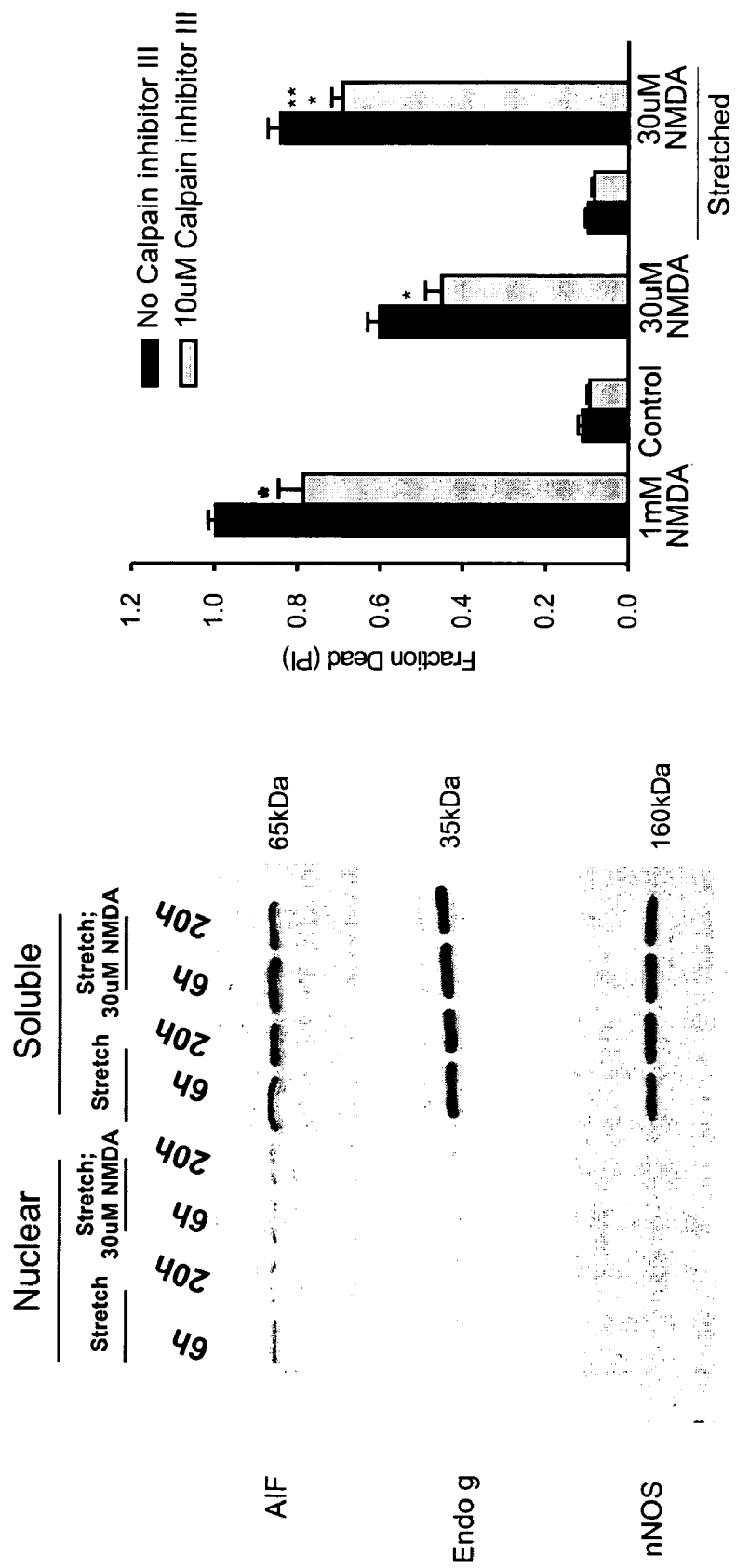

To explore this, I first used immunohistochemistry to determine whether AIF translocated to nuclei (FIG. 17A). Cultures that underwent stretch under the indicated conditions (FIG. 17) were then fixed and stained 20 h post-insult. Although AIF immunofluorescence was detectable in the cells (FIG. 17A-*red*), I could not detect it in the nuclei (FIG. 17A-*blue*), by this means. Therefore, I next used Western blots to determine whether AIF or endo g translocated to the nucleus after stretch. The cultures underwent a stretch insult using the different conditions indicated in FIG. 17B, and were harvested at the indicated times (6 h or 20 h). The tissue was then used to prepare cytoplasmic and nuclear fractions (Methods) in order to examine them separately. These fractions were immunoblotted for AIF and endo g, as well as for neuronal nitric oxide synthase (nNOS). The latter is a cytoplasmic protein not expected in the nuclear fraction, and was thus used as a control for contamination of the nuclear fraction by cytoplasmic proteins. Using this approach, I failed to detect any significant quantities of nuclear AIF or endo g immunoreactivity in any of the stretched cells at either 6 h or 20 h post-injury (FIG. 17B). Thus, it is unlikely that these caspase-independent apoptotic mechanisms explain the DNA fragmentation observed in neurons exposed to stretch+NMDA.

Role of Calpains in Sublethally Stretched Neurons Exposed to NMDA.

The $Ca^{2+}$-activated neutral cysteine protease calpain has long been implicated in excitotoxic damage (Siman and Noszek, 1988; Siman et al., 1989). Calpain activity causes cleavage of cytoskeletal proteins, enzymes, and transcription factors. I have already determined that cytoskeletal protein breakdown is unlikely to explain the enhanced vulnerability of stretched neurons to NMDA (Arundine et al., 2003). However, calpains also share some common substrates with the caspases including cleavage of caspases themselves, thus raising the possibility of protease-induced apoptosis (Gil-Parrado et al., 2002; Danial and Korsmeyer, 2004). Accordingly, I examined whether calpain activation might explain the enhanced vulnerability of sublethally stretched neurons to NMDA. I examined the effect of pre-treating the cortical neuronal cultures with 10 μM z-val-phe-CHO (calpain inhibitor III), provides neuroprotection against UV-induced neuronal death, reduces spectrin degradation in primary cortical neuronal cultures, (McCollum et al., 2002), and reduces hippocampal culture cell mortality from glutamate toxicity (Rami et al., 1997). Calpain inhibitor III was applied 1 h prior to stretch and remained in all solutions thereafter. It had no toxic effects in control or in stretched cultures (FIG. 17C). Consistent with other studies, cells challenged either with 30 μM or 1 mM NMDA were slightly protected by this compound, whether or not they underwent stretch. However, the heightened vulnerability of stretched neurons to NMDA was not reduced through calpain inhibition (FIG. 17C). These data suggest that although calpain activity may partly mediate NMDA toxicity, it does not mediate the increased vulnerability of stretched cultures to NMDA.

These results to this point show that although sublethally stretched neurons exhibit an enhanced vulnerability to NMDA toxicity, irregular nuclear morphology and DNA fragmentation, these are unlikely to be caused by classical or caspase-independent apoptotic mechanisms. Thus, I sought alternative explanations for why sublethal stretch causes neurons to be more vulnerable to subsequent insults with NMDA, and why DNA fragmentation occurs.

Mitochondrial Potential Measurements Predict Survival after Sublethal Stretch.

Mitochondrial dysfunction in cultured neurons has been observed following excitotoxin exposure (Wang and Thayer, 1996; Nicholls and Budd, 1998) and also after in-vitro stretch (Ahmed et al., 2000; Ahmed et al., 2002). Accordingly, I examined whether the lethality of combining sublethal stretch with excitotoxin exposure could be explained by mitochondrial dysfunction as gauged by mitochondrial potential measurements. I used TMRM, a cell-permeant cationic mitochondrial potential indicator. When applied at low concentrations (10 nM), TMRM is extruded from depolarized mitochondria resulting in a net reduction in whole cell TMRM fluorescence (Petronilli et al., 2001). As with many potentiometric probes, TMRM is affected by both mitochondrial and membrane potentials (Ehrenberg et al., 1988; Loew et al., 1993). Accordingly, these experiments can only indicate a relative rather than absolute change in mitochondrial depolarization.

Figures 18A, 18B:
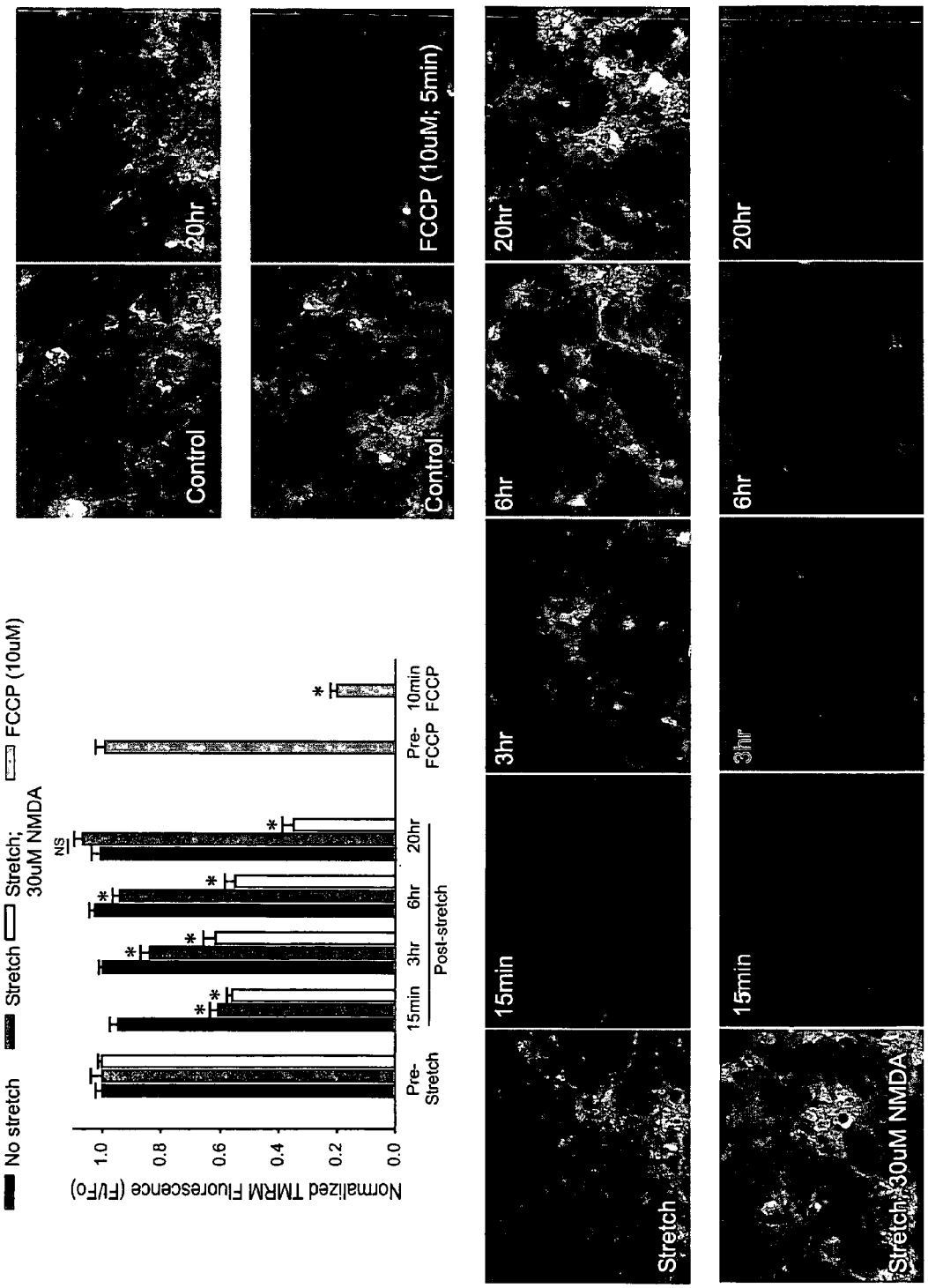
FIG. 18. Stretch causes a reduction in mitochondrial membrane potential. Cultures were pretreated with 10 nM TMRM for 30 min prior to each experiment (Methods). A. Effects of the indicated conditions on TMRM fluorescence at the indicated times post-insult. Bars indicate background-subtracted fluorescence of cultures exposed to an insult (Ft) normalized to background-subtracted TMRM fluorescence in unstretched cells (F0) at the indicated time points. Bars represent mean+SE of 3-4 cultures from N=3 separate experiments. Asterisks: difference from unstretched cultures at the indicated time-point (Bonferroni t-test, p<0.05). B. Representative TMRM fluorescence images from the indicated condition. TMRM fluorescence in cultures exposed to stretch only recovered, whereas TMRM fluorescence from cultures exposed to stretch +NMDA did not. Treatment with the mitochondrial uncoupler FCCP abolished TMRM fluorescence.

In the absence of insults, neurons maintained their mitochondrial potential throughout the 20 h observation period (FIG. 18). As a positive control I applied the protonophore FCCP (101M; 10 min), which causes a profound mitochondrial depolarization and a corresponding loss of TMRM fluorescence (FIG. 18). Cultures exposed to stretch also exhibited a rapid loss of TMRM fluorescence. However, this recovered within hours (FIG. 18). By contrast, in stretched neurons that were subsequently challenged with NMDA, TMRM fluorescence never recovered (FIG. 18). Thus, although all stretched cells exhibited a drop in mitochondrial potential, only those that died (stretch+NMDA) exhibited an inability of mitochondrial potential to recover. Moreover, mitochondrial dysfunction in these cells started within minutes and thus preceded cell death.

Sublethal Stretch Produces High Levels of Non-lethal Reactive Oxygen Species.

Mitochondria are a significant source of neuronal reactive oxygen species (ROS) following anoxic or excitotoxic insults (reviewed in (Lipton, 1999; Nicholls and Budd, 2000)), and ROS mediate cell injury in neurotrauma (Lewen et al., 2000). As cell death in stretch+NMDA was associated with irrecoverable loss of mitochondrial function, I questioned whether this could be related to the ROS production in the cell.

Figure 19B:
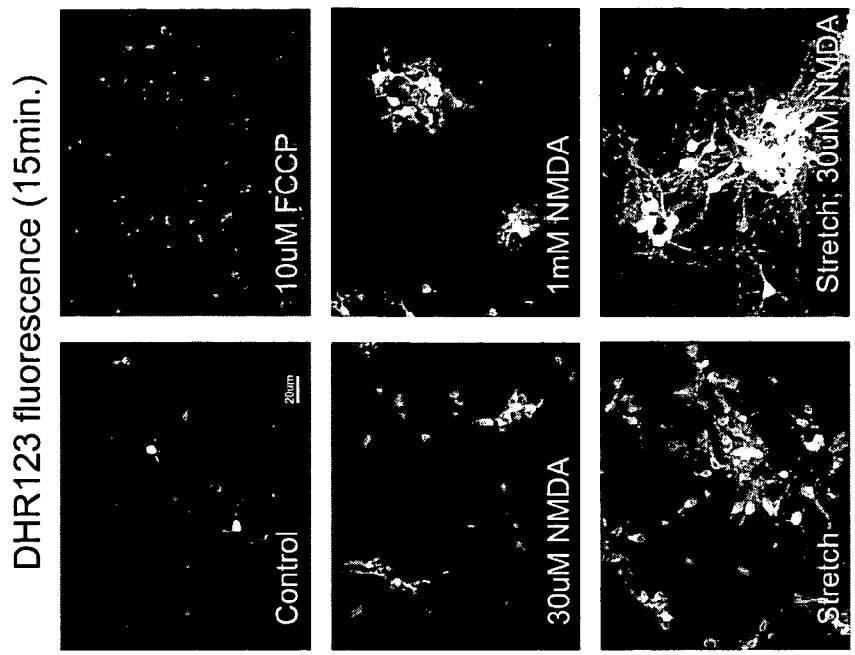
FIG. 19. Sublethal stretch injury causes extensive ROS production. Cultures were preincubated with DHR (5 μM) for 30 min prior to insult. DHR fluorescence was measured at 5 min intervals. Statistical comparisons were made at 60 min. A. Applying either 30 μM or 1 mM NMDA to unstretched cultures caused significant ROS production by 60 min as compared with controls (30 μM NMDA–$t_{32}$=5.82, p<0.0001; 1 mM NMDA–t35=7.57, p<0.0001). Stretch alone also caused extensive ROS production ($t_{34}$=15.13, p<0.0001), similar in magnitude to that of 1 mM NMDA ($t_{31}$=0.817, p=0.420). Applying 30 μM NMDA to stretched cultures further increased DHR fluorescence as compared with stretch alone ($t_{28}$=7.65, p<0.0001). Symbols represent the mean±SE of 14-20 cultures obtained from 3 separate dissections. Error bars are shown where they exceed symbol size. B. Representative DHR fluorescence images at 15 min after the indicated insult. Treating cultures with the mitochondrial uncoupler, FCCP, did not increase rhodamine-123 fluorescence at 15 min.

ROS levels were gauged over 60 min using the fluorescent indicator dihydrorhodamine-123 (DHR; (Royall and Ischiropoulos, 1993; Dugan et al., 1995)) as previously described (Tymianski et al., 1998). Treatment with the mitochondrial uncoupler FCCP abolished all DHR fluorescence (FIG. 19B, top right), thus excluding any possibility that an increase in DHR signal could be caused by stretch-induced mitochondrial depolarization.

Figure 19A:
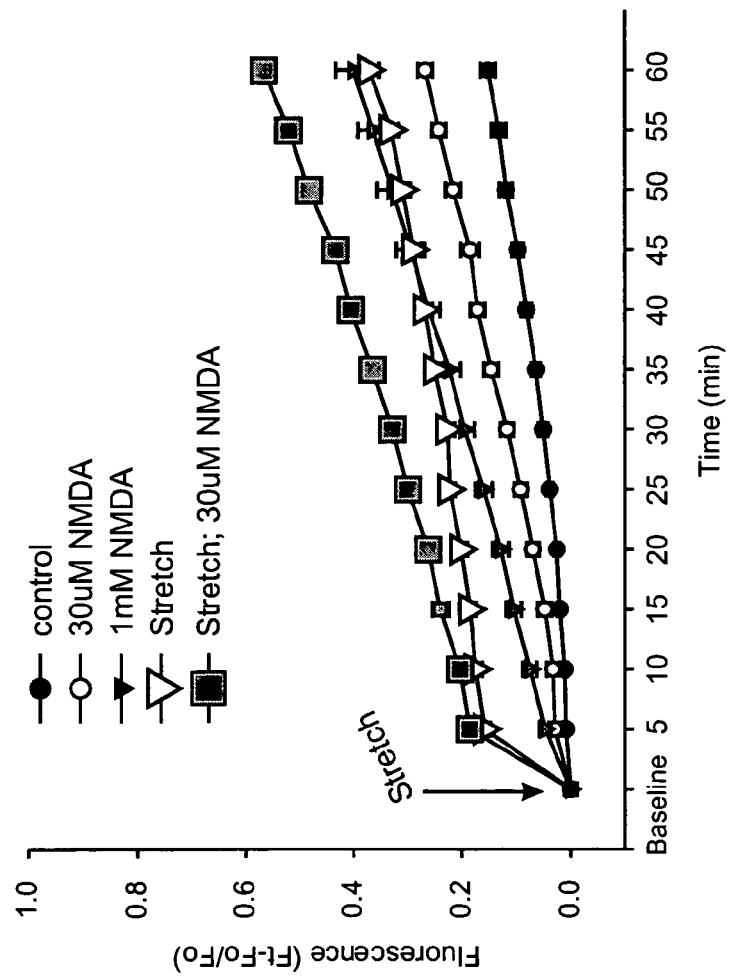

Treatment of unstretched cultures with 30 µM or 1 mM NMDA caused the expected progressive increase in ROS, with a larger rise produced by the 1 mM concentration of NMDA (FIG. 19A). Stretch+30 µCM NMDA produced the largest amount of DHR fluorescence, a finding commensurate with the lethality of this insult (FIG. 19A,B). Surprisingly however, lethality was not solely a function of the quantity of ROS produced: sublethal stretch alone produced a rapid increase in ROS production which matched that produced by a 1 mM NMDA insult (FIG. 19A). However, stretch alone was nonlethal, whereas all neurons challenged with 1 mM NMDA ultimately died (FIG. 14A). Thus, different insults can evoke similar levels of ROS, but similar levels of ROS do not necessarily dictate a similar lethality for different insults. This could be explained if ROS production was not the cause of NMDA toxicity, or if the stretch insult induced the production of different, less toxic, free radicals species than the NMDA treatment. Individual species of oxygen free radicals are difficult to resolve with fluorescent indicators. For example, DHR is sensitive to superoxide but also to other ROS such as hydrogen peroxide and peroxynitirite (Rothe et al., 1991; Royall and Ischiropoulos, 1993; Bueb et al., 1995; Gilad et al., 1997; Ostrovidov et al., 1998; Gow et al., 1999). Thus I turned to pharmacological approaches to further examine the contribution of ROS to the enhanced vulnerability of sublethally stretched neurons to NDMAR-mediated toxicity.

Pretreatment with a SOD Mimic Reduces Stretch-Induced ROS Production and NMDA Receptor-Mediated Toxicity.

ROS are produced in large quantities during excitotoxic or anoxic insults (Reynolds and Hastings, 1995; Bindokas et al., 1996; Lipton, 1999). To suppress their effects, I used the superoxide dismutase (SOD) mimetic MnTBAP which scavenges superoxide, hydrogen peroxide, and peroxynitrite (Patel et al., 1996; Day et al., 1997; Zingarelli et al., 1997; Hill et al., 2000).

Figure 20A:
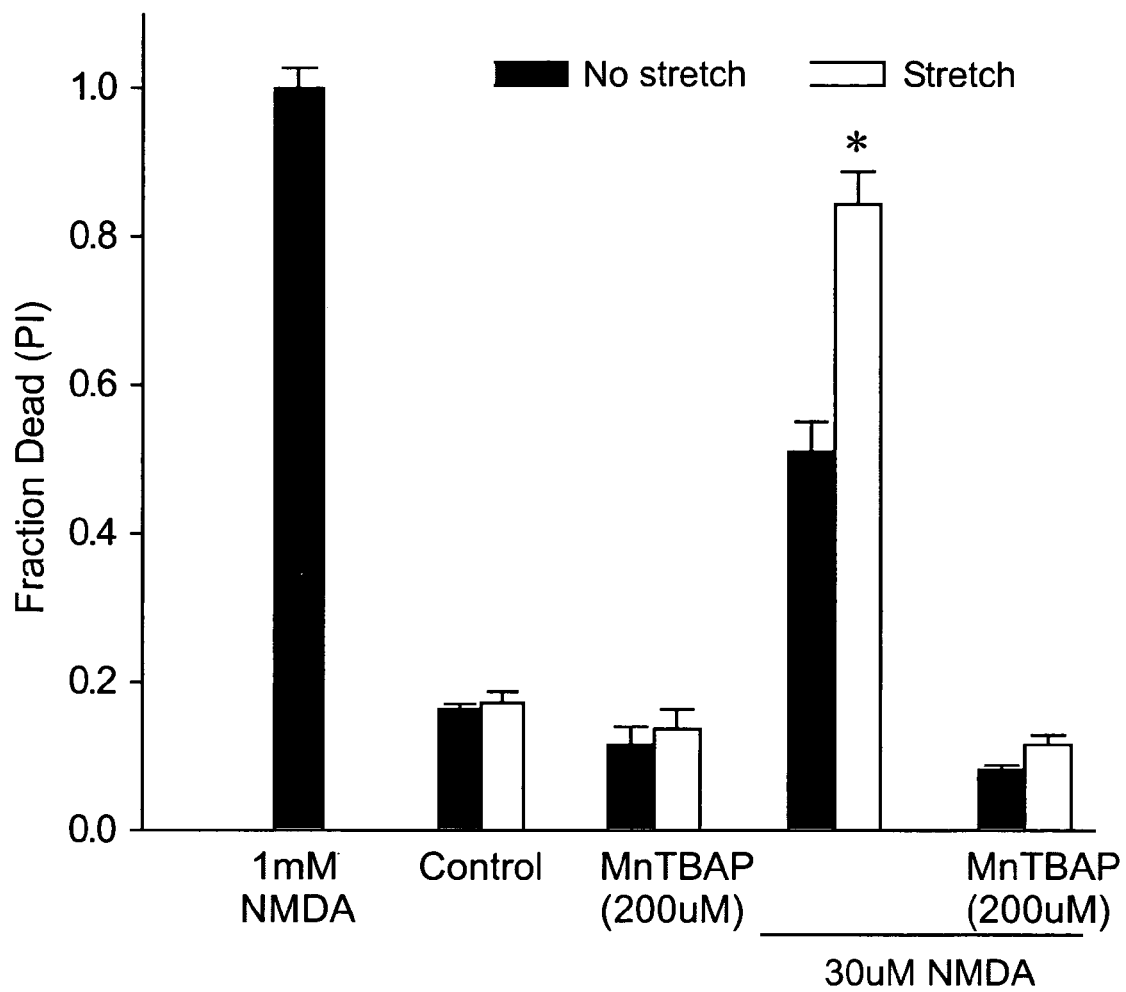
FIG. 20. Elimination of stretch-induced vulnerability NMDA toxicity by pretreatment with a ROS scavenger, MnTBAP. Cultures were preincubated for 30 min with 200 µM MnTBAP, which remained in the bath thereafter. Cell death was measured at 20 h. A. Effects of MnTBAP on cell death under the indicated conditions. Bars represent the mean+SE of 6-12 cultures obtained from 3 separate dissections. Asterisk: difference from unstretched cultures in same group ($t_{21}$=5.63, p<0.001). B. Representative phase contrast and propidium iodide fluorescence images of unstretched and stretched cultures 20 h after the indicated insult. C. Effect of MnTBAP on ROS levels in unstretched (top) and stretched (bottom) cultures. Pretreatment with MnTBAP reduced the 60 min DHR fluorescence in stretched and unstretched cultures under all insult conditions (Bonferroni t-test, p<0.05). Each symbol represents the mean±SE of 9-19 cultures obtained from 3 separate dissections.
Figure 20B:
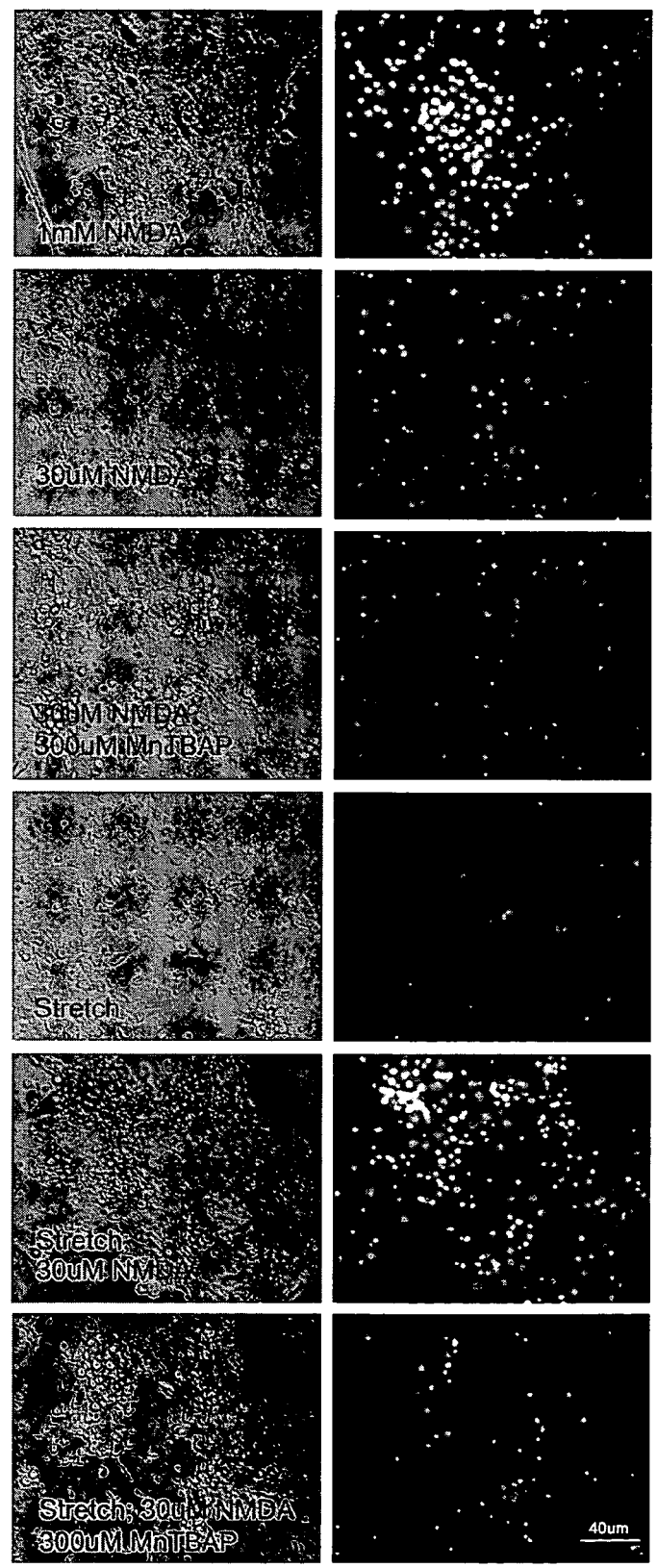

Accordingly, I first studied the effect of MnTBAP treatment on the survival of stretched neurons treated with NMDA. Cultures underwent stretch under the conditions indicated in FIG. 20A. Cell death was gauged at 20 h thereafter. Treatment with MnTBAP completely eliminated cell death in stretched cells treated with 30 µM NMDA (FIG. 20A,B). This confirmed that ROS are key in the vulnerability of the neurons to NMDA, and thus, in the vulnerability of stretched cells to NMDA.

To confirm that MnTBAP protected cells by reducing ROS production I repeated the stretch experiments with MnTBAP and subsequently measured ROS with DHR. MnTBAP pretreatment reduced DHR fluorescence in all culture conditions, indicative of reduced ROS production (FIG. 20C). These findings support the use of DHR as a ROS probe in these experiments and confirm the role of ROS in the toxic effects of NMDA in stretched cells.

Nitric Oxide is Required for the Enhanced Vulnerability of Sublethally Stretched Neurons to NMDA.

Figures 21A, 21B:
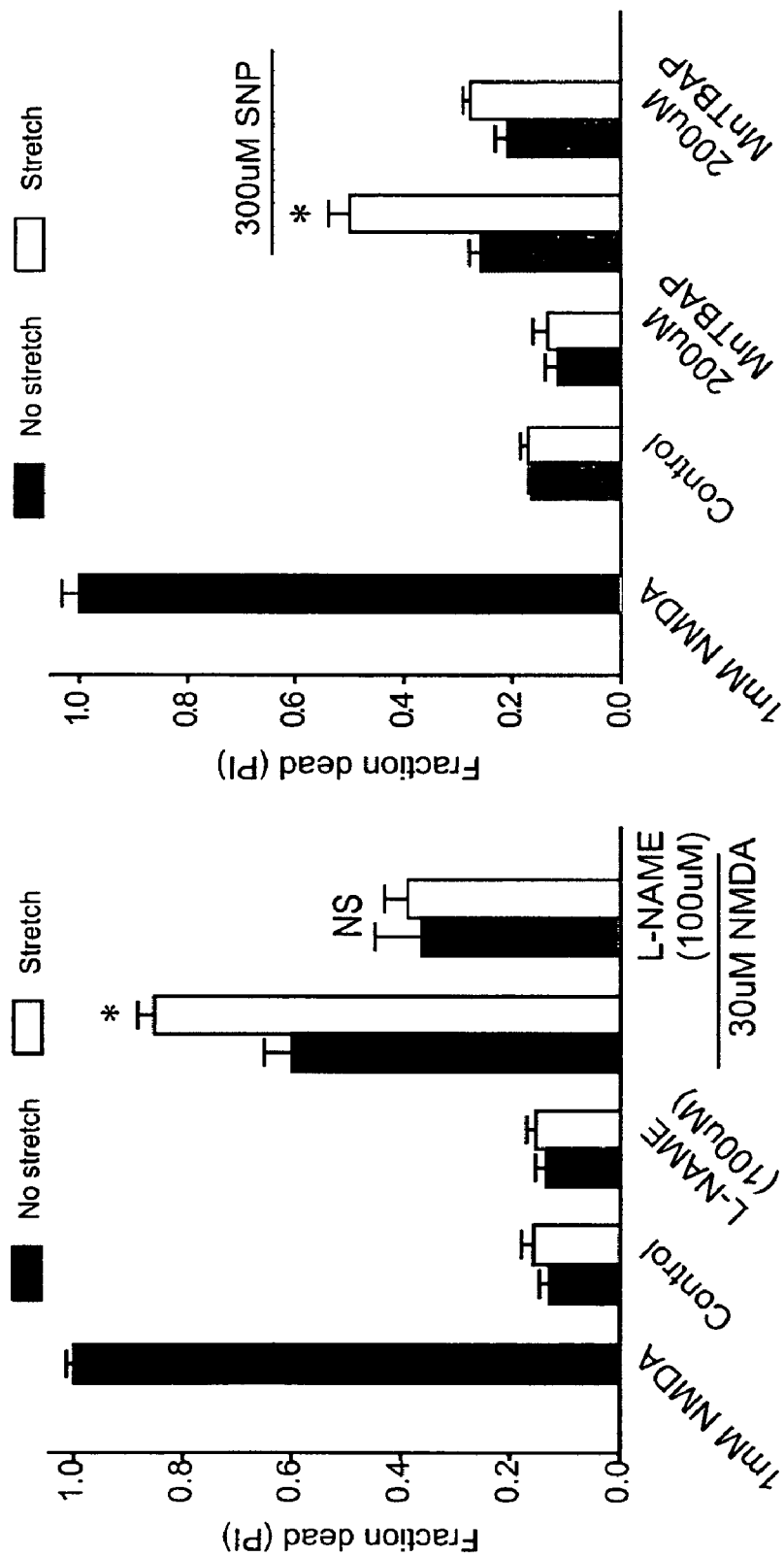
FIG. 21. Nitric oxide production is key in stretch-mediated vulnerability to NMDA toxicity. Cell death in A,B, was measured at 20 h. A. Effects of L-NAME, a NOS inhibitor, on cell death under the indicated conditions. Cultures were preincubated with 100 µM L-NAME for 30 min. Asterisk: Different from paired control ($t_{18}$=4.141, p<0.001). N.S.: not different from paired control ($t_{25}$=1.14, p=0.313). Bars represent the mean+SE of 6-19 cultures obtained from 3 separate dissections. B. Attenuation of sodium nitroprusside (SNP; 300 µM; an NO donor) toxicity by the ROS scavenger MnTBAP. The solutions contained MK-801 (10 µM), CNQX (10 µM) and nimodipine (2 µM) to block Ca influx through these pathways. SNP was applied for 1.5 hours. Prior stretch enhanced the vulnerability of neurons to SNP (Asterisk; $t_{16}$=5.583, p<0.001), and this was abolished with a 30 min pretreatment with 200 µM MnTBAP. Bars represent the mean+SE of 6-12 cultures obtained from 3 separate dissections. C. Effect of NMDA treatment on nitrotyrosine staining at the indicated time and conditions. D. Quantification of nitrotyrosine staining intensity at the indicated times. Background-subtracted fluorescence intensity measurements were taken from 5-15 randomly chosen fields from each culture using identical excitation wavelengths, microscope and camera settings. Bars: mean+SE of 2 cultures from each of 2 separate experiments. Asterisks: difference from unstretched controls at the same time-point (Bonferroni t-test, p<0.05).

The most common ROS produced by mithochondria is superoxide (Nicholls and Budd, 2000). However, in some instances NMDAR-mediated toxicity has been ascribed to nitric oxide (NO) (Dawson et al., 1991; Sattler et al., 1999), produced by nNOS. To determine the role of NO in the vulnerability of stretched neurons to NMDA, I first used the NOS inhibitor L-NAME, which protects these cultures against NMDAR toxicity (Sattler et al., 1999). Treating the cultures with L-NAME reduced the toxicity of 30 µM NMDA in unstretched neurons (FIG. 21A), though not to the extent achieved by the SOD mimic MnTBAP (compare with FIG. 21A). However, treatment with L-NAME completely eliminated the enhanced vulnerability of stretched neurons to NMDA (FIG. 21A). The disproportionate protective effect of L-NAME on the toxicity induced in stretched neurons by NMDA suggests that this enhanced vulnerability might be mediated by NO production.

To examine this further, I used the NO donor sodium nitroprusside (SNP) to generate this radical in stretched neurons (Sattler et al., 1999). Pilot experiments using the NO-sensitive dye 4,5, diaminofluorescine (DAF2-DA; (Kojima et al., 1998)) confirmed that SNP treatment enhanced NO levels in the cultures (not shown). If the enhanced vulnerability of stretched neurons to NMDA is mediated by NO, then stretched neurons should also be more vulnerable to the direct addition of the NO donor independently of NMDA. To test this, stretched and unstretched cultures were exposed to 300 µM SNP. Consistent with these hypothesis, stretched cultures exhibited increased vulnerability to SNP (FIG. 21B). Taken together, the selective effects of L-NAME and SNP on the vulnerability of stretched cultures strengthens the notion that NO production is important for this effect, and that NO is a mediator of the enhanced vulnerability of stretched cultures to secondary insults.

Nitric oxide reacts with mitochondrially-derived superoxide to form peroxynitrite (Bonfoco et al., 1995), a potent radical to which have been ascribed the damaging effects of NO signaling (Royall and Ischiropoulos, 1993; Trackey et al., 2001). Indeed, treating the cultures with MnTBAP, which scavenges superoxide and peroxynitrite (Zingarelli et al., 1997), reduced SNP toxicity to baseline (FIG. 21B) suggesting that this toxicity might involve peroxynitrite formation. Accordingly, I next examined the role of peroxynitrite in the vulnerability of stretched neurons to NMDA toxicity.

Peroxynitrite is the Lethal ROS Responsible for Enhanced NMDA Toxicity in Stretched Cultures.

Figure 21C:
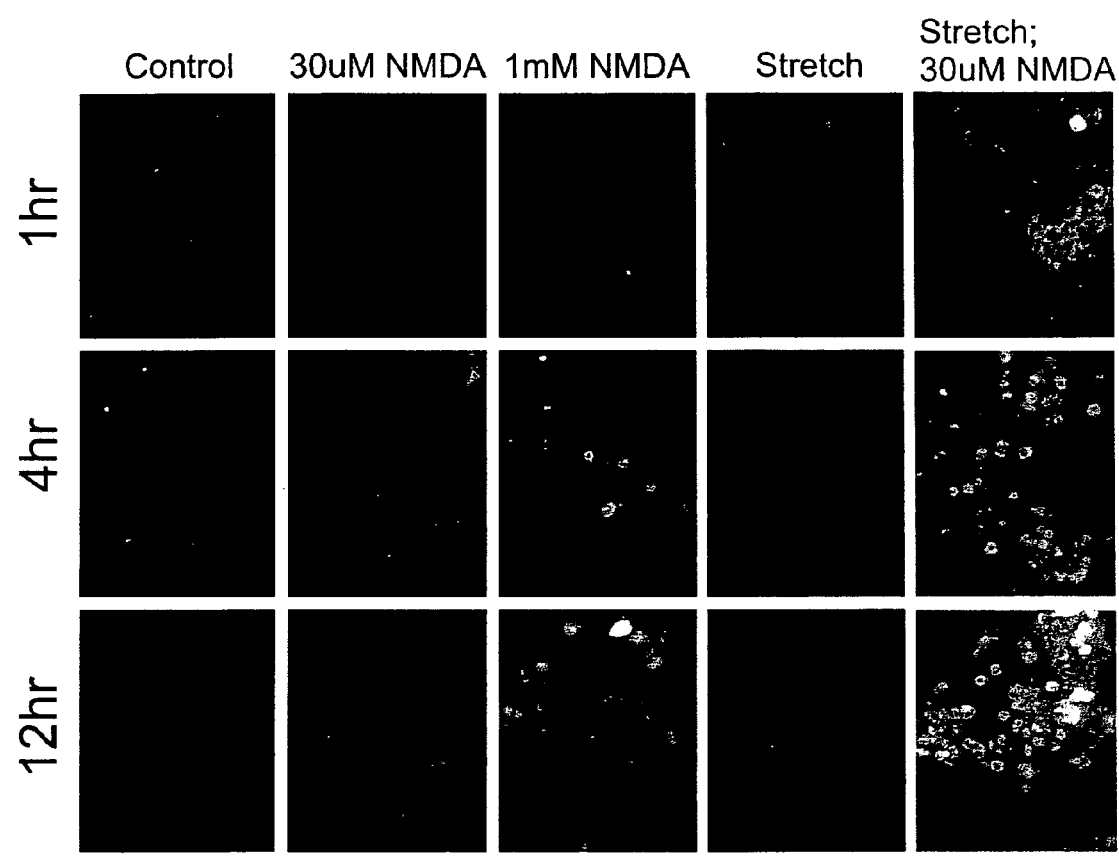
Figure 21D:
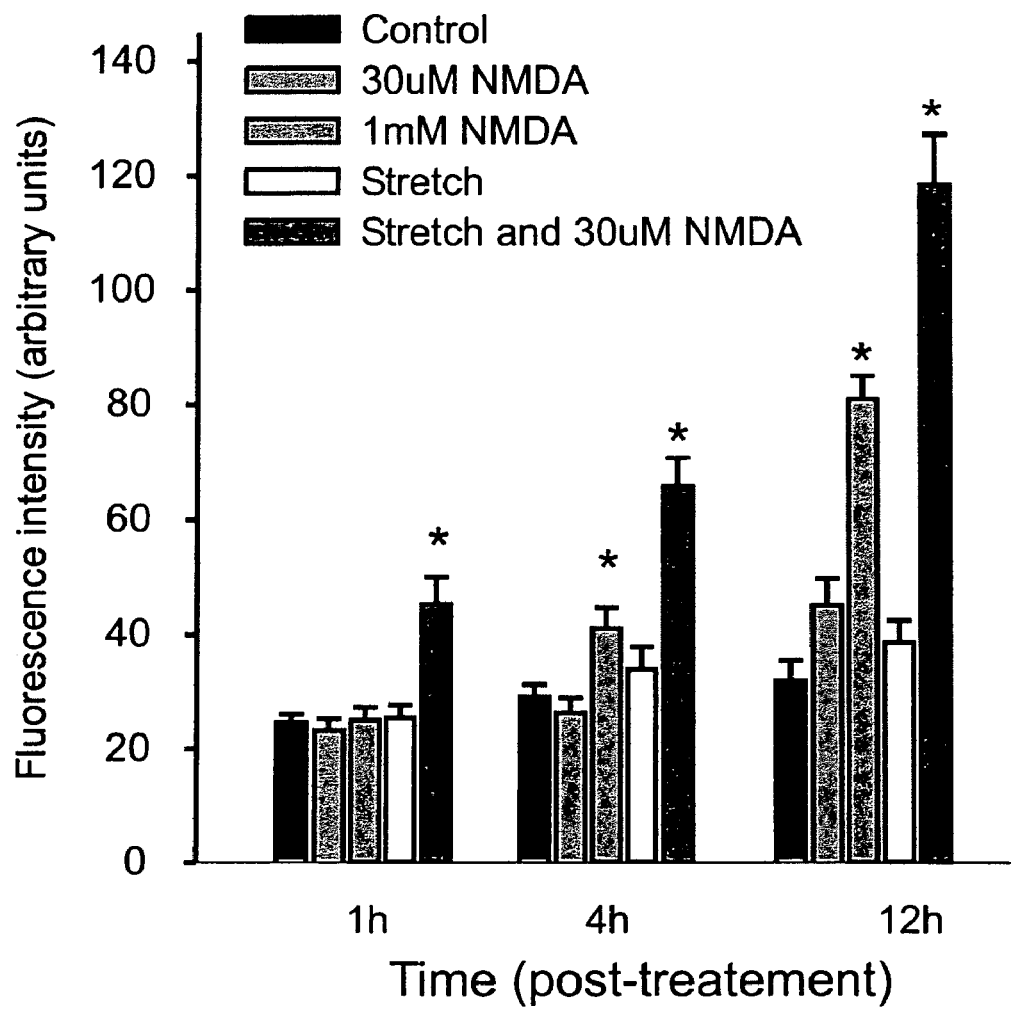

Peroxynitrite nitrates tyrosine residues found on many proteins and this can be detected immunohistochemically by anti-nitrotyrosine antibodies (Trackey et al., 2001). To determine whether peroxynitrite is the ROS mediating the vulnerability of stretched neurons to NMDA cultures were exposed to stretch, stretch+30 µM NMDA, or NMDA at low (30 µM) or high (1 mM) concentrations. Nitrotyrosine staining was carried out at 1 h, 4 h and 12 h after the indicated experimental manipulations (FIG. 21C,D). Unstretched cultures that had been challenged with 1 mM NMDA displayed significantly increased nitrotyrosine immunofluorescence as compared with unstretched cultures controls, cultures challenged with 30 µM NMDA, or with cultures challenged only with stretch. This indicates that stretch alone does not produce peroxynitrite, a finding consistent with the lack of cell death with stretch alone. Furthermore, the data indicate that an NMDA insult evokes the production of ROS that are different from those elicited by stretch. The results point to peroxynitrite as the likely culprit necessary for cell death in these paradigms and explain why stretch and 1 mM NMDA insults each evoke similar levels of ROS as measured with DHR (FIG. 19A) but the NMDA insult is lethal while the stretch is not. As suggested in a previous study (Trackey et al., 2001), cortical cells may be better able to cope with an oxidative but not a nitrosative stress.

An application of 30 µM NMDA to unstretched neurons, or exposure only to sublethal stretch, did not evoke significant nitrotyrosine staining. However, the lethal combination of the two caused an even greater amount of nitrotyrosine staining than the 1 mM NMDA insult (FIG. 21C,D). This suggests that the production of superoxide by prior stretch sensitizes the neurons so that the NO produced by low NMDA concentrations (30 µM) is channeled into peroxynitrite production.

Pretreatment with L-NAME or MnTBAP Protect Neurons from Internucleosomal DNA Fragmentation I have shown that DNA fragmentation occurs to a significant extent only in stretched neurons subsequently challenged with NMDA, as compared with stretch alone, or NMDA alone (FIG. 15A-C). However, this DNA fragmentation was not the result of apoptosis (FIGS. 16,17). Moreover, I showed that death of stretched neurons challenged with NMDA requires ROS that include NO and peroxynitrite, and that these radicals explained the enhanced vulnerability of the stretched cultures to NMDA. Previous studies have shown that these radicals, on their own, can also induce DNA fragmentation (Hill et al., 2000). If so, then this fragmentation should be reversible by NO and peroxynitrite inhibition.

Figure 22A:
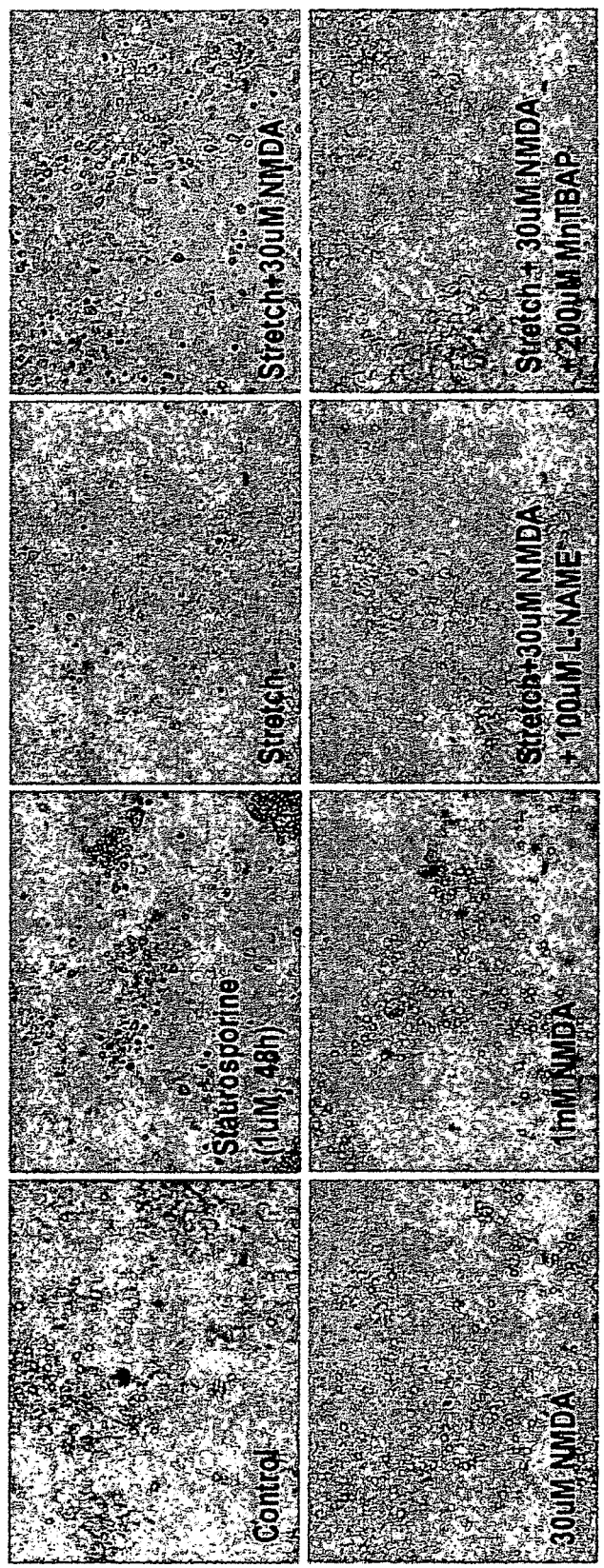
FIG. 22. Pretreatment with MnTBAP or L-NAME results reduces TUNEL staining and DNA laddering in sublethally stretched cultures challenged with NMDA. A. Representative images and B. Quantification, of TUNEL staining using the DAB method at 20 h after the indicated insult. The cultures were preincubated for 30 min with either 200 µM MnTBAP or 100 µM L-NAME as indicated. Staurosporine was applied for 48 h. Asterisks: difference from unstretched control, Bonferroni t-test, p<0.05. Each Plotted data represent TUNEL positive cells normalized to total cell number. Bars represent the mean+SE of 2-4 randomly selected fields in each of 3 cultures from each of 3 experiments. C. Representative DNA gel of the effect of pretreating stretched cultures with either MnTBAP or L-NAME on DNA laddering. Representative of 3 separate experiments.
Figures 22B, 22C:
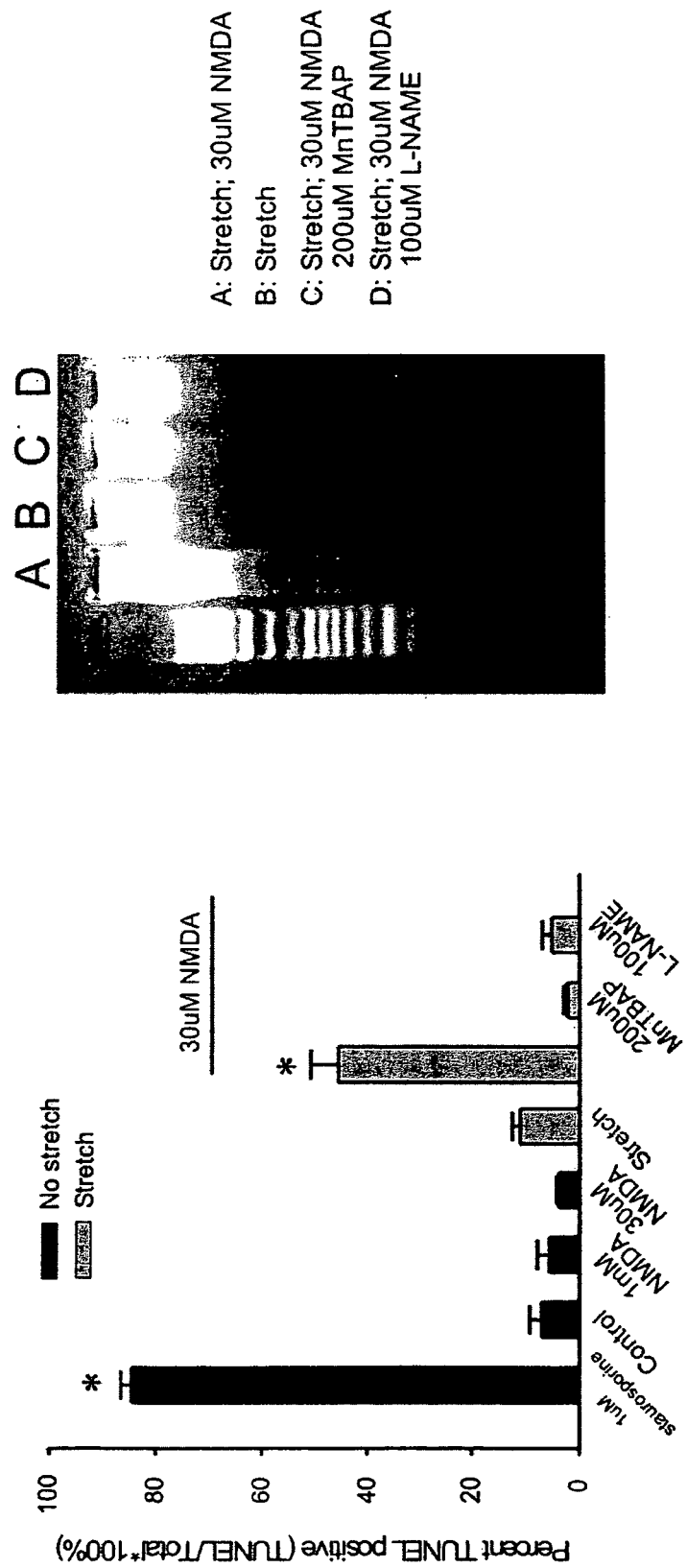

To test this, cultures were exposed to stretch followed by NMDA as before, but in the presence of MnTBAP or the NOS inhibitor L-NAME. TUNEL staining and DNA gel electrophoresis were performed as before at 20 h post-insult. Treatment with either compound virtually abolished TUNEL staining (FIG. 22A,B) and DNA laddering (FIG. 22C), confirming that DNA fragmentation was the result of ROS produced through the NO signaling pathway.

Disrupting NMDAR/PSD-95 Interactions Attenuates Stretch-Induced Enhancement of NMDA Toxicity.

If NO signaling is responsible for the enhanced vulnerability of stretched neurons to secondary insults through NMDARs, then this vulnerability should be blocked by disrupting NO signaling. Although NOS inhibition with L-NAME is one approach, it may not be specific to neurons. In some studies, inducible NOS in glia has been implicated in mediating excitotoxic and anoxic damage to cortical neurons in mixed cultures (Hewett et al., 1994; Hewett et al., 1996).

An alternative method of inhibiting NO signaling with greater specificity to neurons is to focus on the molecular interactions that underlie nNOS activation by NMDARs. I have previously reported that nNOS activity can be inhibited by perturbing the interactions of NMDARs with the submembrane scaffolding protein post-synaptic density-95 (PSD-95; (Sattler et al., 1999)). Through its second PDZ domain (PDZ2), PSD-95 binds NMDAR NR2 subunits as well as NNOS, thus keeping this signaling enzyme in a close functional association with NMDARs (Brenman et al., 1996; Kornau et al., 1995; Brenman and Bredt, 1997). If PSD-95 links NMDARs to downstream signaling pathways responsible for enhancing NMDA toxicity after stretch, then dissociating PSD-95 from NMDARs should reduce or abolish this enhancement.

Figure 23A:
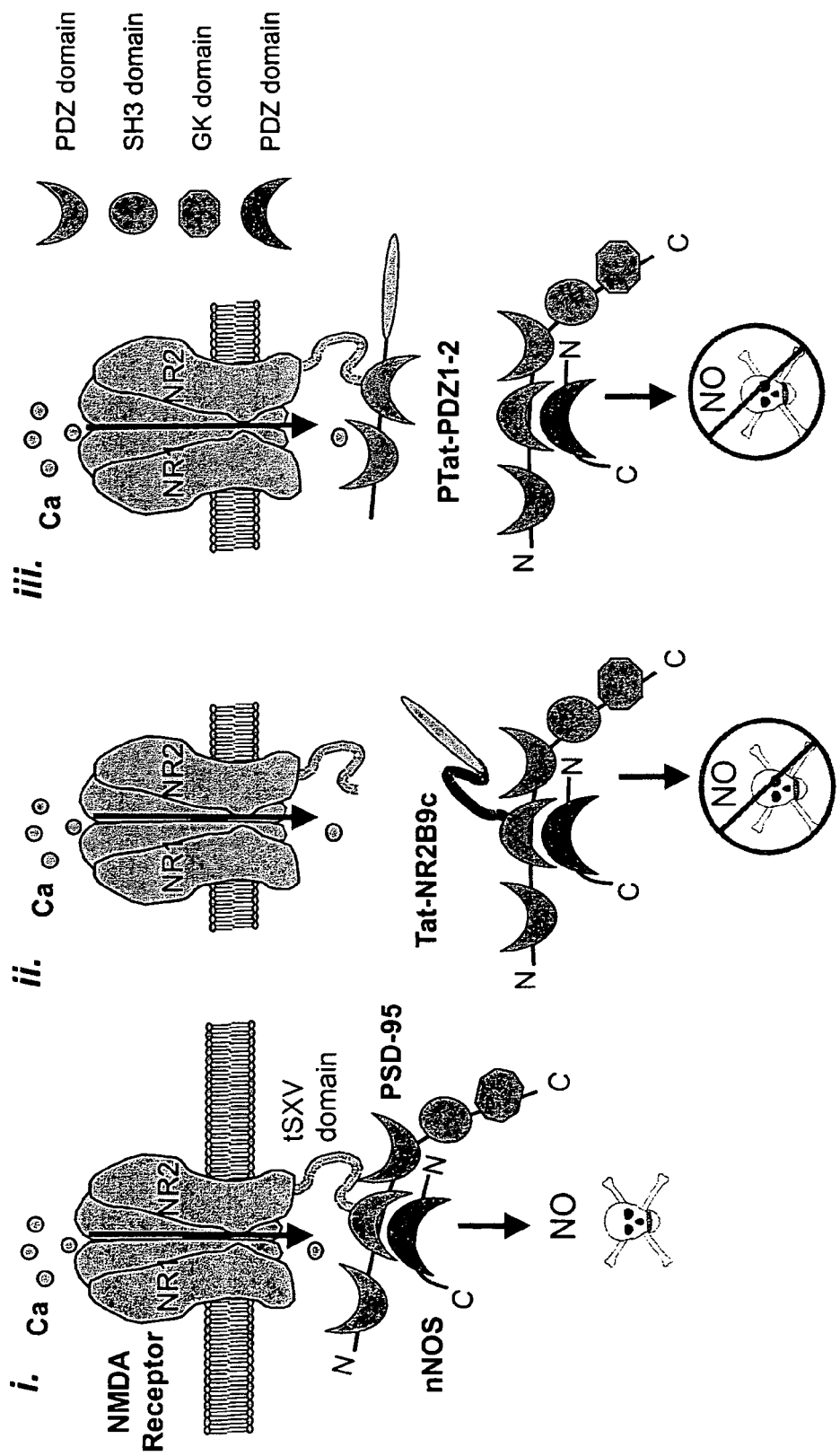
FIG. 23. Effect of uncoupling NMDAR NR2B from PSD-95 on ROS production and protein nitration. A. Schematic illustrating the approach: (i) NMDARs associate with NNOS via PSD-95 (ii, iii) Dissociating NNOS from NMDARs using Tat fused either to the C-terminus of NR2B (Tat-NR2B9c; ii) or to the first and second PDZ domains of PSD-95 (pTat-PDZ1-2; iii). B. Tat peptides and fusion proteins (pTat) used in these experiments. Inset: representative immunoblots obtained during purification of pTat-PDZ1-2 and pTat-GK proteins. C. Visualization of intraneuronal accumulation of Tat-NR2B9c-dansyl (10 µM) but not Tat-38-48-dansyl (10 µM) 30 min after application to cortical cultures. D. Effect on DHR fluorescence of pretreating cultures with Tat-NR2B9c 30 min prior to the indicated insult. Cultures were simultaneously preincubated with 110 M DHR for 30 min prior to the insult. Pretreatment with 50 nM TatNR2B9c reduced ROS production in all stretched (lower graph) and unstretched (upper graph) cultures treated with NMDA (30 µM or 1 mM; Boneferroni t-test, p<0.05). However, Tat-NR2B9c has no effect on ROS production by stretch alone ($t_{24}$=1.10, p=0.284). Symbols: means±SE of 5-18 cultures from 3 separate experiments. E. Tat-NR2B9c pretreatment reduces NMDA receptor-mediated protein nitration. Nitrotyrosine immunostaining was performed 12 h after the insult under the indicated conditions (representative of 3 experiments).

The interaction between NMDAR NR2B subunits and the PDZ2 domain of PSD-95 depends on a conserved C-terminus tSXV motif of NR2B (FIG. 23A$_i$; (Kornau et al., 1995)). This interaction can be disrupted by the intracellular introduction of exogenous proteins that competitively bind to either the NR2B or the PDZ2 interaction domains (FIG. 23A$_{ii, iii}$). I used a 9 residue peptide encompassing the PDZ-binding motif of NR2B (KLSSIESDV SEQ ID NO:1; NR2B9c), which binds the PSD-95 PDZ2 domain (FIG. 23A$_{ii}$). This peptide prevents the association of PSD-95 with NR2 subunits (Kornau et al., 1995) and with Kv1.4 channels (Brenman et al., 1998). NR2B9c also increases the binding activity of full-length recombinant PSD-95 protein to MAP1A (Brenman et al., 1998). Although the significance of this is unclear, and microtubules are unlikely to participate in increasing the vulnerability of stretched cultures to NMDA toxicity, I controlled for this additional effect of NR2B9c by developing an alternative means to interfere with the NMDAR/PSD-95 interaction. I constructed a protein comprised of residues 65-248 of PSD-95 encompassing the first and second PDZ domains (PDZ1-2), which contains the principal binding domain in PSD-95 for the C-terminus of NR2B. This protein should also affect NR2B/PSD-95 binding by interacting with native NR2B C-terminus motifs (FIG. 23A$_{iii}$).

Figure 23B:
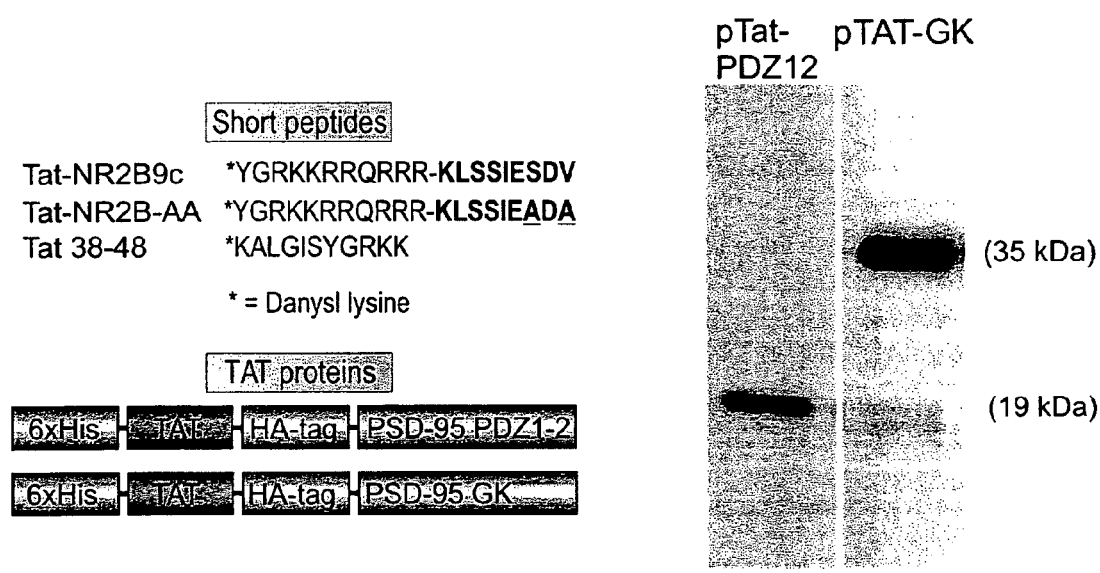

NR2B9c or PDZ1-2 on their own were not anticipated to enter cells and therefore, I fused each to a peptide corresponding to the cell-membrane transduction domain of the HIV-1-Tat protein (YGRKKRRQRRR SEQ ID NO:3; Tat) to obtain a 20 amino acid peptide (Tat-NR2B9c) and the fusion protein pTat-PDZ1-2 (FIG. 23B). These transduce cell membranes in a rapid, dose-dependent manner independent of receptors and transporters (Schwarze et al., 1999; Aarts et al., 2002). As a control for cell transduction I created a peptide comprised of HIV-1-Tat residues 38-48 (KALGISYGRKK SEQ ID NO:7; Tat38-48) outside the Tat transduction domain (Mann and Frankel, 1991), which does not pass through cell membranes (Aarts et al., 2002). As a control for the Tat-NR2B9c peptide I synthesized a peptide in which the C-terminal tSXV motif of NR2B contained a double point mutation to alanines (Tat-KLSSIEADA SEQ ID NO:12; Tat-NR2BAA) rendering it incapable of binding PSD-95 (Kornau et al., 1995). As a control for pTat-PDZ1-2 I made pTat-GK, a Tat fusion protein containing residues 534-724 of PSD-95 comprising the C-terminal guanylate-kinase homology domain that lacks enzymatic activity (Kistner et al., 1995). A listing of the active and control proteins constructed to target either side of the NR2B/PSD-95 interaction is provided in FIG. 23B.

To examine intracellular delivery of Tat peptides, they were conjugated to the fluorophore dansyl chloride (excitation: 360 nm, emission: >51 µm). Intracellular accumulation of dansyl-Tat-NR2B9c (10 µM) but not control peptide (dansyl-Tat-38-48; 10 µM) was observed 30 min after application to cortical neuronal cultures using confocal microscopy (FIG. 23C, representative of 5 experiments). Fluorescence of cultures treated with dansyl-Tat-38-48 was similar to background (not shown). In a previous study, dansyl-Tat-NR2B9c was detectable in the neurons within 10 min of the start of the application, reaching a peak level over the next 20 min. This level was maintained until the dansyl-Tat-NR2B9c was washed from the bath and the peptide remained detectable within the neurons for more than 5 hours thereafter (Aarts et al., 2002). In previously characterizing the effects of Tat-NR2B9c in-vitro, I found that applying Tat-NR2B9c reduced the co-immunoprecipitation of PSD-95 with NR2B. In hippocampal CA1 neurons Tat-NR2B9c (50 nM) had no effect on synaptic responses, on patch recordings of total excitatory post-synaptic currents (EPSC) nor on AMPA or NMDA components of the EPSC. In cultured cortical neurons, Tat-NR2B9c or pTat-PDZ1-2 (each at 50 nM) did not alter the uptake of $^{45}Ca^{2+}$ produced by applying NMDA (Aarts et al., 2002). However, Tat-NR2B9c (50 nM) treatment dissociated NMDA receptor activity from nitric oxide production by neuronal nitric oxide synthase (Aarts et al., 2002), which is bound to the PDZ2 domain of PSD-95 (Brenman et al., 1996).

Figure 23D:
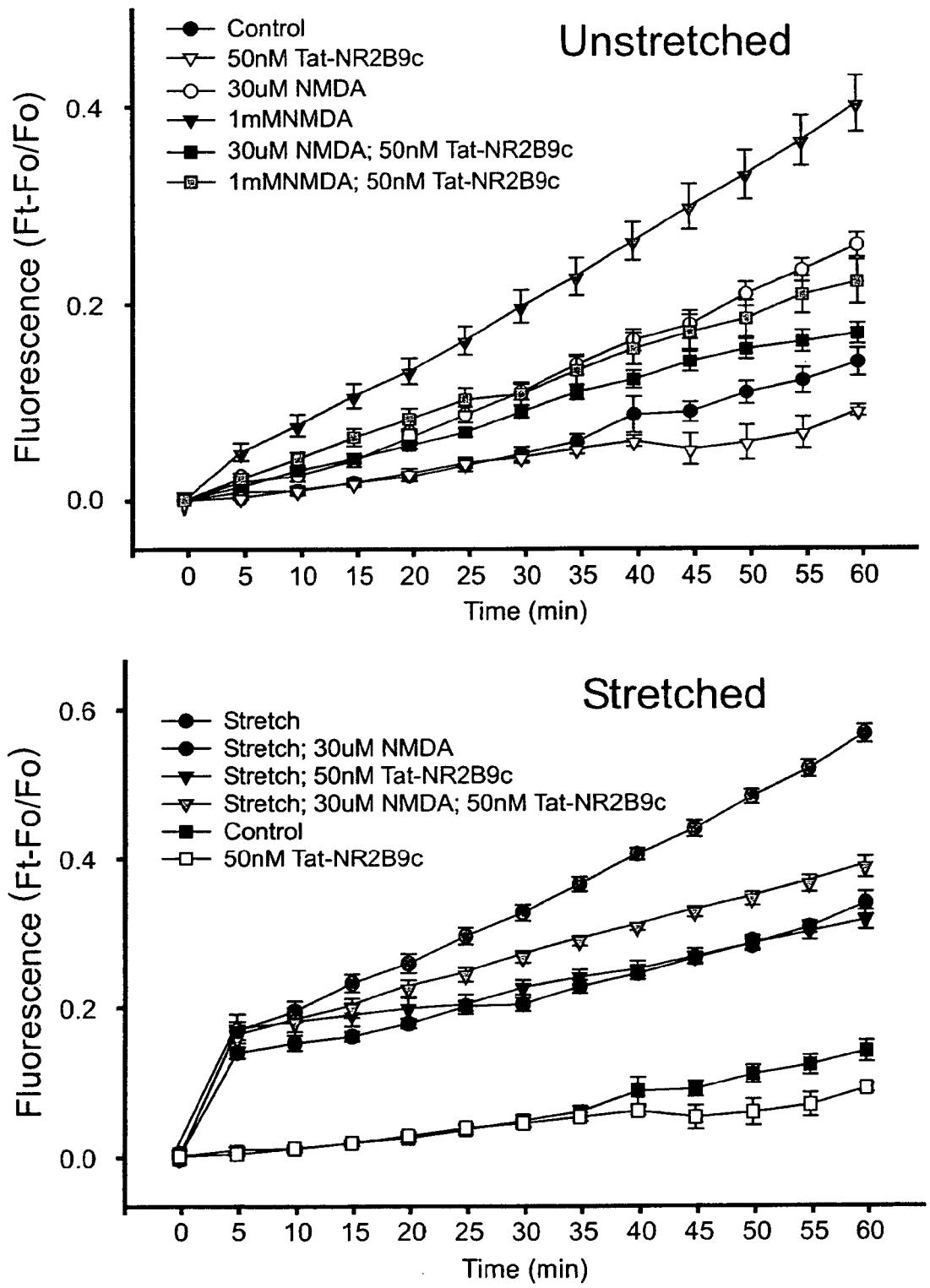
Figure 23E:
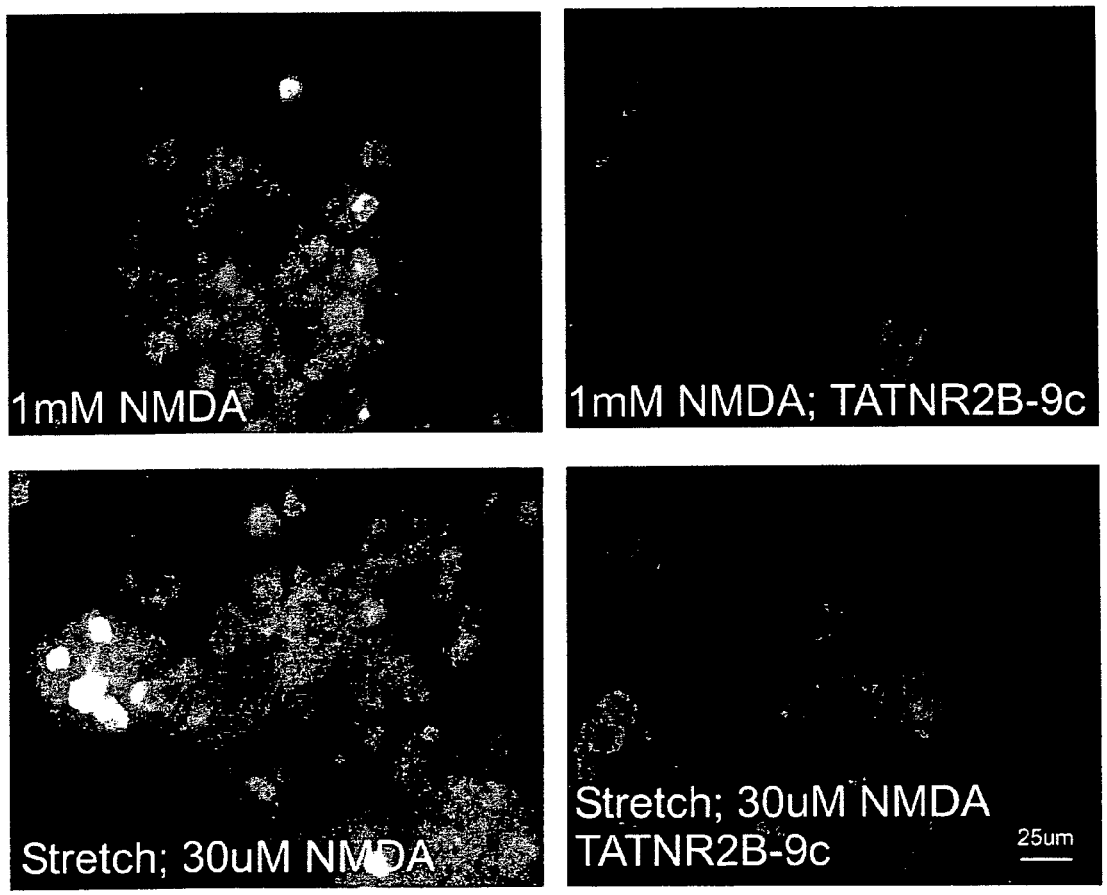

Having previously shown that Tat-NR2B9c treatment reduced NO production in cultures challenged with NMDA (Aarts et al., 2002), I next evaluated the effects of Tat-NR2B9c on NMDA-mediated free radical production and nitrotyrosine staining in both unstretched (FIG. 23D, top) and stretched cultures (FIG. 23D bottom). Tat-NR2B9c pretreatment reduced NMDA-evoked ROS production in both paradigms, as measured by DHR oxidation (FIG. 23D). Also, Tat-NR2B9c pretreatment resulted in reduced nitrotyrosine immunoreactivity at 12 h post-NMDA challenge-indicating that this approach successfully reduces peroxynitrite formation in the neurons (FIG. 23E).

Figures 24A, 24B:
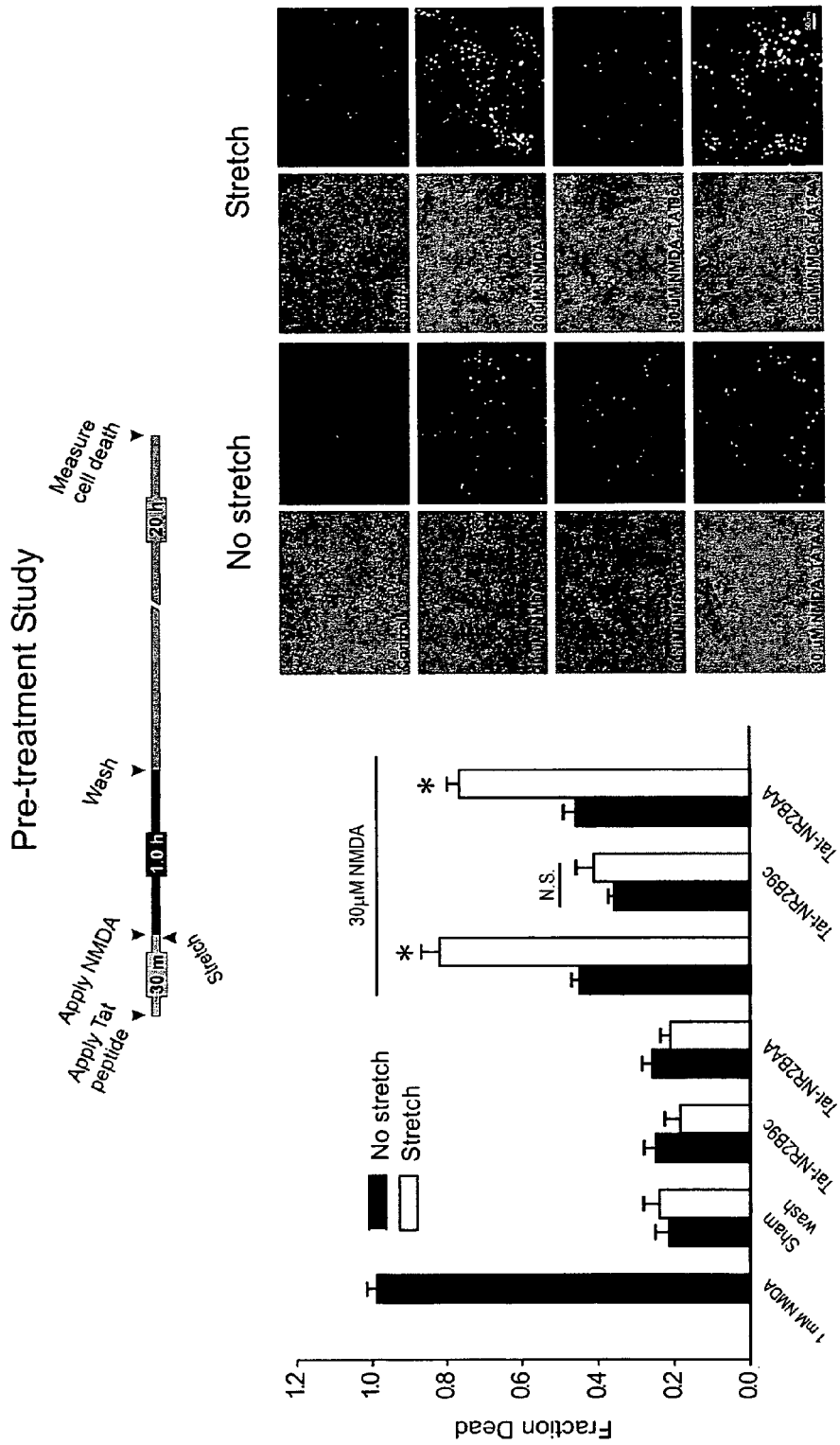
FIG. 24. Pretreatment and post-treatment with Tat peptides and fusion proteins reduces the stretch-induced increased vulnerability to NMDA toxicity. A. Effect of pretreatment with Tat peptides on survival 20 h after the indicated insults. Cultures were preincubated with 50 nM Tat peptides for 30 min. The peptides remained in the bath thereafter. Inset: experimental time-course. Asterisks: different from paired control, Bonferroni t-test, p<0.05. N.S.: not significantly different. Bars: mean+SE of 6-20 cultures obtained from 4 different experiments. B. Representative phase contrast and propidium iodide fluorescence images of unstretched (left) and stretched (right) cultures 20 h after challenge with 30 µM NMDA. Pretreatment with Tat-NR2B9c, but not with Tat-NR2B-AA, resulted in decreased propidium iodide fluorescence. C,D. Effect of post-treatment with Tat peptides (C) or fusion proteins (D) on cell survival 20 h after the indicated insult. The peptides or fusion proteins were added 1 h after insult onset (after termination of the NMDA challenge. Post-treatment with 50 nM Tat-NR2B9c or pTat-PDZ1-2 reduced the vulnerability of neurons to NMDA after stretch. Asterisks: differences from paired controls. Bonferroni t-test, p<0.05. Bars are mean+SE of 7-22 cultures obtained from 4 different experiments. Inset: experimental time-course.

Next, I examined the effect of pre-treating the cortical neuronal cultures with 50 nM Tat-NR2B9c or with the control peptide Tat-NR2BAA. The peptides were applied 30 min prior to stretch, and NMDA (30 µM) was applied for 1 h thereafter. Neuronal cell death was quantified 20 h after stretch (FIG. 24A,B top). The peptides had no toxic effects in control or in stretched cultures (FIG. 24A). Upon exposure to low NMDA concentrations, stretched cultures that were untreated with the peptides exhibited the anticipated increased vulnerability to NMDA toxicity (FIG. 24A). However, this heightened vulnerability was completely abolished in cultures pre-treated with Tat-NR2B9c (FIG. 24A). The effects of Tat-NR2B9c were not seen with the control peptide Tat-NR2BAA (FIG. 24A).

Figures 24C, 24D:
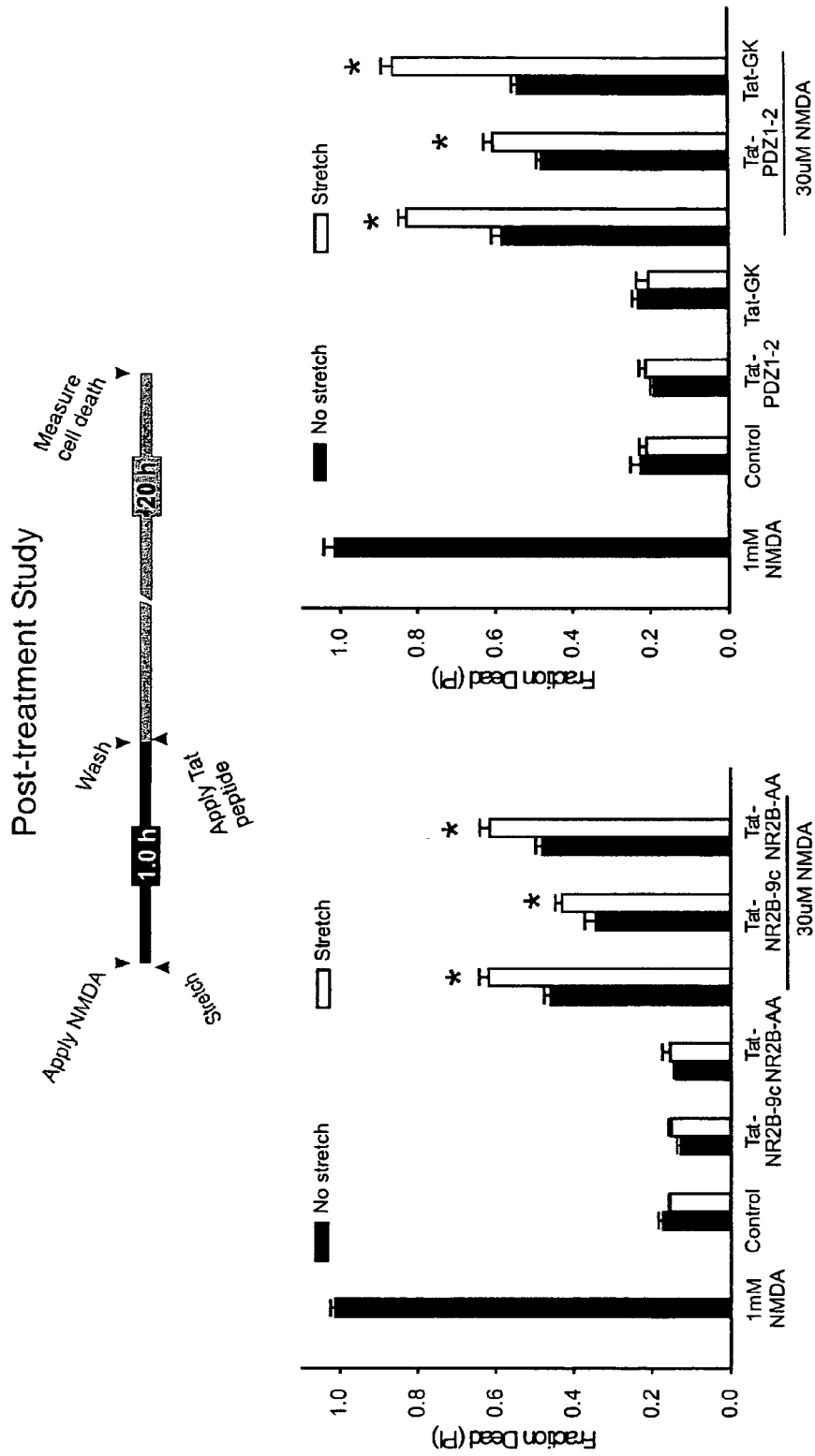
Figure 25:
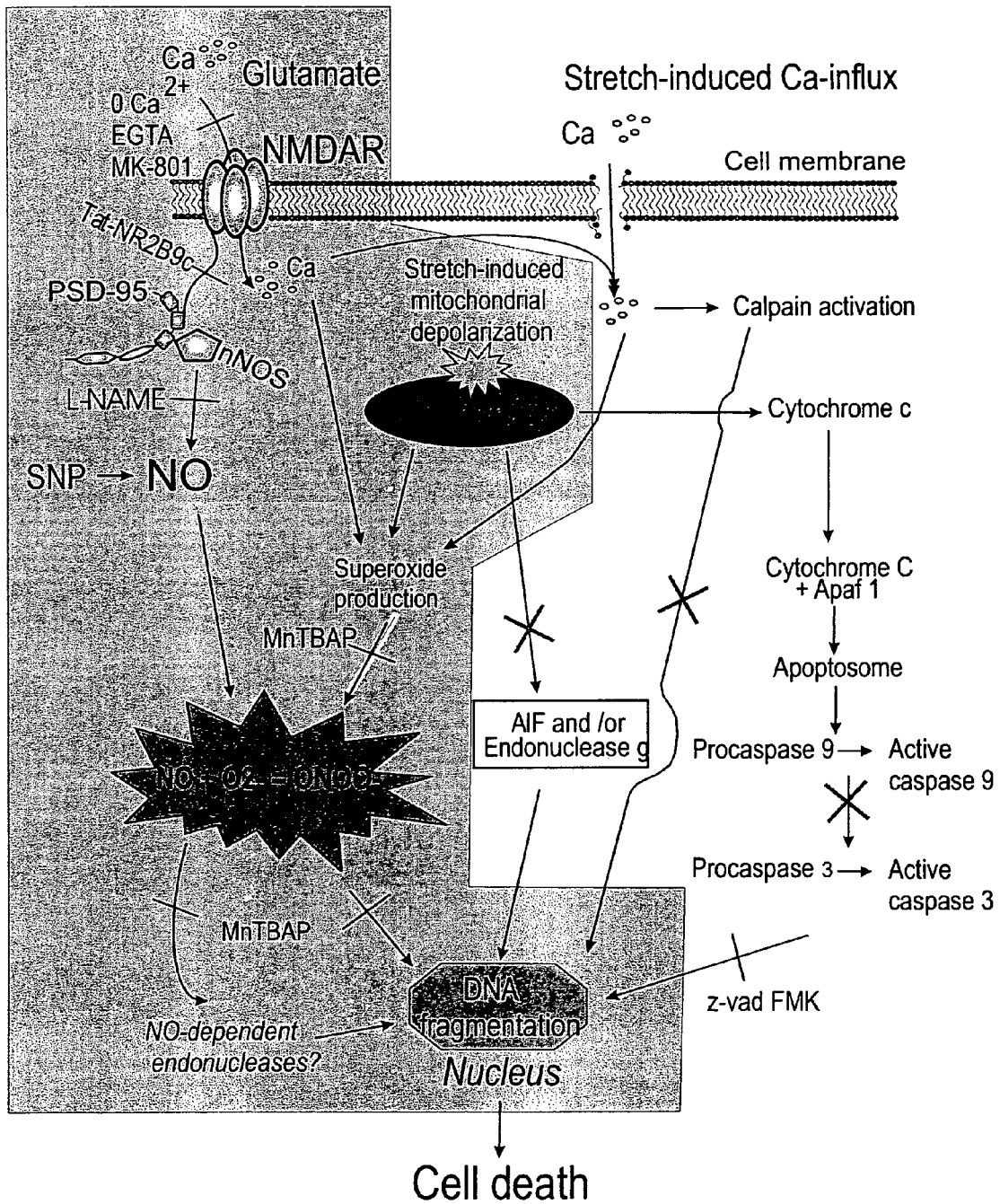
FIG. 25. Proposed mechanism of cell death in sublethally stretched neurons exposed to NMDA. Stretch results in increased superoxide production at a level that is still tolerated by the cells. However, subsequent NMDAR activation causes NO production, which permits the formation of peroxynitrite. This, in-turn, causes DNA fragmentation by a process independent of classical caspase dependent apoptosis, caspase independent apoptosis (AIF, endonuclease g) or caplains.

These data indicate that NMDARs, through their specific interactions with PSD-95 protein, are able to trigger distinct downstream signalling cascades responsible for the enhanced vulnerability of neurons to NMDA toxicity. As these signalling mechanisms, once activated, may persist beyond the duration of the NMDA challenge, I next examined whether post-treatment of cultures with Tat peptides or fusion proteins could also be protective. Experiments in cultured cortical neurons were repeated as in FIG. 24A, but the Tat-peptides were applied after terminating the 1 h NMDA challenge (FIG. 24C,D top). Post-treatment with Tat-NR2B9c, but not Tat-NR2B-AA, reduced the enhanced cell mortality produced in stretched neurons by the NMDA challenge (FIG. 24C). Similar results were obtained by post-treating the cultures with pTat-PDZ1-2, the fusion protein that targets the opposite side of the NR2/PSD-95 interaction from Tat-NR2B9c (FIG. 24D). By contrast, the control fusion protein pTat-GK, which does not target this interaction, was ineffective (FIG. 24D). In conclusion, introducing into the cells an exogenous peptide containing the C-terminal nine amino acids of the NR2B NMDAR subunit has profound effects on excitotoxic signalling pathways downstream of NMDAR activation. The effects of this peptide are lost by mutating amino acids that are essential for mediating PDZ binding to PSD-95. In addition, a protein comprising PDZ1-2 of PSD-95 shares the effects of the NR2B C-terminal peptide. These findings imply that the cytotoxic signals downstream from NMDARs may be interrupted by these cell-permeant peptides.

Figure 26:
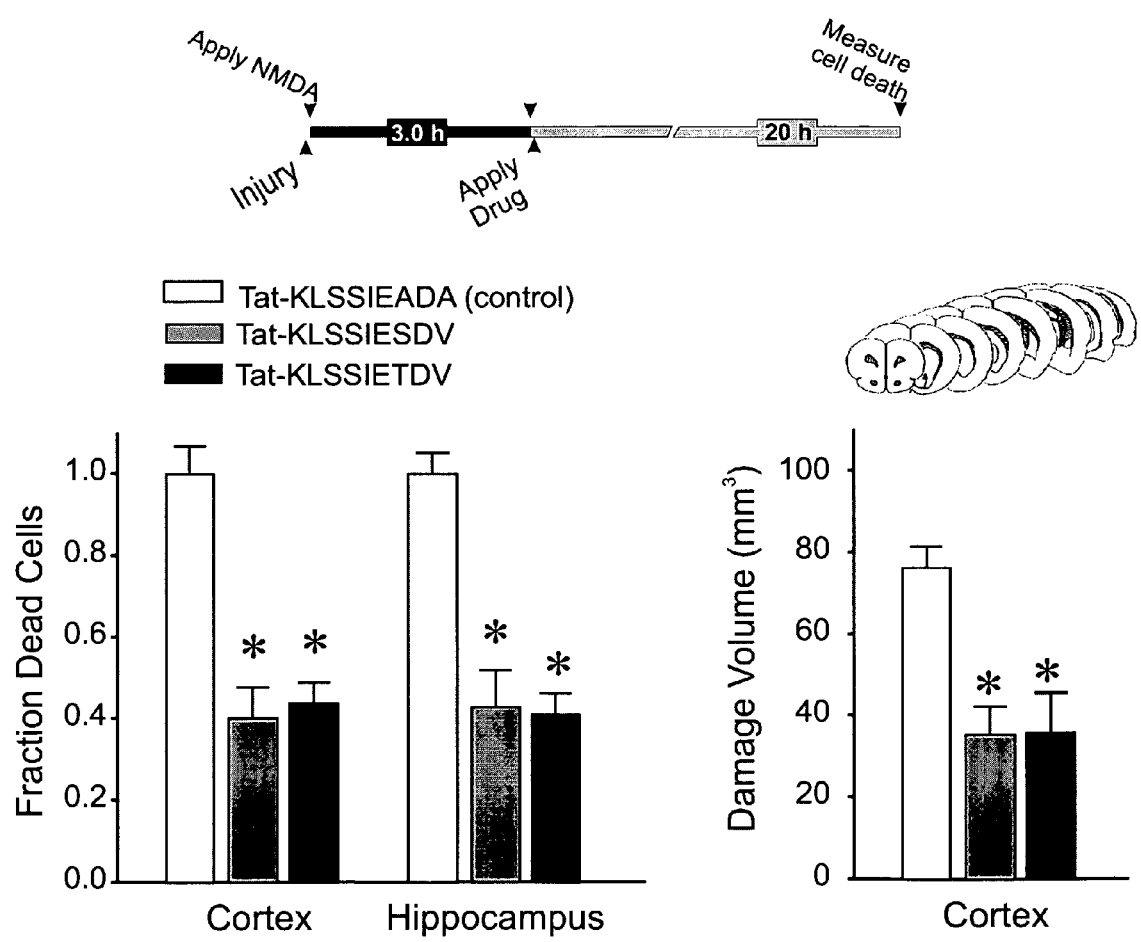
FIG. 26. Cell counts (normalized to control; left graph) and damage volume (right graph) analyzed 24 h after injury showing the effects of treating animals (3-4 per group) with the indicated peptide 3 hours after the injury. Inserts indicate the experimental protocol and the method of calculating damage volumes from representative coronal sections.
Figure 27A:
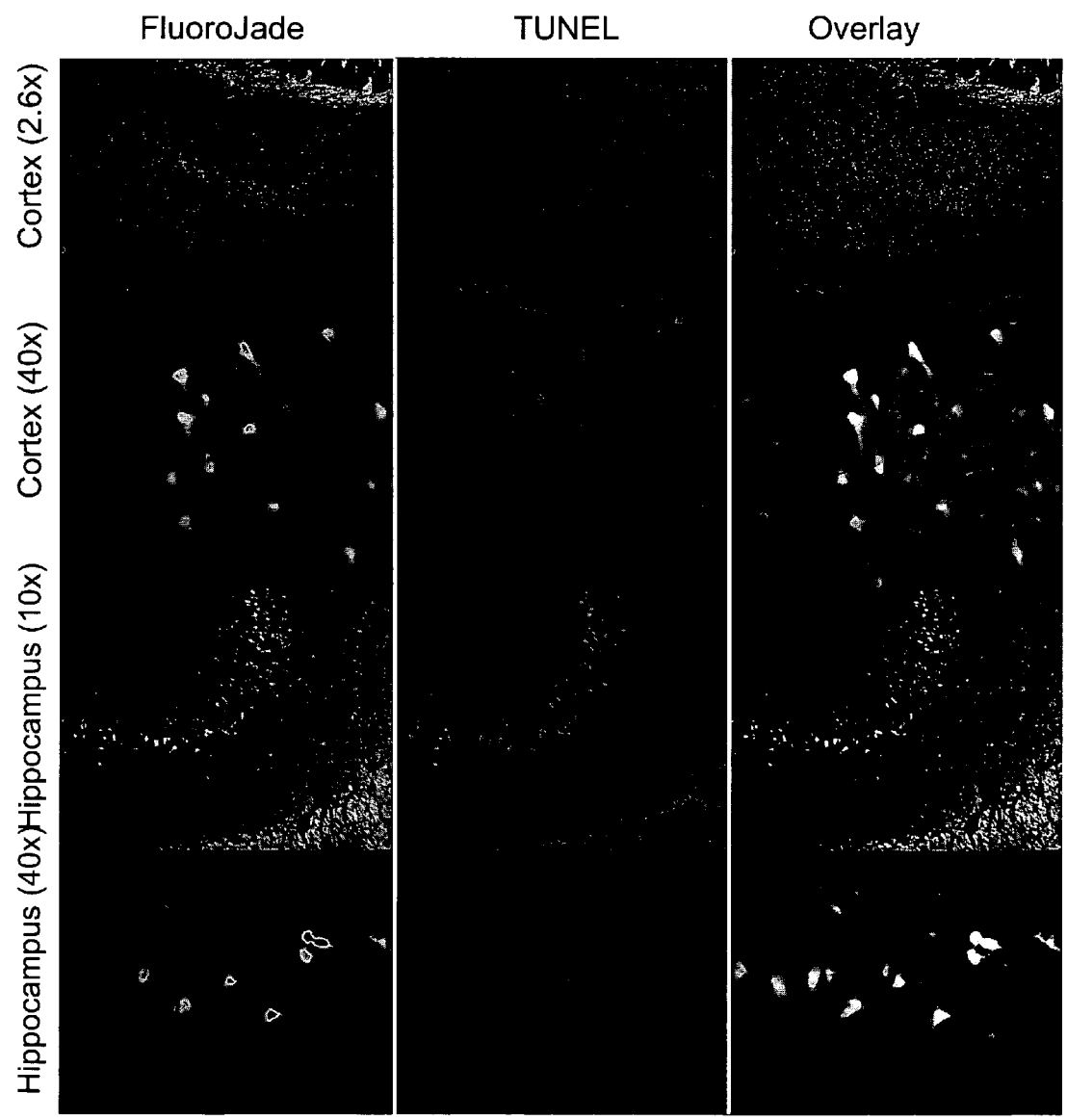
FIG. 27. Photomicrographs of representative areas, at the indicated lens power, from the cortex and the hippocampus of animals treated with Tat-KLSSIEADA (left set) or Tat-KLSSIESDV (right set).
Figure 27B:
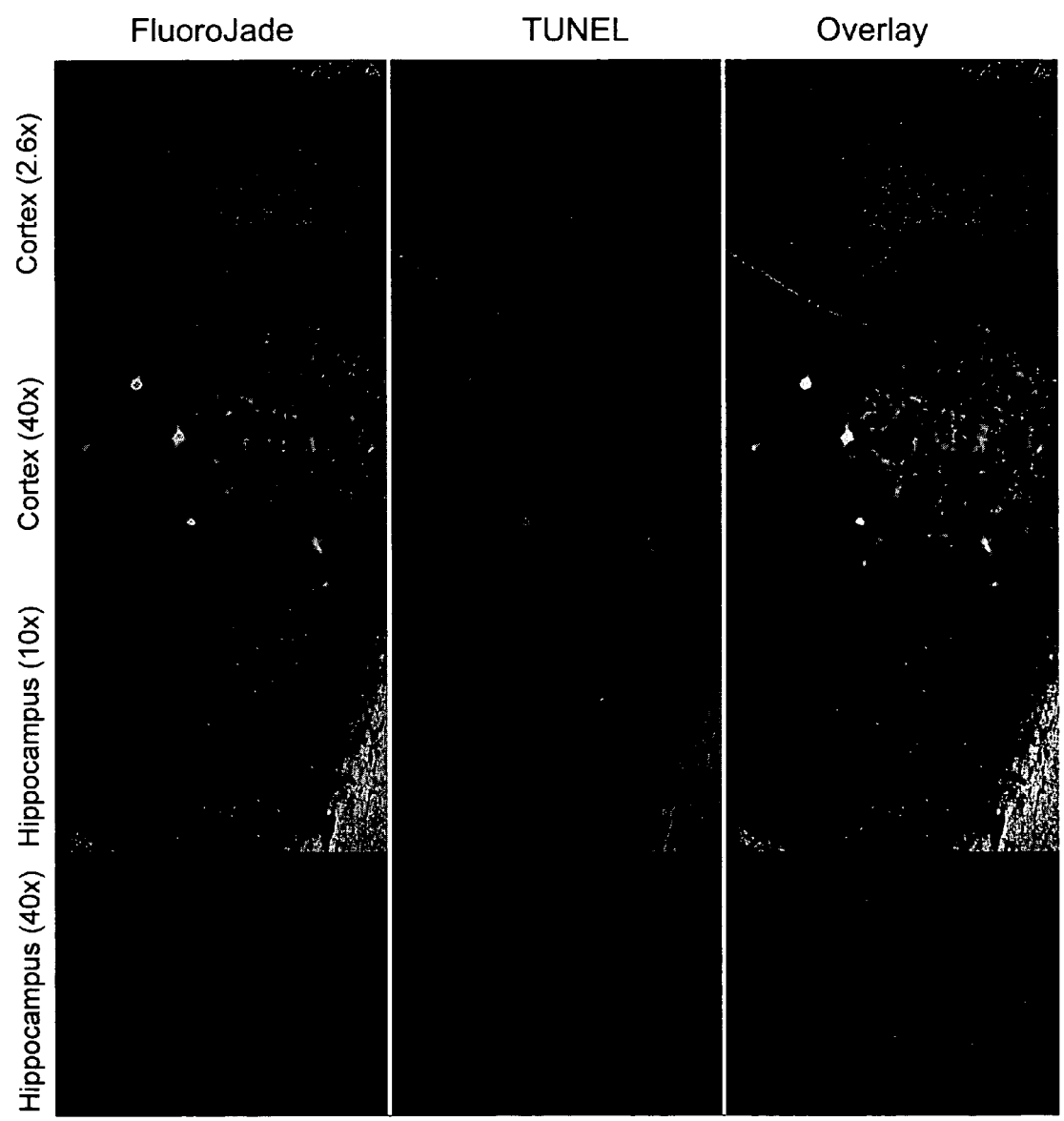

I next determined whether the effects of the Tat conjugated peptides reduced the effects of traumatic brain injury (TBI) in-vivo. I used the lateral fluid percussion injury model of TBI as described by McIntosh et al., 1989. Three peptides were tested: Tat-KLSSIESDV SEQ ID NO:4, Tat-KLSSIETDV SEQ ID NO:5 and the inactive control Tat-KLSSIEADA SEQ ID NO:12. Each were administered to the animal at 3 hours after the induction of the TBI. FIG. 26 shows that treatment of the animals resulted in a markedly reduced fraction of dead cells in the cerebral cortex and in the hippocampus ipsilateral to the injury site (FIG. 26, left panel, FIG. 27). Also, the total volume of injured brain was significantly reduced (FIG. 26, right panel). These data indicate that treatment of TBI with tSXV motif-containing peptides constitute a practical means to reduce the damaging effects of TBI.

Materials and Methods

Tissue Culture

Cortical neuronal cultures: Mixed cortical cell cultures containing both neurons and glia were prepared from embryonic Swiss mice at 15 days of gestation as previously described (Sattler et al., 1997), with minor modifications from Choi (1987). In brief, cerebral cortices from 10 to 12 embryos were incubated for 10 min in 0.05% trypsin-EDTA, dissociated by trituration, and plated on flexible membranes coated with poly-L-ornithine in 6 well plates (Flexcell International Corporation, Hillsborough, N.C.) at a density of $3.25 \times 10^6$ cells per well. Plating medium consisted of DMEM supplemented with 10% heat-inactivated horse serum (Gibco) and (in mM) 2 glutamine, 25 glucose, and 26 bicarbonate. The cultures were maintained at 37° C. in a humidified 5% $CO_2$ atmosphere. After 3 days in vitro, growth of non-neuronal cells was halted by a 48 h exposure to 10 µM FDU-solution (5 µM uridine, 5 µM (+)-5-fluor-2'-deoxyuridine). This produces cultures in which >85% of the cells are neurons, based on immunohistochemical staining for glial fibrillary associated protein (exclusive to astrocytes), and for the NMDAR1 subunit (not shown). The cultures were used for experiments after 12-14 days in vitro.

Drugs and Solutions

The control solution contained (in mM): 121 NaCl, 5 KCl, 20 D-glucose, 10 HEPES acid, 7 HEPES-Na salt, 3 $NaHCO_3$, 1 Na-pyruvate, 1.8 $CaCl_2$, and 0.01 glycine, adjusted to pH 7.4 with NaOH. All drug stock solutions were kept at −20 C. Stocks of the following were prepared in DMSO (10-20 mM) and diluted to their indicated final concentrations in control buffer: nimodipine (L-type $Ca^{2+}$ channel antagonist; Miles, Elkhart, Ind.; 2 µM), 6-cyano-7-nitroquinoxaline (CNQX; AMPA/kainate antagonist; Research Biochemicals, Natick, M A; 10 µM), tetramethylrhodamine methyl ester (TMRM; Mitochondrial potential probe; Molecular probes; 10 nM), dihydrorhodamine 123 (DHR; reactive oxygen species indicator; Molecular Probes; 5 µM), z-val-ala-asp-fluorometylketone (z-vad-FMK; a pan-caspase inhibitor; Calbiochem; 200 µM), z-val-phe-CHO (Calpain Inhibitor III; Calbiochem; 10 µM).

Stocks of the following were prepared in $ddH_2O$ (10-20 mM) and diluted to their final concentrations in control buffer: MK-801 (NMDAR antagonist; 10 µM), Sodium nitroprusside (SNP; a nitric oxide donor; Sigma; 300 µM). $N^G$-nitro-L-arginine methyl ester (L-NAME; a nNOS inhibitor; Sigma, 100 µM).

Propidium iodide (PI; viability indicator; Molecular Probes Inc.) was prepared as a 1 mg/ml stock, and dissolved to 50 µg/ml final concentration. 10 mM manganese(III) tetrakis(4-benzoic acid) porphyrin (MnTBAP; $O_{2-}$ scavenger) stock was prepared by first dissolving the crystals in 100 µL of 1M NaOH, and then adding an equal volume of 1M HCl. This stock was diluted to its final concentration (200 µM) in control solution, and pH of 7.4 was confirmed prior to each use. MnTBAP, SNP and Nimodipine were protected from light at all times. Nimodipine, CNQX and MK-801 were always applied at concentrations of 2 µM, 10 µM and 10 µM, respectively (Sattler et al., 1998). All solutions were prepared under sterile conditions. All other chemicals were obtained from Sigma (St. Louis, Mo.).

Stretching of Cultured Neurons

The cultures, grown on silastic membranes as above, were placed in the Flexercell® FX-3000™ Strain Unit (Flexcell Int., Inc.), a computer-driven instrument that uses a vacuum pulse to deform the culture substrate. In all experiments, the cortical cultures were stretched to 130% of their original length for 1 s, inducing a sublethal injury as recently characterized by us (Arundine et al., 2003). The stretched neurons maintained cell membrane integrity, viability, and electrophysiological function.

Determination of Cell Death

Cell death was determined by serial quantitative measurements of propidium iodide (PI) fluorescence using a multiwell plate fluorescence scanner (Cytofluor II, PerSeptive Biosytems, Framingham, Mass., USA) as described previously (Sattler et al., 1997; Sattler et al., 1998). In brief, the culture medium in each tissue culture well was replaced with control solution containing 50 µg/ml PI, and a baseline fluorescence reading was taken. Sequential readings were then taken at appropriate intervals over the 20 h observation period. The fraction of dead cells in each culture at a given time was calculated as: Fraction dead=$(F_t-F_0)/F_{NMDA}$ Where Ft=PI fluorescence at time t, $F_o$=initial PI fluorescence at time zero and $F_{NMDA}$=background subtracted PI fluorescence of identical cultures from the same dissection and plating, 20-24 h after a 60 min exposure to 1 mM NMDA at 37° C. Based on manual observations at the time of validation of this technique, this NMDA exposure routinely produced near complete neuronal death in each culture but had no effect on surrounding glia (also see (Bruno et al., 1994; David et al., 1996; Sattler et al., 1997)). Adding Triton X-100 (0.1%) to cultures treated in this manner produced an additional 10-15% increase in PI fluorescence due to permeabilization of non-neuronal cell membranes, consistent with a 10-15% glial component in the cultures.

Experimental Protocols

All experiments were performed at 37° C. Unless otherwise indicated, all solutions contained nimodipine (2 µM) and CNQX (10 µM) to restrict the actions of applied NMDA to NMDARs by preventing the secondary activation of other pathways (Sattler et al., 1998). In general, the cultures were washed ×2 with control solution and immediately stretched to 130% of their original length for 1 s. After the stretch, they were washed ×1 with control solution alone or challenged with an additional treatment (e.g., NMDA) and placed at 37° C. for 1 h. They were then washed ×1 with control solution and then with control solution containing 50 µg/ml PI to obtain a baseline reading. In pilot studies, baseline readings obtained at this stage were similar to those obtained by staining the cells with PI prior to stretch. As the stretch causes splashing of the bath solution, staining with PI after stretch reduced biohazard potential and artifacts associated with PI outside the culture well. Unstretched controls were manipulated identically to stretched cultures.

Assessment of Mitochondrial Membrane Potential

Mitochondrial potential was measured with TMRM because it is believed to reduce mitochondrial respiration to lesser extent than other dyes such as rhodamine 123 or tetramethylrhodamine ethyl ester (Scaduto, Jr. and Grotyohann, 1999). Cultures were preincubated at 37° C. with 10 nM TMRM for 30 min. This concentration is well below that which is anticipated to quench TMRM fluorescence, and reductions in mitochondrial potential are manifest by reductions in whole cell fluorescence (e.g., FIG. 18B—effect of FCCP, a mitochondrial depolarizing agent). TMRM was maintained in the solution throughout the experiment. TMRM fluorescence was imaged on a Nikon Eclipse TE-2300 microscope using 20× objective (Nikon), a 510-560 nm bandpass excitation and 590 nm emission filter. Images were acquired using a Hamamatsu ORCA-ER digital camera and Simple PCI software (Nikon). Fluorescence from 10-30 cells was averaged and background subtracted for each image.

Assessment of ROS Production

The production of reactive oxygen species (ROS) was measured with DHR. In brief, DHR is oxidized to a fluorescent rhodamine-123 (Royall and Ischiropoulos, 1993), and the consequent rise in fluorescence may be used as an indicator of ROS production. DHR has been shown to be oxidized by superoxide anions (Rothe et al., 1991; Bueb et al., 1995; Ostrovidov et al., 1998), hydrogen peroxide (Royall and Ischiropoulos, 1993; Gow et al., 1999), peroxide radicals (Royall and Ischiropoulos, 1993; Gow et al., 1999) and peroxynitrite (Gilad et al., 1997).

ROS were measured as previously described (Tymianski et al., 1998; Aarts et al., 2003). In brief, cultures were pre-loaded for 30 min with 5 µM DHR and subjected to the experimental insult. DHR fluorescence was measured in a multiwell plate fluorescence scanner (Cytofluor II, PerSeptive Biosytems, Framingham, Mass., USA; 485 nm excitation, 530 emission). DHR fluorescence was normalized to baseline using the formula $(F_t-F_o)/F_0$; Where $F_r$=DHR fluorescence at time t, $F_o$=DHR fluorescence at time zero. DHR fluorescence images were also acquired using a microscope (465-495 nm excitation and 515-555 nm emission) as described above for TMRM.

DNA Fragmentation Assays

DNA fragmentation was examined using the terminal deoxynucleotidyl transferase-mediated end nick labeling (TUNEL) method (Gavrieli et al., 1992; Didenko and Hornsby, 1996; Didenko et al., 1998) and by DNA agarose gel electrophoresis (Hill et al., 2000).

TUNEL Assay: Nuclear DNA strand breaks were detected by enzymatically labeling free 3'-OH termini with modified nucleotides provided in the Apoptag kit (Intergen) using the manufacturer's instructions. Visualization of TUNEL-stained nuclei was achieved using an anti-digoxigenin antibody conjugated to a fluorescein or peroxidase reporter molecule (ApopTag Peroxidase Kits S7110 and S7100, respectively, Intergen). In fluorescence experiments, nuclei were counterstained using 5 ng/ml Hoechst 33258 (1:5000, Transduction Labs), and visualized using 465-495 nm excitation and 515-555 nm emission for fluorescein and 340 nm excitation and 510-40 nm emission for Hoechst. The number of TUNEL positive cells was expressed as a fraction of the total cell number in the field. In each culture, 4-8 random fields were quantified. Approximately 100-200 cells were counted per culture, and at least 3 experiments were performed for each set of counts.

DNA Gel Electrophoresis: DNA laddering was evaluated as described elsewhere (Hill et al., 2000). In brief, all tissue was collected from each culture well and pelleted by centrifugation (1000 rpm; 1 min). The cells were digested for 2 h at 56° C. in buffer containing (in mM) 10 Tris pH 8.0, 2 EDTA pH8, 400 NaCl, 0.5% SDS, 1 mg/ml proteinase K. Digest solution was subjected to phenol/chloroform extraction and total DNA was precipitated from the aqueous layer with an equal volume of 100% ethanol. The DNA pellet was dried, dissolved in 50 µl ddH$_2$O and kept overnight at 4° C. 10 µg DNA was prepared on a 2% agarose gel. Gels were stained with ethidium bromide and photographed.

Protein Harvest for Immunoblots

All tissue was collected from each culture well and centrifuged to obtain a total cell pellet. The pellet was washed with phosphate buffered saline (PBS) containing phenylmethylsulfonyl fluoride (pmsf) to inhibit intracellular proteases. Subsequent to the final wash, the pellet was resuspended in Triton lysis buffer containing (in mM): 150 NaCl, 20 Tris pH 7.4, 20 NaF, 0.1 sodium vanadate, 1% Triton X-100, 1 PMSF). In experiments necessitating cytosolic and nuclear protein fractions, fractioned lysates were prepared according to the method of Borer et al. (1989). In brief, harvested cells were reconstituted with hypotonic buffer ((in mM) 10 HEPES pH7.9, 10 KCl, 0.1 EDTA, 0.1 EGTA, 1 PMSF), and incubated on ice for 15 min. NP-40 (0.5% final concentration) was added to cell suspension, vortexed and incubated for 1 min at room temperature (RT). Suspension was centrifuged (10,000 rpm; 30 sec, RT), and supernatant and pellet fractions were separated. The supernatant fraction (cytosolic fraction) was reconstituted in Triton lysis buffer by adding 5× stock buffer directly to the fraction. The pellet fraction (nuclear fraction) was washed ×2 with hypotonic buffer (containing 0.5% NP-40), and the final pellet was reconstituted with 1× Triton lysis buffer.

The protein content of all fractions was assessed using the BioRAD DC Protein assay kit (Bio-Rad, Mississauga, Ontario) and the samples stored at −80° C. until the time of analysis.

Immunoblotting

Protein samples were immunoblotted as previously described (Jones et al., 1997; Sattler et al., 2000). The blotted proteins were probed using the following antibodies: Primary: rabbit polyclonal anti-caspase 3 (StressGen, 1:1000); mouse monoclonal anti-AIF (Santa Cruz Biotechnology, 1:800); mouse monoclonal anti-nNOS(NOS type 1) IgG2a (Transduction Laboratories, 1:2000); mouse monoclonal anti-endonuclease g (ProSci Inc., 1:1000). Secondary antibodies were: sheep anti-mouse Ig or donkey anti-rabbit Ig antibodies conjugated to horseradish peroxidase (Amersham Life Science, diluted 1:3000 in TBS-T).

Immunostaining

Cultures were fixed with warm 4% paraformaldehyde and 4% sucrose in PBS for 20 min, permeabilized with 0.1% Triton X-100 for 10 min at 4° C., and blocked with 10% goat serum in PBS for 1 h at RT. Immunofluorescence was visualized with an inverted Nikon microscope using a 40× oil immersion lens. FITC, rhodamine and Hoechst were visualized using 465-495 excitation and 515-555 nm emission, 510-560 nm excitation and 590 nm emission, and 340 nm excitation and 510 nm emission, respectively. Active caspase 3 was labelled by incubating the cultures with a purified rabbit monoclonal anti-active caspase 3 antibody (1:300; BD PharMingen) and a fluorescein-conjugated goat anti-mouse IgG secondary antibody (1:500; Transduction Labs). Nitrotyrosine was labelled by incubating the cultures with a rabbit polyclonal α-nitrotyrosine primary antibody (1:300; Upstate) and a rhodamine-conjugated goat anti-rabbit IgG secondary antibody (1:500; Transduction Labs). AIF was labelled by incubating the cultures with an AIF antibody (1:200; Santa Cruz, (Zhang et al., 2002)) and a rhodamine-conjugated goat anti-mouse IgG secondary antibody (1:500; Transduction Labs). In some experiments, nuclei were counter-stained with Hoechst 33258 (1:5,000, Transduction Labs).

Synthetic Tat Peptides and Plasmid Construction

Tat-conjugated peptides were synthesized at the Advanced Protein Technology Centre (Hospital for Sick Kids, Toronto, Ontario). Tat peptides were conjugated to either the terminal 9 amino acids of the NMDA receptor NR2B subunit (Tat-NR2B9c) or to the mutated form (Serine and Valine replaced with Alanine; Tat-NR2B-AA). The Tat-peptide sequences are as in FIG. 23B.

Transducible proteins were constructed by cloning PCR products in frame into the pTat-HA bacterial expression vector containing an N-terminal 6-histidine leader followed by the 11 amino acid Tat protein transduction domain, a hemaglutinin (HA) tag and a polylinker site (Kind gift of S. Dowdy, Washington University, St. Louis). The transducible pTat-PDZ1-2 and pTat-GK fusion proteins were constructed as follows: Oligonucleotides PDZ1-2 (S 5'-ggtaccgaggagarcacattggaa-3' and AS 5-gaattctgggggagcatagctgtc-3') and GK (S 5'-cgggtaccgctcgtcccatcatcatc-3' and AS 5'-gaattctcagagtctctctcgggctgg-3') were used to generate PSD-95 fragments with 5' KpnI site and 3' EcoRI site for subcloning into the pTAT-HA vector polylinker site. Both the PCR products and pTAT-HA plasmid were digested with KpnI and EcoRI, ligated, and subsequently transformed into competent DH5α bacterial cells (Invitrogen, Burlington, Ontario). Plasmids were isolated and re-transformed into BL21 (DE3)pLysS bacterial cells (Invitrogen, Burlington, Ontario). To determine whether the transformations were successful homogenates of AMP-resistant colonies were run on SDS-PAGE, transferred to nitrocellulose membranes and probed with mouse HA. 11 antibody against the hemagglutinin tag (Covance/BabCo, Princeton, N.J.). HA-tagged proteins were detected using a goat anti-mouse secondary antibody conjugated to horseradish peroxidase and visualized using enhanced chemiluminescence. Clones expressing the fusion protein were harvested by sonication in 8M urea and a Ni-NTA column (Amersham) was used to extract the fusion proteins. The proteins were desalted on PD-10 columns (Amersham), protease inhibitors were added (1 µg/ml aprotinin, 1 µg/ml leupeptin), and the protein concentration determined using the Bio-Rad DC Protein assay (Bio-Rad, Mississauga, Ontario).

Figure 28:
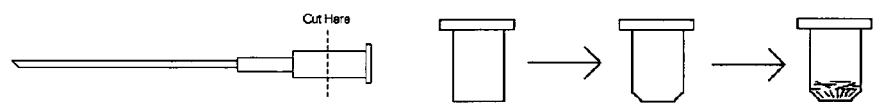
FIG. 28. Diagram of a modified Leur-Loc for use with a fluid percussion injury device.

Induction of Lateral Fluid Percussion Injury and Injection of Agents into the Experimental Animals Adult male Sprague-Dawley rats weighing approximately 350 g were ordered from Charles River and anesthesia was induced using a gaseous mixture of 1:2 oxygen:nitrous oxide with 2% halothane. The halothane level was reduced to 1% during surgical manipulations and weights were recorded prior to preparatory surgery. The preparatory surgery for these experiments included the cannulation of the left femoral vein and a 5 mm diameter craniotomy. The venous cannula is sealed and tucked inside the animal whereupon the wound is sutured. The center of the craniotomy lies about 2.5 mm to the right of the sagittal suture, between the bregma and lambda. A modified Leur-loc is attached to the perimeter of the craniotomy with superglue (FIG. 28).

Figure 29:
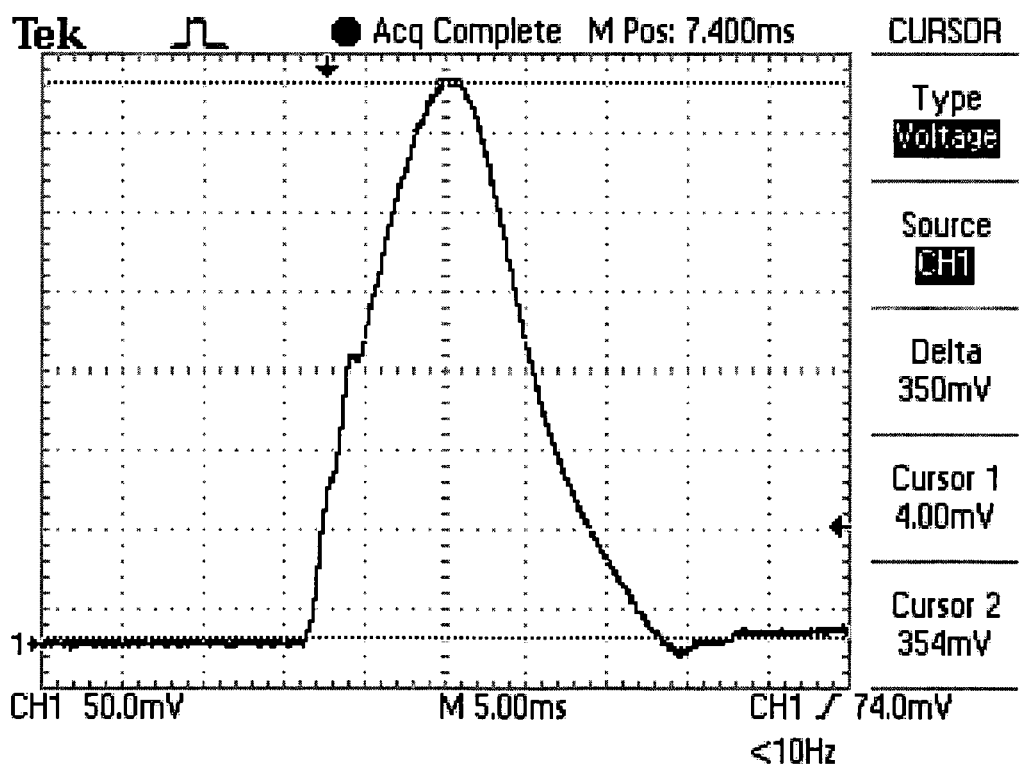
FIG. 29. Diagram of a reading from a fluid percussion injury device.

Dental acrylic (GC America Inc, Alsip, Ill.) is applied around the modified Leur-loc to seal it into place. A small piece of gelfoam is placed into the opening and the skin is sutured over the entire setup. The animal is then returned to its cage. The following day, the animal is re-anesthetized, weighed, and its wound is re-opened. The gelfoam is removed and the animal is attached to the fluid percussion device via the modified Leur-loc. At this time, the animal is given a ~20 ms saline injection at approximately 2.4 atmospheres (350 mV on the oscilloscope) using the fluid percussion injury device (Custom Design & Fabrication, Richmond, Va.) (FIG. 29).

On occasion, the animal ceases spontaneous breathing following the injury and 1-2 chest compressions are required for resuscitation. The modified Leur-loc along with the dental acrylic is removed en bloc immediately following the injury. The animal is placed on 100% oxygen while its wound is cleaned and resealed with Vetbond tissue adhesive (3M Worldwide, Maplewood, Minn.). The rat's body temperature during the recovery time is maintained at 37° C. with a homeothermic warming blanket (Harvard Bioscience Inc, Holliston, Mass.). The amount of time necessary for the righting reflex to return is recorded and the animal is placed back into its cage. At 3 h post-injury, the animal is re-anesthetized and weighed again. The wound overlying the femoral cannula is opened and the cannula is cleaned out using heparinized saline. The animal is then given a 3 nmol/g injection of Tat-KLSSIESDV SEQ ID NO:4, Tat-KLSSIETDV SEQ ID NO:5 or Tat-KLSSIEASDA SEQ ID NO:12 (inactive control) via the cannula. The cannula is sealed, tucked again into the animal, and the wound is re-sutured. At 24 h post-injury, the animal is re-anesthetized and weighed again. The rat is transcardially perfused using heparinized saline to clean out the cardiovascular system, followed by a 4% formalin fixative solution. The rat is decapitated and left in the fixative solution overnight. The brain is extracted the following day and processed. The volume of damaged brain (FIG. 26, right graph) is assessed according to the same methods as described in Aarts et al., 2002, for assessing stroke volumes. The fraction of dead cells was derived from counts of all fluoro-Jade stained nuclei in the cortex and hippocampus of 8 coronal brain sections per animal (FIG. 26, inset), normalized to the number of dead cells in the group of animals treated with control drug.

In therapeutic applications, the peptide replacement agents are administered to a patient suffering from ischemia or traumatic injury to the brain or spinal cord in an amount sufficient to at least partially inhibit the binding between N-methyl-D-aspartate receptors and neuronal proteins. In prophylactic applications, the peptide replacement agents are administered to a patient susceptible to ischemia in an amount sufficient to at least partially inhibit binding between N-methyl-D-aspartate receptors and neuronal proteins. An amount adequate to accomplish this is defined as a "therapeutically effective dose" or an "effective inhibiting amount". Amounts effective for these uses will depend upon the severity of the ischemia or traumatic injury and the general state of the patient's health. Means of assessing ischemia or traumatic brain or spinal cord injury are well known to those skilled in the art.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated. The disclosures of all patents, patent applications and publications cited herein are hereby incorporated herein by reference to the extent that they describe materials, methods or other details supplementary to those set forth herein.

REFERENCES

1. A. Ghosh, M. E. Greenberg, Science 268, 239 (1995); T. V. Bliss, G. L. Collingridge, Nature 361, 31 (1993).
2. J. W. Olney, Kainic acid as a tool in neurobiology., E. G. McGeer, J. W. Olney and P. L. McGeer, Eds. (Raven Press, New York, 1978), p. 95; S. M. Rothman, J. W. Olney, TINS 10, 299 (1987); D. W. Choi, Ann NY Acad Sci 747, 162 (1994).
3. S. A. Lipton, P. A. Rosenberg, New Eng J Med 330, 613 (1994).
4. R. Sattler, M. P. Charlton, M. Hafner, M. Tymianski, J Neurochem 71, 2349 (1998); M. Tymianski, M. P. Charlton, P. L. Carlen, C. H. Tator, J Neurosci 13, 2085 (1993).
5. K. O. Cho, C. A. Hunt, M. B. Kennedy, Neuron 9, 929 (1992).
6. H. C. Kornau, L. T. Schenker, M. B. Kennedy, P. H. Seeburg, Science 269, 1737 (1995); J. E. Brenman, K. S. Christopherson, S. E. Craven, A. W. McGee, D. S. Bredt, J Neurosci 16, 7407 (1996); B. M. Muller, et al., Neuron 17, 255 (1996).
7. H. Dong, et al., Nature 386, 279 (1997); P. R. Brakeman, et al., Nature 386, 284 (1997).
8. S. E. Craven, D. S. Bredt, Cell 93, 495 (1998); M. Niethammer, et al., Neuron 20, 693 (1998); J. H. Kim, D. Liao, L. F. Lau, R. L. Huganir, Neuron 20, 683 (1998); T. Tezuka, H. Umemori, T. Akiyama, Nakanishi, T. Yamamoto, Proc Natl Acad Sci USA 96, 435 (1999).
9. Hertz, E., Yu, A. C. H., Hertz, L., Juurlink, B. H. J. & Schousboe, A. in A dissection and tissue culture manual of the nervous system (eds Shahar, A., de Vellis, J., Vernadakis, A. & Haber, B.) Vol. 1, 183-186 (Alan R. Liss Inc., New York, 1989).
10. S. F. Altschul, et al., Nucleic Acids Research 25, 3389 (1997).
11. O. T. Jones, et al., J Neurosci 17, 6152 (1997).
12. V. L. Dawson, T. M. Dawson, E. D. London, D. S. Bredt, S. H. Snyder, Proc Natl Acad Sci USA 88, 6368 (1991); V. L. Dawson, T. M. Dawson, D. A. Bartley, G. R. Uhl, S. H. Snyder, J Neurosci 13, 2651 (1993); T. M. Dawson, D. S. Bredt, M. Fotuhi, P. M. Hwang, S. H. Snyder, Proc Natl Acad Sci USA 88, 7797 (1991).
13. Xiong, Z., Lu, W. & MacDonald, J. F. proc Natl Acad Sci USA 94, 7012-7017 (1997).
14. R. Sattler, M. P. Charlton, M. Hafner, M. Tymianski, J Cereb Blood Flow Metab 17, 455 (1997).
15. N. Burnashev, Z. Zhou, E. Neher, B. Sakmann, J Physiol 485, 403 (1995).
16. M. Migaud, et al., Nature 396, 433 (1998).
17. J. R. Brorson, P. T. Schumacker, H. Zhang, J Neurosci 19, 147 (1999).
18. S. R. Jaffrey, S. H. Snyder, Annual Review of Cell & Developmental Biology 11, 417 (1995).
19. S. R. Jaffrey, S. H. Snyder, Annual Review of Cell & Developmental Biology 11, 417 (1995).
20. T. Pawson and J. D. Scott, Science 278, 2075-2080 (1997).
21. M. Sheng, Proc. Natl. Acad. Sci. U.S.A 98, 7058-7061 (2001).
22. J. E. Brenman et al., Cell 84, 757-767 (1996).
23. V. L. Dawson, T. M. Dawson, E. D. London, D. S. Bredt, S. H. Snyder, Proc Natl Acad Sci USA 88, 6368-6371 (1991).

24. M. Migaud et al., Nature 396, 433-439 (1998).
25. R. Sattler et al., Science 284, 1845-1848 (1999).
26. R. P. Simon, J. H. Swan, B. S. Meldrum, Science 226, 850-852 (1984).
27. A. S. Fix et al., Exp Neurol 123, 204-215 (1993).
28. S. M. Davis et al., Stroke 31, 347-354 (2000).
29. G. F. Morris et al., J. Neurosurg. 91, 737-743 (1999).
30. S. R. Schwarze, A. Ho, A. Vocero-Akbani, S. F. Dowdy, Science 285, 1569-1572 (1999).
31. D. A. Mann and A. D. Frankel, EMBO J. 10, 1733-1739 (1991).
32. R. Sattler, M. P. Charlton, M. Haffner, M. Tymianski, J Neurochem 71, 2349-2364 (1998).
33. R. Sattler, Z. Xiong, W. Y. Lu, J. F. MacDonald, M. Tymianski, J. Neurosci. 20, 22-33 (2000).
34. S. R. Jaffrey and S. H. Snyder, Annual Review of Cell & Developmental Biology 11, 417-440 (1995).
35. U. Kistner, C. C. Garner, M. Linial, FEBS Lett. 359, 159-163 (1995).
36. E. Z. Longa, P. R. Weinstein, S. Carlson, R. Cummins, Stroke 20, 84-91 (1989).
37. L. Belayev, O. F. Alonso, R. Busto, W. Zhao, M. D. Ginsberg, Stroke 27, 1616-1622 (1996).
38. J. B. Bederson et al., Stroke 17, 472-476 (1986).
39. M. De Ryck, J. van Reempts, M. Borgers, A. Wauquier, P. A. Janssen, Stroke 20, 1383-1390 (1989).
40. Aarts M, Iihara K, Wei W L, Xiong Z G, Arundine M, Cerwinski W, MacDonald J F, Tymianski M (2003) A key role for TRPM7 channels in anoxic neuronal death. Cell 115: 863-877.
41. Aarts M, Liu Y, Liu L, Besshoh S, Arundine M, Gurd J W, Wang Y T, Salter M W, Tymianski M (2002) Treatment of ischemic brain damage by perturbing NMDA receptor-PSD-95 protein interactions. Science 298: 846-850.
42. Ahmed S M, Rzigalinski B A, Willoughby K A, Sitterding H A, Ellis E F (2000) Stretch-induced injury alters mitochondrial membrane potential and cellular ATP in cultured astrocytes and neurons. J Neurochem 74: 1951-1960.
43. Ahmed S M, Weber J T, Liang S, Willoughby K A, Sitterding H A, Rzigalinski B A, Ellis E F (2002) NMDA receptor activation contributes to a portion of the decreased mitochondrial membrane potential and elevated intracellular free calcium in strain-injured neurons. J Neurotrauma 19: 1619-1629.
44. Allen R T, Hunter W J, III, Agrawal D K (1997) Morphological and biochemical characterization and analysis of apoptosis. J Pharmacol Toxicol Methods 37: 215-228.
45. Amar A P, Levy M L (1999) Pathogenesis and pharmacological strategies for mitigating secondary damage in acute spinal cord injury. Neurosurgery 44: 1027-1039.
46. Arundine M, Chopra G K, Wrong A W, Lei S, Aarts M, MacDonald J F, Tymianski M (2003) Enhanced Vulnerability to NMDA Toxicity in Sublethal Traumatic Neuronal Injury In-Vitro. J Neurotrauma 20: 1377-1395.
47. Bading H, Ginty D D, Greenberg M E (1993) Regulation of gene expression in hippocampal neurons by distinct calcium signaling pathways. Science 260: 181-186.
48. Beattie M S, Farooqui A A, Bresnahan J C (2000) Review of current evidence for apoptosis after spinal cord injury. J Neurotrauma 17: 915-925.
49. Beattie M S, Harrington A W, Lee R, Kim J Y, Boyce S L, Longo F M, Bresnahan J C, Hempstead B L, Yoon S O (2002) ProNGF induces p75-mediated death of oligodendrocytes following spinal cord injury. Neuron 36: 375-386.
50. Bindokas V P, Jordan J, Lee C C, Miller R J (1996) Superoxide production in rat hippocampal neurons: selective imaging with hydroethidine. J Neurosci 16: 1324-1336.
51. Bonfoco E, Krainc D, Ankarcrona M, Nicotera P, Lipton S A (1995) Apoptosis and necrosis: two distinct events induced, respectively, by mild and intense insults with N-methyl-D-aspartate or nitric oxide/superoxide in cortical cell cultures. Proc Natl Acad Sci USA 92: 7162-7166.
52. Bonfoco E, Leist M, Zhivotovsky B, Orrenius S, Lipton S A, Nicotera P (1996) Cytoskeletal breakdown and apoptosis elicited by NO donors in cerebellar granule cells require NMDA receptor activation. J Neurochem 67: 2484-2493.
53. Borer R A, Lehner C F, Eppenberger H M, Nigg E A (1989) Major nucleolar proteins shuttle between nucleus and cytoplasm. Cell 56: 379-390.
54. Brenman J E, Bredt D S (1997) Synaptic signaling by nitric oxide. Current Opin Neurobiol 7: 374-378.
55. Brenman J E, Chao D S, Gee S H, McGee A W, Craven S E, Santillano D R, Wu Z, Huang F, Xia H, Peters M F, Froehner S C, Bredt DS (1996) Interaction of nitric oxide synthase with the postsynaptic density protein PSD-95 and alpha1-syntrophin mediated by PDZ domains. Cell 84: 757-767.
56. Brenman J E, Topinka J R, Cooper E C, McGee A W, Rosen J, Milroy T, Ralston H J, Bredt DS (1998) Localization of postsynaptic density-93 to dendritic microtubules and interaction with microtubule-associated protein 1A. J Neurosci 18: 8805-8813.
57. Brown J I, Baker A J, Konasiewicz S J, Moulton R J (1998) Clinical significance of CSF glutamate concentrations following severe traumatic brain injury in humans. J Neurotrauma 15: 253-263.
58. Bruno V M G, Goldberg M P, Dugan L L, Giffard R G, Choi D W (1994) Neuroprotective effect of hypothermia in cortical cultures exposed to oxygen-glucose deprivation or excitatory amino acids. J Neurochem 63: 1398-1406.
59. Budd S L, Tenneti L, Lishnak T, Lipton S A (2000) Mitochondrial and extramitochondrial apoptotic signaling pathways in cerebrocortical neurons. Proc Natl Acad Sci USA 97: 6161-6166.
60. Bueb J L, Gallois A, Schneider J C, Parini J P, Tschirhart E (1995) A double-labelling fluorescent assay for concomitant measurements of [C2+]i and O2. production in human macrophages. Biochim Biophys Acta 1244: 79-84.
61. Centers for Disease Control and Prevention. Traumatic injury in the United States: An interim report to Congress. Centers for Disease Control and Prevention. 2001. Ref Type: In Press
62. Charriaut-Marlangue C, Ben Ari Y (1995) A cautionary note on the use of the TUNEL stain to determine apoptosis. Neuroreport 7: 61-64.
63. Choi D W (1987) Ionic dependence of glutamate neurotoxicity. J Neurosci 7: 369-379.
64. Choi D W (1992) Excitotoxic cell death. J Neurobiol 23: 1261-1276.
65. Clark R S, Kochanek P M, Dixon C E, Chen M, Marion D W, Heineman S, DeKosky S T, Graham S H (1997) Early neuropathologic effects of mild or moderate hypoxemia after controlled cortical impact injury in rats. J Neurotrauma 14: 179-189.
66. Conti A C, Raghupathi R, Trojanowski J Q, McIntosh T K (1998) Experimental brain injury induces regionally distinct apoptosis during the acute and delayed post-traumatic period. J Neurosci 18: 5663-5672.

67. Cote J, Ruiz-Carrillo A (1993) Primers for mitochondrial DNA replication generated by endonuclease G. Science 261: 765-769.
68. Danial N N, Korsmeyer S J (2004) Cell death: critical control points. Cell 116: 205-219.
69. David J C, Yamada K A, Bagwe M R, Goldberg M P (1996) AMPA receptor activation is rapidly toxic to cortical astrocytes when desensitization is blocked. J Neurosci 16: 200-209.
70. Dawson V L, Dawson T M, London E D, Bredt D S, Snyder S H (1991) Nitric oxide mediates glutamate neurotoxicity in primary cortical cultures. Proc Natl Acad Sci USA 88: 6368-6371.
71. Day B J, Fridovich I, Crapo J D (1997) Manganic porphyrins possess catalase activity and protect endothelial cells against hydrogen peroxide-mediated injury. Arch Biochem Biophys 347: 256-262.
72. Didenko V V, Hornsby P J (1996) Presence of double-strand breaks with single-base 3' overhangs in cells undergoing apoptosis but not necrosis. J Cell Biol 135: 1369-1376.
73. Didenko V V, Tunstead J R, Hornsby P J (1998) Biotin-labeled hairpin oligonucleotides: probes to detect double-strand breaks in DNA in apoptotic cells. Am J Pathol 152: 897-902.
74. Dong H, Fazzaro A, Xiang C, Korsmeyer S J, Jacquin M F, McDonald J W (2003) Enhanced oligodendrocyte survival after spinal cord injury in Bax-deficient mice and mice with delayed Wallerian degeneration. J Neurosci 23: 8682-8691.
75. Dugan L L, Sensi S L, Canzoniero L M T, Handran S D, Rothman S M, Lin T S, Goldberg M P, Choi D W (1995) Mitochondrial production of reactive oxygen species in cortical neurons following exposure to N-methyl-D-aspartate. J Neurosci 15: 6377-6388.
76. Ehrenberg B, Montana V, Wei M D, Wuskell J P, Loew L M (1988) Membrane potential can be determined in individual cells from the nemstian distribution of cationic dyes. Biophys J 53: 785-794.
77. Eldadah B A, Faden A I (2000) Caspase pathways, neuronal apoptosis, and CNS injury. J Neurotrauma 17: 811-829.
78. Ellis E F, McKinney J S, Willoughby K A, Liang S, Povlishock J T (1995) A new model for rapid stretch-induced injury of cells in culture: characterization of the model using astrocytes. J Neurotrauma 12: 325-339.
79. Enari M, Sakahira H, Yokoyama H, Okawa K, Iwamatsu A, Nagata S (1998) A caspase-activated DNase that degrades DNA during apoptosis, and its inhibitor ICAD. Nature 391: 43-50.
80. Faden A I (2002) Neuroprotection and traumatic brain injury: theoretical option or realistic proposition. Curr Opin Neurol 15: 707-712.
81. Faden A I, Demediuk P, Panter S S, Vink P (1989), The role of excitatory amino acids and NMDA receptors in traumatic brain injury. Science 244: 798-800.
82. Fearnhead H O, Dinsdale D, Cohen G M (1995) An interleukin-1 beta-converting enzyme-like protease is a common mediator of apoptosis in thymocytes. FEBS Lett 375: 283-288.
83. Gavrieli Y, Sherman Y, Ben-Sasson S A (1992) Indentification of programmed cell death in situ via specific labeling of nuclear DNA fragmentation. J Cell Biol 119: 493-501.
84. Gerschenson L E, Rotello R J (1992) Apoptosis: a different type of cell death. FASEB J 6: 2450-2455.
85. Ghosh A, Ginty D D, Bading H, Greenberg M E (1994) Calcium regulation of gene expression in neuronal cells. [Review] [39 refs]. Journal of Neurobiology 25: 294-303.
86. Gil-Parrado S, Femandez-Montalvan A, Assfalg-Machleidt I, Popp O, Bestvater F, Holloschi A, Knoch T A, Auerswald E A, Welsh K, Reed J C, Fritz H, Fuentes-Prior P, Spiess E, Salvesen G S, Machleidt W (2002) Ionomycin-activated calpain triggers apoptosis. A probable role for Bcl-2 family members. J Biol Chem 277: 27217-27226.
87. Gilad E, Cuzzocrea S, Zingarelli B, Salzman A L, Szabo C (1997) Melatonin is a scavenger of peroxynitrite. Life Sci 60: L169-L174.
88. Gow A J, Branco F, Christofidou-Solomidou M, Black-Schultz L, Albelda S M, Muzykantov V R (1999) Immunotargeting of glucose oxidase: intracellular production of $H(2)O(2)$ and endothelial oxidative stress. Am J Physiol 277: L271-L281.
89. Grasl-Kraupp B, Ruttkay-Nedecky B, Koudelka H, Bukowska K, Bursch W, Schulte-Hermann R (1995) In situ detection of fragmented DNA (TUNEL assay) fails to discriminate among apoptosis, necrosis, and autolytic cell death: a cautionary note. Hepatology 21: 1465-1468.
90. Hardingham G E, Bading H (2003) The Yin and Yang of NMDA receptor signalling. Trends Neurosci 26: 81-89.
91. Hewett S J, Csernansky C A, Choi D W (1994) Selective potentiation of NMDA-induced neuronal injury following induction of astrocytic iNOS. Neuron 13: 487-494.
92. Hewett S J, Muir J K, Lobner D, Symons A, Choi D W (1996) Potentiation of oxygen-glucose deprivation-induced neuronal death after induction of iNOS. Stroke 27: 1586-1591.
93. Hill I E, Murray C, Richard J, Rasquinha I, MacManus J P (2000) Despite the internucleosomal cleavage of DNA, reactive oxygen species do not produce other markers of apoptosis in cultured neurons. Exp Neurol 162: 73-88.
94. Ishimaru M J, Ikonomidou C, Tenkova T I, Der T C, Dikranian K, Sesma M A, Olney J W (1999) Distinguishing excitotoxic from apoptotic neurodegeneration in the developing rat brain. J Comp Neurol 408: 461-476.
95. Jones O T, Bernstein G M, Jones E J, Jugloff D G, Law M, Wong W, Mills L R (1997) N-Type calcium channels in the developing rat hippocampus: subunit, complex, and regional expression. J Neurosci 17: 6152-6164.
96. Keane R W, Kraydieh S, Lotocki G, Alonso O F, Aldana P, Dietrich W D (2001) Apoptotic and antiapoptotic mechanisms after traumatic brain injury. J Cereb Blood Flow Metab 21: 1189-1198.
97. Kim E, Naisbitt S, Hsuch Y P, Rao A, Rothschild A, Craig A M, Sheng M (1997) GKAP, a novel synaptic protein that interacts with the guanylate kinase-like domain of the PSD-95/SAP90 family of channel clustering molecules. J Cell Biol 136: 669-678.
98. Kim J H, Liao D, Lau L F, Huganir R L (1998) SynGAP: a synaptic RasGAP that associates with the PSD-95/SAP90 protein family. Neuron 20: 683-691.
99. Kistner U, Garner C C, Linial M (1995) Nucleotide binding by the synapse associated protein SAP90. FEBS Lett 359: 159-163.
100. Kojima H, Nakatsubo N, Kikuchi K, Urano Y, Higuchi T, Tanaka J, Kudo Y, Nagano T (1998) Direct evidence of NO production in rat hippocampus and cortex using a new fluorescent indicator: DAF-2 DA. Neuroreport 9: 3345-3348.
101. Kornau H C, Schenker L T, Kennedy M B, Seeburg P H (1995) Domain interaction between NMDA receptor subunits and the postsynaptic density protein PSD-95. Science 269: 1737-1740.

102. Laplaca M C, Lee V M, Thibault L E (1997) An in vitro model of traumatic neuronal injury: loading rate-dependent changes in acute cytosolic calcium and lactate dehydrogenase release. J Neurotrauma 14: 355-368.
103. Leker R R, Shohami E (2002) Cerebral ischemia and trauma-different etiologies yet similar mechanisms: neuroprotective opportunities. Brain Res Brain Res Rev 39: 55-73.
104. Lewen A, Matz P, Chan P H (2000) Free radical pathways in CNS injury. J Neurotrauma 17: 871-890.
105. Liou A K, Clark R S, Henshall D C, Yin X M, Chen J (2003) To die or not to die for neurons in ischemia, traumatic brain injury and epilepsy: a review on the stress-activated signaling pathways and apoptotic pathways. Prog Neurobiol 69: 103-142.
106. Lipton P (1999) Ischemic cell death in brain neurons. Physiol Rev 79: 1431-1568.
107. Loew L M, Tuft R A, Carrington W, Fay F S (1993) Imaging in five dimensions: time-dependent membrane potentials in individual mitochondria. Biophys J 65: 2396-2407.
108. Lorenzo H K, Susin S A (2004) Mitochondrial effectors in caspase-independent cell death. FEBS Lett 557: 14-20.
109. Mann D A, Frankel A D (1991) Endocytosis and targeting of exogenous HIV-1 Tat protein. EMBO J. 10: 1733-1739.
110. Marshall L F (2000) Epidemiology and cost of central nervous system injury. Clin Neurosurg 46: 105-112.
111. McCollum A T, Nasr P, Estus S (2002) Calpain activates caspase-3 during UV-induced neuronal death but only calpain is necessary for death. J Neurochem 82: 1208-1220.
112. Migaud M, Charlesworth P, Dempster M, Webster L C, Watabe A M, Makhinson M, He Y, Ramsay M F, Morris R G M, Morrison J H, O'Dell T J, Grant S G N (1998) Enhanced long-term potentiation and impaired learning in mice with mutant postsynaptic density-95 protein. Nature 396: 433-439.
113. Naisbitt S, Kim E, Tu J C, Xiao B, Sala C, Valtschanoff J, Weinberg R J, Worley P F, Sheng M (1999) Shank, a novel family of postsynaptic density proteins that binds to the NMDA receptor/PSD-95/GKAP complex and cortactin. Neuron 23: 569-582.
114. National Center for Health Statistics (1997) Data file documentation, National Hospital Discharge Survey 1980-1995. Centers for Disease Control and Prevention.
115. Newcomb J K, Zhao X, Pike B R, Hayes R L (1999) Temporal profile of apoptotic-like changes in neurons and astrocytes following controlled cortical impact injury in the rat. Exp Neurol 158: 76-88.
116. Nicholls D G, Budd S L (1998) Mitochondria and neuronal glutamate excitotoxicity. Biochim Biophys Acta 1366: 97-112.
117. Nicholls D G, Budd S L (2000) Mitochondria and neuronal survival. Physiol Rev 80: 315-360.
118. Niethammer M, Valtschanoff J G, Kapoor T M, Allison D W, Weinberg R J, Craig A M, Sheng M (1998) CRIPT, a novel postsynaptic protein that binds to the third PDZ domain of PSD-95/SAP90. Neuron 20: 693-707.
119. NIH (1999) Consensus conference. Rehabilitation of persons with traumatic brain injury. NIH Consensus Development Panel on Rehabilitation of Persons With Traumatic Brain Injury. JAMA 282: 974-983.
120. Ostrovidov S, Franck P, Capiaumont J, Dousset B, Belleville F (1998) Effects of $H_2O_2$ on the growth, secretion, and metabolism of hybridoma cells in culture. In Vitro Cell Dev Biol Anim 34: 259-264.
121. Patel M, Day B J, Crapo J D, Fridovich I, McNamara J O (1996) Requirement for superoxide in excitotoxic cell death. Neuron 16: 345-355.
122. Petronilli V, Penzo D, Scorrano L, Bernardi P, Di Lisa F (2001) The mitochondrial permeability transition, release of cytochrome c and cell death. Correlation with the duration of pore openings in situ. J Biol Chem 276: 12030-12034.
123. Pike B R, Zhao X, Newcomb J K, Glenn C C, Anderson D K, Hayes R L (2000) Stretch injury causes calpain and caspase-3 activation and necrotic and apoptotic cell death in septo-hippocampal cell cultures. J Neurotrauma 17: 283-298.
124. Raghupathi R, Graham D I, McIntosh T K (2000) Apoptosis after traumatic brain injury. J Neurotrauma 17: 927-938.
125. Rami A, Ferger D, Krieglstein J (1997) Blockade of calpain proteolytic activity rescues neurons from glutamate excitotoxicity. Neurosci Res 27: 93-97.
126. Reiter C D, Teng R J, Beckman J S (2000) Superoxide reacts with nitric oxide to nitrate tyrosine at physiological pH via peroxynitrite. J. Biol. Chem.
127. Reynolds I J, Hastings T G (1995) Glutamate induces the production of reactive oxygen species in cultured forebrain neurons following NMDA receptor activation. J Neurosci 15: 3318-3327.
128. Rink A, Fung K M, Trojanowski J Q, Lee V M, Neugebauer E, McIntosh T K (1995) Evidence of apoptotic cell death after experimental traumatic brain injury in the rat. Am J Pathol 147: 1575-1583.
129. Rothe G, Emmendorffer A, Oser A, Roesler J, Valet G (1991) Flow cytometric measurement of the respiratory burst activity of phagocytes using dihydrorhodamine 123. J Immunol Methods 138: 133-135.
130. Royall J A, Ischiropoulos H (1993) Evaluation of 2',7'-dichlorofluorescin and dihydrorhodamine 123 as fluorescent probes for intracellular $H_2O_2$ in cultured endothelial cells. Arch Biochem Biophys 302: 348-355.
131. Sakahira H, Enari M, Nagata S (1998) Cleavage of CAD inhibitor in CAD activation and DNA degradation during apoptosis. Nature 391: 96-99.
132. Sattler R, Charlton M P, Hafner M, Tymianski M (1997) Determination of the time-course and extent of neurotoxicity at defined temperatures in cultured neurons using a modified multi-well plate fluorescence scanner. J Cereb Blood Flow Metab 17: 455-463.
133. Sattler R, Charlton M P, Hafner M, Tymianski M (1998) Distinct influx pathways, not calcium load, determine neuronal vulnerability to calcium neurotoxicity. J Neurochem 71: 2349-2364.
134. Sattler R, Xiong Z, Lu W Y, Hafner M, MacDonald J F, Tymianski M (1999) Specific coupling of NMDA receptor activation to nitric oxide neurotoxicity by PSD-95 protein. Science 284: 1845-1848.
135. Sattler R, Xiong Z, Lu W Y, MacDonald J F, Tymianski M (2000) Distinct roles of synaptic and extrasynaptic NMDA receptors in excitotoxicity. J Neurosci 20: 22-33.
136. Scaduto R C, Jr., Grotyohann L W (1999) Measurement of mitochondrial membrane potential using fluorescent rhodamine derivatives. Biophys J 76: 469-477.
137. Schwarze S R, Ho A, Vocero-Akbani A, Dowdy S F (1999) In vivo protein transduction: delivery of a biologically active protein into the mouse [see comments]. Science 285: 1569-1572.
138. Shah P T, Yoon K W, Xu X M, Broder L D (1997) Apoptosis mediates cell death following traumatic injury in rat hippocampal neurons. Neuroscience 79: 999-1004.

139. Sheng M (2001) Molecular organization of the postsynaptic specialization. Proc Natl Acad Sci USA 98: 7058-7061.
140. Sheng M, Kim M J (2002) Postsynaptic signaling and plasticity mechanisms. Science 298: 776-780.
141. Siman R, Noszek C, Kegerise C (1989) Calpain I activation is specifically related to excitatory amino acid induction of hippocampal damage. J Neurosci 9: 1579-1590.
142. Siman R, Noszek J C (1988) Excitatory amino acids activate calpain I and induce structural protein breakdown in vivo. Neuron 1: 279-287.
143. Smith D H, Wolf J A, Lusardi T A, Lee V M, Meaney D F (1999) High tolerance and delayed elastic response of cultured axons to dynamic stretch injury. J Neurosci 19: 4263-4269.
144. Stirling D P, Khodarahmi K, Liu J, McPhail L T, McBride C B, Steeves J D, Ramer M S, Tetzlaff W (2004) Minocycline treatment reduces delayed oligodendrocyte death, attenuates axonal dieback, and improves functional outcome after spinal cord injury. J Neurosci 24: 2182-2190.
145. Susin S A, Lorenzo H K, Zamzami N, Marzo I, Snow B E, Brothers G M, Mangion J, Jacotot E, Costantini P, Loeffler M, Larochette N, Goodlett D R, Aebersold R, Siderovski D P, Penninger J M, Kroemer G (1999) Molecular characterization of mitochondrial apoptosis-inducing factor. Nature 397: 441-446.
146. Tator C H, Koyanagi I (1997) Vascular mechanisms in the pathophysiology of human spinal cord injury. J Neurosurg 86: 483-492.
147. Teasdale G M, Graham D I (1998) Craniocerebral trauma: protection and retrieval of the neuronal population after injury. Neurosurgery 43: 723-737.
148. Tecoma E S, Monyer H, Goldberg M P, Choi D W (1989) Traumatic neuronal injury in vitro is attenuated by NMDA antagonists. Neuron 2: 1541-1545.
149. Tenneti L, D'Emilia D M, Troy C M, Lipton S A (1998) Role of caspases in N-methyl-D-aspartate-induced apoptosis in cerebrocortical neurons. J Neurochem 71: 946-959.
150. Thibault L E, Meaney D F, Anderson B J, Marmarou A (1992) Biomechanical aspects of a fluid percussion model of brain injury. J Neurotrauma 9: 311-322.
151. Trackey J L, Uliasz T F, Hewett S J (2001) SIN-1-induced cytotoxicity in mixed cortical cell culture: peroxynitrite-dependent and -independent induction of excitotoxic cell death. J Neurochem 79: 445-455.
152. Tymianski M (1996) Cytosolic calcium concentrations and cell death in vitro. In: Advances in Neurology: Cellular and molecular mechanisms of ischemic brain damage (Siesjo B K, Wieloch T, eds), pp 85-105. Philadelphia: Lippincott-Raven.
153. Tymianski M, Charlton M P, Carlen P L, Tator C H (1993) Source specificity of early calcium neurotoxicity in cultured embryonic spinal neurons. J Neurosci 13: 2085-2104.
154. Tymianski M, Sattler R, Zabramski J M, Spetzler R F (1998) A Characterization of Neuroprotection from Excitotoxicity by Moderate and Profound Hypothermia In Cultured Cortical Neurons Unmasks a Temperature-Insensitive Component of Glutamate Neurotoxicity. J Cereb Blood Flow Metab 18: 848-867.
155. Tymianski M, Tator C H (1996) Normal and abnormal calcium homeostasis in neurons: a basis for the pathophysiology of traumatic and ischemic central nervous system injury. Neurosurgery 38: 1176-1195.
156. Wang G J, Thayer S A (1996) Sequestration of glutamate-induced $Ca^{2+}$ loads by mitochondria in cultured rat hippocampal neurons. J Neurophysiol 76: 1611-1621.
157. Wang X (2001) The expanding role of mitochondria in apoptosis. Genes Dev 15: 2922-2933.
158. Wennersten A, Holmin S, Mathiesen T (2003) Characterization of Bax and Bcl-2 in apoptosis after experimental traumatic brain injury in the rat. Acta Neuropathol (Berl) 105: 281-288.
159. Yakovlev A G, Di X, Movsesyan V, Mullins P G, Wang G, Boulares H, Zhang J, Xu M, Faden A I (2001) Presence of DNA fragmentation and lack of neuroprotective effect in DFF45 knockout mice subjected to traumatic brain injury. Mol Med 7: 205-216.
160. Yu S P, Yeh C H, Sensi S L, Gwag B J, Canzoniero L M, Farhangrazi Z S, Ying, HS, Tian M, Dugan L L, Choi D W (1997) Mediation of neuronal apoptosis by enhancement of outward potassium current. Science 278: 114-117.
161. Yu S W, Wang H, Dawson T M, Dawson V L (2003) Poly(ADP-ribose) polymerase-1 and apoptosis inducing factor in neurotoxicity. Neurobiol Dis 14: 303-317.
162. Zhang L, Rzigalinski B A, Ellis E F, Satin L S (1996) Reduction of voltage-dependent $Mg2+$ blockade of NMDA current in mechanically injured neurons. Science 274: 1921-1923.
163. Zhang X, Chen J, Graham S H, Du L, Kochanek P M, Draviam R, Guo F, Nathaniel P D, Szabo C, Watkins S C, Clark R S (2002) Intranuclear localization of apoptosis-inducing factor (AIF) and large scale DNA fragmentation after traumatic brain injury in rats and in neuronal cultures exposed to peroxynitrite. J Neurochem 82: 181-191.
164. Zingarelli B, Day B J, Crapo J D, Salzman A L, Szabo C (1997) The potential role of peroxynitrite in the vascular contractile and cellular energetic failure in endotoxic shock. Br J Pharmacol 120: 259-267.
165. Zwienenberg M, Muizelaar J P (2001) Cerebral perfusion and blood flow in neurotrauma. Neurol Res 23: 167-174.
166. M. C. Morris, J. Depollier, J. Mery, F. Heitz, and G. Divita. A peptide carrier for the delivery of biologically active proteins into mammalian cells. Nat. Biotechnol. 19 (12):1173-1176, 2001.
167. Z. Mi, J. Mai, X. Lu, and P. D. Robbins. Characterization of a class of cationic peptides able to facilitate efficient protein transduction in vitro and in vivo. Mol. Ther. 2 (4):339-347, 2000.
168. M. Modo, R. P. Stroemer, E. Tang, T. Veizovic, P. Sowniski, and H. Hodges. Neurological sequelae and long-term behavioural assessment of rats with transient middle cerebral artery occlusion. J. Neurosci. Methods 104 (1):99-109, 2000.
169. A. J. Hunter, J. Hatcher, D. Virley, P. Nelson, E. Irving, S. J. Hadingham, and A. A. Parsons. Functional assessments in mice and rats after focal stroke. Neuropharmacology 39 (5):806-816, 2000.
170. O. House, M. L. Hackett, C. S. Anderson, and J. A. Horrocks. Pharmaceutical interventions for emotionalism after stroke. Cochrane. Database. Syst. Rev. (2): CD003690, 2004.
171. C. A. Barnes. Memory deficits associated with senescence: a neurophysiological and behavioral study in the rat. J. Comp Physiol Psychol. 93 (1):74-104, 1979.
172. R. Morris. Developments of a water-maze procedure for studying spatial learning in the rat. J. Neurosci. Methods 11 (1):47-60, 1984. 173. V. Mutel, D. Buchy, A. Klingelschmidt, J. Messer, Z. Bleuel, J. A. Kemp, and J. G. Richards. In vitro binding properties in rat brain of [3H]Ro 25-6981, a potent and selective antagonist of NMDA receptors containing NR2B subunits. J. Neurochem. 70 (5):2147-2155, 1998.

174. K. Williams. Ifenprodil, a novel NMDA receptor antagonist: site and mechanism of action. Curr. Drug Targets. 2 (3):285-298, 2001. 175. S. S. Nikam and L. T. Meltzer. NR2B selective NMDA receptor antagonists. Curr. Pharm. Des 8 (10):845-855, 2002. 176. T. K. McIntosh, R. Vink, L. Noble, I. Yamakami, S. Femyak, H. Soares, and A. L. Faden. Traumatic brain injury in the rat: characterization of a lateral fluid-percussion model. Neuroscience 28 (1):233-244, 1989.

177. Loschmann P A, De Groote C, Smith L, Wullner U, Fischer G, Kemp J A, Jenner P, Klockgether T. Antiparkinsonian activity of Ro 25-6981, a NR2B subunit specific NMDA receptor antagonist, in animal models of Parkinson's disease. Exp Neurol. 2004 May; 187(1):86-93.

What is claimed is:

1. A method of screening a peptide which binds to at least one PDZ domain and comprises a cell-membrane transduction domain for use in treating traumatic injury to the brain or spinal cord, comprising
deforming a flexible substrate to which neurons are attached to subject the neurons to a sublethal stretch;
inflicting a secondary injury on the stretched neurons;
determining survival of the stretched neurons treated with the peptide relative to a control in which stretched neurons are incubated without the peptide, wherein increased survival provides an indication the peptide is useful for treating traumatic brain injury.

2. The method of claim 1, wherein the inflicting step comprises treating the stretched neurons with NMDA to inflict the secondary injury.

3. The method of claim 1, wherein the inflicting step comprises treating the stretched neurons with glutamate to inflict the secondary injury.

4. The method of claim 1, wherein the neurons are treated with the peptide before the neurons are stretched.

5. The method of claim 1, wherein neurons are treated with the peptide after the neurons are stretched.

6. The method of claim 1, further comprising testing the peptide in an animal model of traumatic brain injury.

7. The method of claim 1, wherein the peptide inhibits binding of an NMDA receptor to a neuronal protein.

8. The method of claim 1, wherein survival is measured quantitative measurements of propidium iodide fluorescence.

* * * * *

SEQUENCE LISTING

```
<160> NUMBER OF SEQ ID NOS: 12

<210> SEQ ID NO 1
<211> LENGTH: 9
<212> TYPE: PRT
<213> ORGANISM: Unknown
<220> FEATURE:
<223> OTHER INFORMATION: synthetic peptide

<400> SEQUENCE: 1

Lys Leu Ser Ser Ile Glu Ser Asp Val
1               5

<210> SEQ ID NO 2
<211> LENGTH: 9
<212> TYPE: PRT
<213> ORGANISM: Unknown
<220> FEATURE:
<223> OTHER INFORMATION: synthetic peptide

<400> SEQUENCE: 2

Lys Leu Ser Ser Ile Glu Thr Asp Val
1               5

<210> SEQ ID NO 3
<211> LENGTH: 11
<212> TYPE: PRT
<213> ORGANISM: Unknown
<220> FEATURE:
<223> OTHER INFORMATION: synthetic peptide

<400> SEQUENCE: 3

Tyr Gly Arg Lys Lys Arg Arg Gln Arg Arg Arg
1               5                   10

<210> SEQ ID NO 4
<211> LENGTH: 20
<212> TYPE: PRT
<213> ORGANISM: Unknown
<220> FEATURE:
<223> OTHER INFORMATION: synthetic peptide

<400> SEQUENCE: 4

Tyr Gly Arg Lys Lys Arg Arg Gln Arg Arg Arg Lys Leu Ser Ser Ile
1               5                   10                  15

Glu Ser Asp Val
            20

<210> SEQ ID NO 5
<211> LENGTH: 20
<212> TYPE: PRT
<213> ORGANISM: Unknown
<220> FEATURE:
<223> OTHER INFORMATION: synthetic peptide

<400> SEQUENCE: 5
```

```
Tyr Gly Arg Lys Lys Arg Gln Arg Arg Lys Leu Ser Ser Ile
1               5                   10                  15

Glu Thr Asp Val
            20
```

<210> SEQ ID NO 6
<211> LENGTH: 12
<212> TYPE: PRT
<213> ORGANISM: Unknown
<220> FEATURE:
<223> OTHER INFORMATION: synthetic peptide

<400> SEQUENCE: 6

```
Cys Ser Lys Asp Thr Met Glu Lys Ser Glu Ser Leu
1               5                   10
```

<210> SEQ ID NO 7
<211> LENGTH: 11
<212> TYPE: PRT
<213> ORGANISM: Unknown
<220> FEATURE:
<223> OTHER INFORMATION: synthetic peptide

<400> SEQUENCE: 7

```
Lys Ala Leu Gly Ile Ser Tyr Gly Arg Lys Lys
1               5                   10
```

<210> SEQ ID NO 8
<211> LENGTH: 21
<212> TYPE: PRT
<213> ORGANISM: Unknown
<220> FEATURE:
<223> OTHER INFORMATION: synthetic peptide

<400> SEQUENCE: 8

```
Lys Glu Thr Trp Trp Glu Thr Trp Thr Glu Trp Ser Gln Pro Lys
1               5                   10                  15

Lys Lys Arg Lys Val
            20
```

<210> SEQ ID NO 9
<211> LENGTH: 12
<212> TYPE: PRT
<213> ORGANISM: Unknown
<220> FEATURE:
<223> OTHER INFORMATION: synthetic peptide

<400> SEQUENCE: 9

```
Pro Pro Arg Leu Arg Lys Arg Arg Gln Leu Asn Met
1               5                   10
```

<210> SEQ ID NO 10
<211> LENGTH: 12
<212> TYPE: PRT
<213> ORGANISM: Unknown
<220> FEATURE:
<223> OTHER INFORMATION: synthetic peptide

<400> SEQUENCE: 10

```
Pro Ile Arg Arg Arg Lys Lys Leu Arg Arg Leu Lys
1               5                   10
```

<210> SEQ ID NO 11
<211> LENGTH: 12
<212> TYPE: PRT

```
-continued

<213> ORGANISM: Unknown
<220> FEATURE:
<223> OTHER INFORMATION: synthetic peptide

<400> SEQUENCE: 11

Arg Arg Gln Arg Arg Thr Ser Lys Leu Met Lys Arg
1               5                   10

<210> SEQ ID NO 12
<211> LENGTH: 20
<212> TYPE: PRT
<213> ORGANISM: Unknown
<220> FEATURE:
<223> OTHER INFORMATION: synthetic peptide

<400> SEQUENCE: 12

Tyr Gly Arg Lys Lys Arg Arg Gln Arg Arg Lys Leu Ser Ser Ile
1               5                   10                  15

Glu Ala Asp Ala
            20
```